(12) United States Patent
Moutafis et al.

(10) Patent No.: US 6,669,710 B2
(45) Date of Patent: Dec. 30, 2003

(54) LIQUID JET-POWERED SURGICAL INSTRUMENTS

(75) Inventors: Timothy E. Moutafis, Gloucester, MA (US); Donald C. Freeman, Jr., Burlington, MA (US); Kevin Staid, Lowell, MA (US)

(73) Assignee: Hydrocision, Inc., Andover, MA (US)

( * ) Notice: Subject to any disclaimer, the term of this patent is extended or adjusted under 35 U.S.C. 154(b) by 0 days.

(21) Appl. No.: 10/262,274

(22) Filed: Oct. 1, 2002

(65) Prior Publication Data

US 2003/0040763 A1 Feb. 27, 2003

Related U.S. Application Data

(62) Division of application No. 09/480,500, filed on Jan. 10, 2000, now Pat. No. 6,511,493.

(51) Int. Cl.[7] ............................................. A61B 17/32
(52) U.S. Cl. ...................................................... 606/167
(58) Field of Search ................................ 606/167, 170, 606/171, 174, 181, 159, 190; 604/22

(56) References Cited

U.S. PATENT DOCUMENTS

| 1,889,425 A | 11/1932 | Sorensen |
| 1,902,418 A | 3/1933 | Pilgrim |
| 2,937,444 A | 5/1960 | Kern |
| 3,128,079 A | 4/1964 | DeGroff |
| 3,210,848 A | 10/1965 | Bizzigotti |
| 3,578,872 A | 5/1971 | McBurnie |
| 3,590,813 A | 7/1971 | Roszyk |
| 3,731,384 A | 5/1973 | Brooks et al. |
| 3,731,385 A | 5/1973 | Farber et al. |

(List continued on next page.)

FOREIGN PATENT DOCUMENTS

| DE | 3320076 A1 | 12/1984 |
| DE | 3421390 A1 | 12/1985 |
| DE | 4018736 A1 | 1/1992 |

(List continued on next page.)

OTHER PUBLICATIONS

Balje, "Turbomachines A guide to design, selection, and theory", John Wiley & Sons publisher, chap. 5, sect. 3, pp. 252–259, 1981.

(List continued on next page.)

Primary Examiner—Kevin T. Truong
(74) Attorney, Agent, or Firm—Wolf, Greenfield & Sacks, P.C.

(57) ABSTRACT

The present invention provides a series of devices useful for surgical procedures utilizing rotatable components for grinding, cutting, ablating, polishing, drilling, screwing, etc., tissues of the body of a patient. The invention includes, in one aspect, a series of devices comprising surgical instruments including rotatable shafts, and surgical components drivable by the shafts that can be utilized for contact with tissue in a surgical operating field. Some preferred surgical instruments provided by the invention utilize a liquid jet-driven rotor mechanism for driving rotation of the rotatable shaft. Some preferred instruments provided by the invention include both a liquid jet-driven rotor mechanism and a nozzle at the distal end of the instrument for forming a liquid cutting jet for cutting or ablating tissue of a patient. Such instruments can include a liquid flow directing valve therein that includes a pressure-tight sealing component comprising a sealing element that is constructed and arranged to be slidably moveable within a cylinder of the valve. The invention provides methods for utilizing the inventive surgical instruments in surgical procedures involving both cutting or ablating tissue of a patient with a liquid cutting jet and grinding, cutting, or ablating tissue with a rotating surface of a surgical instrument.

7 Claims, 25 Drawing Sheets

U.S. PATENT DOCUMENTS

| | | |
|---|---|---|
| 3,818,913 A | 6/1974 | Wallach |
| 3,835,858 A | 9/1974 | Hagen |
| 3,906,954 A | 9/1975 | Baehr et al. |
| 3,930,505 A | 1/1976 | Wallach |
| 3,976,077 A | 8/1976 | Kerfoot, Jr. |
| 3,994,208 A | 11/1976 | Boyer |
| 4,009,645 A | 3/1977 | Freimuth |
| 4,024,866 A | 5/1977 | Wallach |
| 4,061,146 A | 12/1977 | Baehr et al. |
| 4,111,490 A | 9/1978 | Liesveld |
| 4,116,452 A | 9/1978 | Schanz |
| 4,137,804 A | 2/1979 | Gerber et al. |
| 4,196,909 A | 4/1980 | Porsch et al. |
| 4,214,507 A | 7/1980 | Hock et al. |
| 4,229,139 A | 10/1980 | Marantette et al. |
| 4,235,595 A | 11/1980 | Arnegger |
| 4,245,624 A | 1/1981 | Komiya |
| 4,267,862 A | 5/1981 | Neff et al. |
| 4,270,440 A | 6/1981 | Lewis, II |
| 4,281,590 A | 8/1981 | Weaver |
| 4,282,867 A | 8/1981 | Du Toit |
| 4,294,251 A | 10/1981 | Greenwald et al. |
| 4,368,734 A | 1/1983 | Banko |
| 4,435,902 A | 3/1984 | Mercer et al. |
| 4,517,977 A | 5/1985 | Frost |
| 4,560,373 A | 12/1985 | Sugino et al. |
| 4,583,531 A | 4/1986 | Mattchen |
| 4,589,412 A | 5/1986 | Kensey |
| 4,601,235 A | 7/1986 | Roberts |
| 4,631,052 A | 12/1986 | Kensey |
| 4,637,551 A | 1/1987 | Seeger, Jr. et al. |
| 4,690,140 A | 9/1987 | Mecca |
| 4,690,672 A | 9/1987 | Veltrup |
| 4,694,828 A | 9/1987 | Eichenbaum |
| 4,705,038 A | 11/1987 | Sjostrom et al. |
| 4,715,848 A | 12/1987 | Beroza |
| 4,729,763 A | 3/1988 | Henrie |
| 4,730,550 A | 3/1988 | Bramstedt et al. |
| 4,735,129 A | 4/1988 | Sjoberg |
| 4,735,604 A | 4/1988 | Watmough et al. |
| 4,735,620 A | 4/1988 | Ruiz |
| 4,747,821 A | 5/1988 | Kensey et al. |
| 4,749,376 A | 6/1988 | Kensey et al. |
| 4,790,813 A | 12/1988 | Kensey |
| 4,798,339 A | 1/1989 | Sugino et al. |
| 4,813,343 A | 3/1989 | Schaefer |
| 4,815,462 A | 3/1989 | Clark |
| 4,827,615 A | 5/1989 | Graham |
| 4,827,679 A | 5/1989 | Earle, III |
| 4,842,578 A | 6/1989 | Johnson et al. |
| 4,898,574 A | 2/1990 | Uchiyama et al. |
| 4,898,579 A | 2/1990 | Groshong et al. |
| 4,913,698 A | 4/1990 | Ito et al. |
| 4,935,006 A | 6/1990 | Hasson |
| 4,937,985 A | 7/1990 | Boers et al. |
| 4,940,399 A | 7/1990 | Gorton et al. |
| 4,986,807 A | 1/1991 | Farr |
| 5,002,546 A | 3/1991 | Romano |
| 5,018,670 A | 5/1991 | Chalmers |
| 5,037,431 A | 8/1991 | Summers et al. |
| 5,042,984 A | 8/1991 | Kensey et al. |
| 5,052,624 A | 10/1991 | Boers et al. |
| 5,057,098 A | 10/1991 | Zelman |
| 5,074,862 A | 12/1991 | Rausis |
| 5,097,849 A | 3/1992 | Kensey et al. |
| 5,111,652 A | 5/1992 | Andre |
| 5,114,399 A | 5/1992 | Kovalcheck |
| 5,125,582 A | 6/1992 | Surjaatmadja et al. |
| 5,135,482 A | 8/1992 | Neracher |
| 5,135,484 A | 8/1992 | Wright |
| 5,162,016 A | 11/1992 | Malloy |
| 5,195,958 A | 3/1993 | Phillips |
| 5,205,779 A | 4/1993 | O'Brien et al. |
| 5,217,465 A | 6/1993 | Steppe |
| 5,230,704 A | 7/1993 | Moberg et al. |
| 5,242,449 A | 9/1993 | Zaleski |
| 5,250,065 A | 10/1993 | Clement et al. |
| 5,259,842 A | 11/1993 | Plechinger et al. |
| RE34,556 E | 3/1994 | Sjostrom et al. |
| 5,300,022 A | 4/1994 | Klapper et al. |
| 5,314,375 A | 5/1994 | O'Brien et al. |
| 5,318,518 A | 6/1994 | Plechinger et al. |
| 5,320,599 A | 6/1994 | Griep et al. |
| 5,322,504 A | 6/1994 | Doherty et al. |
| 5,339,799 A | 8/1994 | Kami et al. |
| 5,350,390 A | 9/1994 | Sher |
| 5,364,395 A | 11/1994 | West, Jr. |
| 5,370,609 A | 12/1994 | Drasler et al. |
| 5,374,401 A | 12/1994 | von Berg |
| 5,395,315 A | 3/1995 | Griep |
| 5,409,376 A | 4/1995 | Murphy |
| 5,423,752 A | 6/1995 | Haber et al. |
| 5,441,482 A | 8/1995 | Clague et al. |
| 5,449,369 A | 9/1995 | Imran |
| 5,453,088 A | 9/1995 | Boudewijn et al. |
| 5,454,827 A | 10/1995 | Aust et al. |
| 5,468,028 A | 11/1995 | Olson |
| 5,476,450 A | 12/1995 | Ruggio |
| 5,496,267 A | 3/1996 | Drasler et al. |
| 5,505,729 A | 4/1996 | Rau |
| 5,511,464 A | 4/1996 | Cezanne et al. |
| 5,512,044 A | 4/1996 | Duer |
| 5,524,821 A | 6/1996 | Yie et al. |
| 5,527,330 A | 6/1996 | Tovey |
| 5,527,331 A | 6/1996 | Kresch et al. |
| 5,533,879 A | 7/1996 | Chen |
| 5,536,242 A | 7/1996 | Willard et al. |
| 5,551,448 A | 9/1996 | Matula et al. |
| 5,556,406 A | 9/1996 | Gordon et al. |
| 5,562,186 A | 10/1996 | Osenbaugh |
| 5,562,640 A | 10/1996 | McCabe et al. |
| 5,562,692 A | 10/1996 | Bair |
| 5,591,184 A | 1/1997 | McDonnell et al. |
| 5,607,391 A | 3/1997 | Klinger et al. |
| 5,618,293 A | 4/1997 | Sample et al. |
| 5,620,414 A | 4/1997 | Campbell, Jr. |
| 5,626,072 A | 5/1997 | Mirand et al. |
| 5,643,299 A | 7/1997 | Bair |
| 5,672,945 A | 9/1997 | Krause |
| 5,674,226 A | 10/1997 | Doherty et al. |
| 5,697,281 A | 12/1997 | Eggers et al. |
| 5,709,697 A | 1/1998 | Ratcliff et al. |
| 5,711,151 A | 1/1998 | Engfer |
| 5,713,849 A | 2/1998 | Bosma et al. |
| 5,713,851 A | 2/1998 | Boudewijn et al. |
| 5,735,815 A | 4/1998 | Bair |
| 5,749,885 A | 5/1998 | Sjostrom et al. |
| 5,779,713 A | 7/1998 | Turjanski et al. |
| 5,785,675 A | 7/1998 | Drasler et al. |
| 5,788,667 A | 8/1998 | Stoller |
| 5,803,733 A | 9/1998 | Trott et al. |
| 5,810,809 A | 9/1998 | Rydell |
| 5,849,023 A | 12/1998 | Mericle |
| 5,853,384 A | 12/1998 | Bair |
| 5,865,442 A | 2/1999 | Iwashita |
| 5,871,462 A | 2/1999 | Yoder et al. |
| 5,899,915 A | 5/1999 | Saadat |
| 5,904,681 A | 5/1999 | West, Jr. |
| 5,927,976 A | 7/1999 | Wu |
| 5,941,162 A | 8/1999 | Kiesel |
| 5,941,876 A | 8/1999 | Nardella et al. |

| | | |
|---|---|---|
| 5,941,893 A | 8/1999 | Saadat |
| 5,944,686 A | 8/1999 | Patterson et al. |
| 5,947,988 A | 9/1999 | Smith |
| 5,960,700 A | 10/1999 | Staggs et al. |
| 6,017,354 A | 1/2000 | Culp et al. |
| 6,045,564 A * | 4/2000 | Walen ........................ 606/167 |
| 6,066,150 A | 5/2000 | Gonon |
| 6,083,189 A | 7/2000 | Gonon et al. |
| 6,085,631 A | 7/2000 | Kownacki |
| 6,099,514 A | 8/2000 | Sharkey et al. |
| 6,206,898 B1 | 3/2001 | Honeycutt et al. |
| 6,216,573 B1 | 4/2001 | Moutafis et al. |
| 6,280,302 B1 | 8/2001 | Hashish et al. |
| 6,322,533 B1 | 11/2001 | Gonon |
| 6,375,635 B1 | 4/2002 | Moutafis et al. |
| 6,402,715 B2 | 6/2002 | Manhes |
| 6,423,028 B1 | 7/2002 | Gonon |
| 6,451,017 B1 | 9/2002 | Moutafis et al. |
| 6,464,567 B2 | 10/2002 | Hashish et al. |
| 6,491,660 B2 * | 12/2002 | Guo et al. .................... 604/22 |
| 6,508,823 B1 | 1/2003 | Gonon |
| 6,511,493 B1 | 1/2003 | Moutafis et al. |
| 6,544,220 B2 | 4/2003 | Shuman et al. |
| 2001/0002562 A1 | 6/2001 | Moutafis et al. |
| 2002/0111579 A1 | 8/2002 | Moutafis et al. |
| 2002/0176788 A1 | 11/2002 | Moutafis et al. |
| 2002/0177802 A1 | 11/2002 | Moutafis et al. |
| 2003/0009166 A1 | 1/2003 | Moutafis et al. |
| 2003/0055404 A1 | 3/2003 | Moutafis |

FOREIGN PATENT DOCUMENTS

| | | |
|---|---|---|
| DE | 1 9734890 C1 | 7/1999 |
| EP | 0 175 096 B1 | 3/1986 |
| EP | 0 253 478 B1 | 1/1988 |
| EP | 0 258 901 A2 | 3/1988 |
| EP | 0 280 972 A1 | 9/1988 |
| EP | 0 335 861 B1 | 10/1989 |
| EP | 0 411 170 A1 | 2/1991 |
| EP | 0 442 579 A1 | 8/1991 |
| EP | 0 470 781 A1 | 2/1992 |
| EP | 0 485 133 A1 | 5/1992 |
| EP | 0 489 496 A1 | 6/1992 |
| EP | 0 551 920 B1 | 7/1993 |
| EP | 0 555 549 A1 | 8/1993 |
| EP | 0 620 016 A1 | 10/1994 |
| EP | 0 636 345 A1 | 2/1995 |
| EP | 0 637 453 A1 | 2/1995 |
| EP | 0 693 295 A1 | 1/1996 |
| EP | 0 737 450 A1 | 10/1996 |
| EP | 0 806 213 A1 | 11/1997 |
| GB | 199057 | 6/1923 |
| WO | WO 90/05493 | 5/1990 |
| WO | WO 94/10917 | 5/1994 |
| WO | WO 94/28807 | 12/1994 |
| WO | WO 96/24299 | 8/1996 |
| WO | WO 96/39954 | 12/1996 |
| WO | WO 96/40476 | 12/1996 |
| WO | WO 99/33510 | 7/1999 |
| WO | WO 00/69348 | 11/2000 |
| WO | WO 01/50965 | 7/2001 |
| WO | WO 01/50966 | 7/2001 |

OTHER PUBLICATIONS

Wilson et al., "The design of high–efficiency turbomachinery and gas turbines" Prentice Hall publisher, $2^{nd}$ edition, p. 31, 1998.

Water Jet Dissector, Hepatotom® Supersonic Microjet Dissector brochure, Medical Exports AG.

Aeikens, "Cracking of ureter calculi by high speed water jet pulses," $8^{th}$ International Symposium on Jet Cutting Technology, Paper 15, pp. 157–166, Sep. 9–11, 1986.

Baer et al., "Jet–cutting—an alternative to the ultrasonic aspirator?," Chirurg, vol. 61, p. 735, 1990, and Reply to commentary.

Baer et al., "New wate–jet dissector: Initial experience in hepatic surgery," Br. J. Surg., vol. 78, pp. 502–503, Apr. 1991.

Baer et al., "Hepatic surgery facilitated by a new jet dissector," HPB Surgery, vol. 4, pp. 137–146, 1991.

Baer et al., "Subtotal hepatectomy: A new procedure based on the inferior right hepatic vein," Br. J. Surg., vol. 78, pp. 1221–1222, Oct. 1991.

Baer et al., "Water–jet dissection in hepatic surgery," Minimally Invasive Therapy, vol. 1, pp. 169–172, 1992.

Beard, "Water jet puts surgeons at the cutting edge," New Scientist, Jul. 23, 1994.

Bücker et al., "Comparative in vitro study of two percutaneous hydrodynamic thrombectomy systems," Journal of Vascular and Interventional Radiology, vol. 7, No. 3, pp. 445–449, May–Jun. 1996.

Douek et al., "Functional properties of a prototype rheolytic catheter for percutaneous thrombectomy in vitro investigations," Investigative Radiology, vol. 29, No. 5, pp. 547–552, 1994.

Drasler et al., "A rheolytic system for percutaneous coronary and peripheral plaque removal," Angiology—The Journal of Vascular Diseases, vol. 42, No. 2, pp. 90–98, 1991.

Drasler et al., "Rheolytic catheter for percutaneous removal of thrombus," Radiology, vol. 182, pp. 263–267, Jan. 1992.

Field, "The physics of liquid impact, shock wave interactions with cavities, and the implications to shock wave lithotripsy," Phys. Med. Biol. vol. 36, No. 11, pp. 1475–1484, 1991.

Giraud et al., "Bone cutting," clin. Phys. Physiol. Meas., vol. 12, No. 1, pp. 1–19, 1991.

Hata et al., "Liver resection in children, using a water–jet," Journal of Pediatric Surgery, vol. 29, No. 5, pp. 648–650, May 1994.

Izumi et al., "Hepatic resection using a water jet dissector," Surgery Today Jpn. J. Surg., vol. 23, pp. 31–35, 1993.

Jessen et al., "Endoscopic jet–cutting A new method for stone destruction in the common bile duct," $6^{th}$ Internal Symposium on Jet Cutting Technology, Paper B1, pp. 39–52, Apr. 6–8, 1982.

Jessen et al., "Endoscopic jet cutting of human gallstones," $7^{th}$ Internal Symposium on Jet Cutting Technology, Paper D4, pp. 211–220, Jun. 26–28, 1984.

Kobayashi et al., "Experimental study of water jet angioplasty," Vascular Surgery—International Conference, Oct. 1993, vol. 2, pp. 626–631.

Müller–Hülsbeck et al., "Rheolytic thrombectomy of an acutely thrombosed transjugular intrahepatic portosystemic stent shunt," CardioVasc. Intervent. Radiol., vol. 19, pp. 294–297, 1996.

Overbosch et al., "Occluded hemodialysis shunts: Dutch multicenter experience with the hydrolyser catheter," Radiology, vol. 201, No. 2, pp. 485–488, 1996.

Papachristou et al., "Resection of the liver with a water jet," Br. J. Surg., vol. 69, pp. 93–94, 1982.

Persson et al., "Transection of the liver with a water jet," Surgery, Gynecology & Obstetrics, vol. 168, pp. 267–268, Mar. 1989.

Reekers et al., "Catheter for percutaneous thrombectomy: First clinical experience," Radiology, vol. 188, No. 3, pp. 871–874, 1993.

Schob et al., "The multimodal water jet dissector—a technology for laparoscopic liver surgery," End. Surg., vol. 2, pp. 311–314, 1994.

Schob et al., "Experimental laparoscopic liver resection with a multimodal water jet dissector," British Journal of Surgery, vol. 82, pp. 392–393, 1995.

Shimi, "Dissection techniques in laparoscopic surgery: A review," J.R. Coll. Surg. Edinb., vol. 40, pp. 249–259, Aug. 1995.

Spence, "Emerging trends in surgical blood transfusion," Seminars in Hematology, vol. 34, No. 3, suppl. 2, pp. 48–53, Jul. 1997.

Summers et al., "The impact of waterjets on human flesh," $9^{th}$ International Symposium on Jet Cutting Technology, Paper H4, pp. 423–433, Oct. 4–6, 1988.

Terzis et al., "A new system for cutting brain tissue preserving vessels: Water jet cutting," British Journal of Neurosurgery, vo. 3, pp. 361–366, 1989.

Truchot et al., "Development of a cryogenic waterjet technique for biomaterial processing applications," $6^{th}$ American Water Jet Conference, paper 35, pp. 473–480, Aug. 24–27, 1991.

Uchino et al., "Surgical cutting of the liver by water jet," $9^{th}$ International Symposium on Jet Cutting Technology, Post 1, pp. 629–639, Oct. 4–6, 1988.

Van Ommen et al., "Removal of thrombus from aortocoronary bypass grafts and coronary arteries using the 6Fr hydrolyser," The American Journal of Cardiology, vol. 79, pp. 1012–1016, Apr. 1997.

Vijay, "A critical examination of the use of water jets for medical applications," $5^{th}$ American Water Jet Conference, Paper/Communication 42, pp. 425–448, Aug. 29–31, 1989.

Zhong et al., "Propagation of shock waves in elastic solids caused by cavitation microjet impact. II: Application in extracorporeal shock wave lithotripsy," J. Acoust. Soc. Am., vol. 94, No 1, pp. 29–36, Jul. 1993.

\* cited by examiner $b = \ell \Phi \tan$

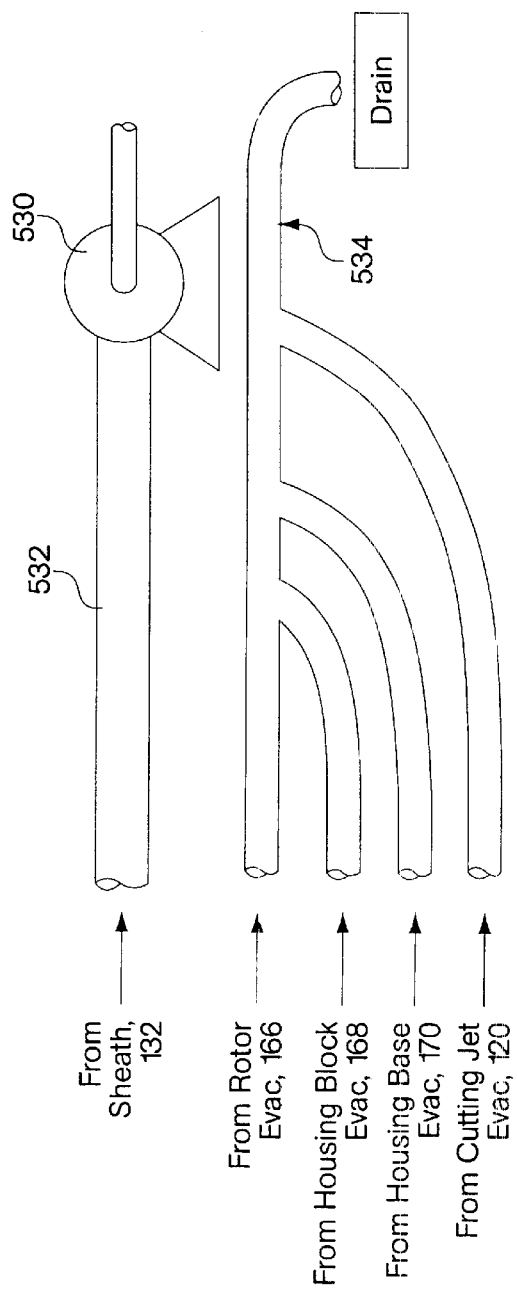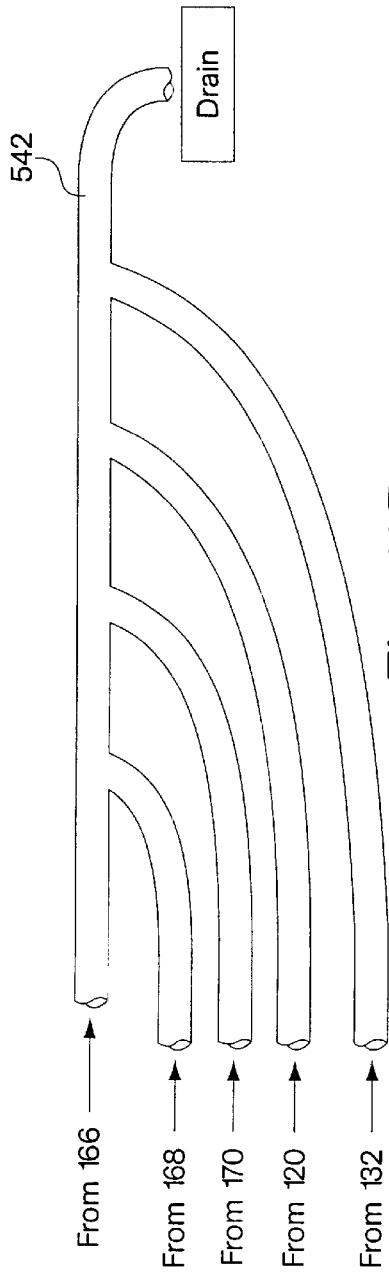
Fig. 11A
Fig. 11B

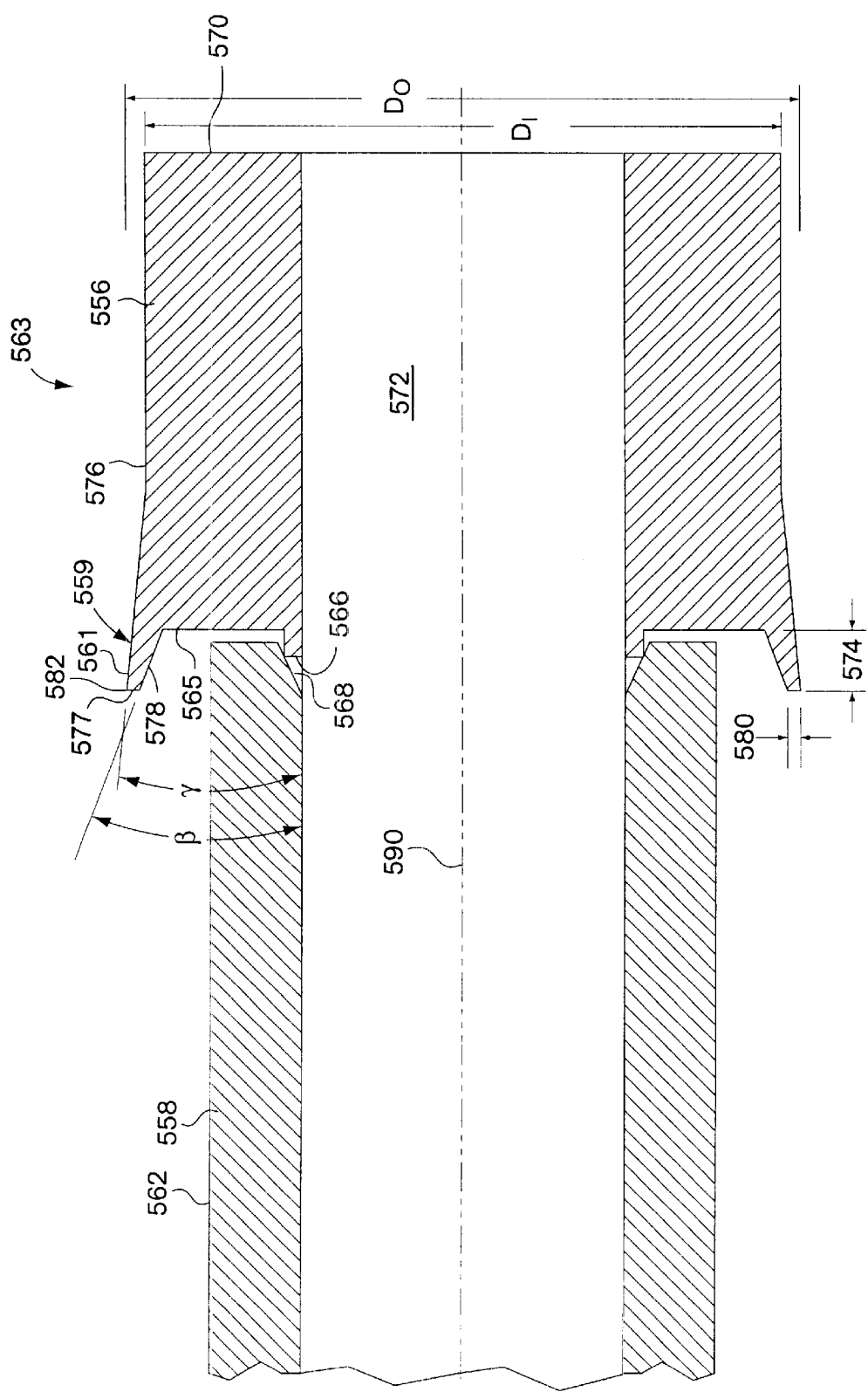

LIQUID JET-POWERED SURGICAL INSTRUMENTS

RELATED APPLICATIONS

This application is a divisional of U.S. patent application Ser. No. 09/480,500, filed Jan. 10, 2000, now U.S. Pat. No. 6,511,493 entitled Liquid Jet-Powered Surgical Instruments by Timothy E. Moutafis et al., and incorporated herein by reference.

FIELD OF THE INVENTION

The invention relates to surgical instruments, more specifically to surgical instruments providing rotating shafts for performing surgical functions, and to methods for using the instruments in surgical procedures.

BACKGROUND OF THE INVENTION

Traditionally, many surgical procedures have been performed on patients using open surgical methods that utilize relatively large incisions to expose a surgical field. Many traditional methods have also typically utilized surgical tools such as scalpels, scrapers, blunt dissectors, lasers, electrosurgical devices, etc., which can have poor tissue differentiating capability and which can sometimes cause inadvertent damage to tissue surrounding a surgical treatment site unless carefully utilized. Open surgery with such prior art surgical instruments often involves extensive trauma to the patient, with associated problems of long recovery periods and potential complications.

There has been a trend in recent years to perform many surgical procedures using less invasive techniques by accessing surgical sites via small holes through the skin or through body orifices. These techniques are known as "minimally invasive surgery." Minimally invasive surgical techniques commonly employed include endoscopic, laparoscopic, and arthroscopic surgical procedures. Minimally invasive surgical procedures are commonly preferred to open surgical procedures for many applications because the minimally invasive procedures induce less trauma to the patient during surgery and involve, in many cases, fewer potential complications and reduced recovery time.

A variety of surgical instruments have been developed and utilized both for minimally invasive surgical procedures and for more traditional open surgical procedures. Frequently used instruments include blade and scalpel-type instruments, motorized rotary cutting and/or grinding instruments, laser instruments, liquid jet cutting instruments, and electrosurgical instruments. Typically, prior art instruments suffer from a variety of disadvantages. For example, typical prior art surgical instruments, especially those utilized for minimally invasive surgical procedures, have distal ends including a single component for performing a particular surgical function. Surgical instruments having distal ends including, for example, a rotating cutting or grinding head, a tissue-ablating laser, a liquid cutting jet, or an electrosurgical cutting jet are known in the art. Many of these prior art instruments suffer from a variety of disadvantages. For example, instruments having a distal end configured to perform only a cutting function must be removed from a surgical field of a patient and replaced with additional instruments if other surgical functions, such as grinding or electrocautery, are required. Similarly, instruments including, for example, a distal end having a grinding component or an electrosurgical or electrocautery component must be removed from a surgical site and exchanged with additional instrumentation for performing other functions, such as surgical cutting, etc. Such a removal and exchange of surgical instruments, especially when performing during minimally invasive surgical procedures, can be undesirable both from the standpoint of the speed and convenience, and also from the standpoint of the safety and effectiveness of the surgical instrument in performing complex surgical procedures requiring multiple tasks to be performed in the surgical operating field.

For a variety of surgical procedures, including a variety of minimally invasive surgical procedures, it is often desirable to utilize a surgical instrument including a rotating component in the surgical field. Instruments providing rotating components may be advantageously utilized for surgical tasks such as grinding, polishing, drilling, cutting with rotating cutting blades, etc. Typical prior art surgical instruments providing rotating shafts for use in surgical procedures typically have employed electric motors to drive rotation of the shafts, or, alternatively, have employed pneumatically driven rotating turbine rotors. Such prior art instruments suffer from a variety of disadvantages. For example, instruments driven by electric motors often create rotation of grinding burrs, or other tissue contacting components connected to the rotating shaft, having relatively poor responsiveness of the rotational speed of the shaft to the resistance and torque applied to the tissue contacting component in the surgical field during operation. This poor responsiveness and feedback can, in some instances, lead to a variety of difficulties such as difficulty in maintaining contact of the rotating tissue contacting component, for example grinding burr, of the device with tissue in a particular desired location within a surgical field (e.g., due to skating or skipping of a grinding burr along the surface being ground), and also can lead to undesirable transmission of torque to a handle or other user interface of the surgical device, potentially causing a lack of operator control and unintended tissue damage.

Pneumatically powered surgical devices providing rotating shafts typically provide better compensation of the rotational speed of the rotating shaft with applied load than electric motor powered instruments; however, pneumatically powered instruments require that surgical instruments be coupled to a source of highly pressurized gas during operation of the instruments, which can be inconvenient, expensive, or undesirable.

U.S. Pat. No. 5,803,733 to Trott et al. describes a pneumatically powered surgical handpiece in which the pressurized fluid inlet is axially directed relative to the handpiece body. The handpiece includes a reaction-type turbine that is rotated by fluid flowing within a closed conduit. The handpiece utilizes a cantilevered turbine rotor, wherein the output shaft of the handpiece and the turbine rotor rotate about axes which are co-linear.

Surgical instruments utilizing liquid-driven turbine rotors are also known. U.S. Pat. No. 4,631,052 to Kensey describes an elongated, flexible recanalization catheter that includes a working head which is adapted to be rotated by a turbine drive in operation. The turbine drive utilizes a liquid-driven turbine rotor comprising a reaction turbine whose rotational motion is imparted by pressure driven liquid flowing in a closed conduit. The turbine rotor and the rotating working head of the device are directly coupled together so that they rotate at essentially the same speed during operation. In addition, the rotor assembly is disposed at the distal end of the catheter and is essentially completely submerged in liquid during operation.

U.S. Pat. No. 4,690,140 to Mecca describes a catheter for use in the removal of deposits lining the interior wall of a blood vessel that includes a rotating cutting device at its distal end. Rotational motion of the rotating cutting device is imparted by flow of a pressure-driven liquid. The cutting surfaces of the rotating cutting device and the turbine rotor comprise a single component rotating at essentially the same speed and about the same rotational axis. As with the '052 patent described above, the rotating cutting element of the '140 patent is disposed at the distal end of the catheter such that the turbine rotor causing rotation of the device is essentially completely submerged in liquid during operation.

Surgical instruments providing electrosurgical cutting or cauterizing electrodes in combination with rotating surgical components or liquid perfusion and/or aspiration capabilities are also known.

U.S. Pat. No. 5,527,331 to Kresch describes a tissue resection device for use in an organ inflated with a non-conductive fluid. The distal end of the device can include a perfusion lumen, a rotatable drive tube, and a drive tube aspiration lumen. A cutting tip can be mounted on the distal end of the drive tube. In some configurations, the cutting tip is further configured to act as an electrosurgical resection electrode.

U.S. Pat. No. 5,941,876 to Nardella et al. describes an electrosurgical apparatus that includes a rotary, tissue affecting device, such as a rotating blade component, a rotating drill, or a rotating shaving/ablating device. The rotating device also serves as an active, energy delivering electrode for electrosurgery.

U.S. Pat. No. 5,254,117 to Rigby et al. describes a multi-functional endoscopic probe apparatus capable of applying either a low or high frequency voltage to cut and cauterize tissue. The apparatus includes an elongated multi-lumen tube. The multi-lumen tube includes an irrigation lumen, a suction lumen, and a lumen providing passage for a slidably extendible and retractable electrosurgical cutting tip. The inner and outer surfaces of the multi-lumen tube can be coated with a layer of polyamide of uniform thickness for insulation. In some embodiments, the outer surface of the multi-lumen tube is further coated with a shrink-wrapped polytetrafluoroethylene insulating layer.

U.S. Pat. No. 5,429,596 to Arias et al. describes an endoscopic electrosurgical suction-irrigation instrument with insertable probes and attachments. The instrument includes a fluid chamber that is sealed at its proximal end, includes slit valve for receiving the probes, and is connected at its distal end to a cannula through which the inserted probes extend. The fluid chamber can be selectively provided with suction and/or irrigation and includes an electrical contact for supplying voltage to an inserted electrosurgical probe. Depending on the probe configuration, suction and/or irrigation can be provided in an annular space between the probe and the cannula or through the probe.

International Patent Application No. WO 97/24074 having inventors Isaacson et al. describes a hysteroscopic electrosurgical device. The device includes an electrosurgical probe, an irrigation channel, and an evacuation channel. In some configurations, a return electrode of the bipolar system provided by the instrument extends along an inner and/or outer surface of a sheath that is concentric about the positive electrode assembly.

While the above mentioned surgical instruments represent, in some instances, improvements over many prior art surgical instruments for performing open and minimally invasive surgical procedures, there remains a need in the art to provide surgical instruments which have improved cutting, ablation, grinding, and/or tissue cauterizing capabilities, and which also have the ability to be utilized in a wide variety of open and/or minimally invasive surgical procedures to perform a variety of surgical functions. The present invention provides, in many embodiments, such improved surgical instruments, and further provides methods for their use in a variety of surgical procedures.

SUMMARY OF THE INVENTION

The present invention provides a series of devices useful for surgical procedures utilizing rotatable components for grinding, cutting, ablating, polishing, drilling, screwing, etc., tissues of the body of a patient. The invention includes, in one aspect, a series of devices comprising surgical instruments including rotatable shafts, and surgical components drivable by the shafts that are constructed and arranged for contact with tissue in a surgical operating field. In another aspect, the invention provides a pressure-tight sealing component comprising an element constructed and arranged to be slidably moveable within a cylinder and, in yet another aspect, the invention provides a method for utilizing the inventive surgical instruments.

In one aspect, a series of devices comprising surgical instruments are described. One device comprises a surgical instrument having a distal end adapted to perform a surgical procedure on a patient and a proximal end adapted to be controllable by an operator. The instrument includes a rotatable shaft. The instrument further includes a surgical component that is drivable by the shaft and constructed and arranged for contact with a tissue in a surgical operating field. The instrument further includes a liquid jet-driven rotatable rotor. The rotor is drivingly coupled to the rotatable shaft, when the instrument is in operation, such that the rotation of the liquid jet-driven rotatable rotor causes a corresponding rotation of the rotatable shaft. Furthermore, the liquid jet-driven rotatable rotor is maintained in a surrounding gaseous environment while being rotatably driven by at least one liquid jet during operation, so that essentially no part of the rotor is submerged in liquid.

Another device comprises a surgical instrument having a distal end adapted to perform a surgical procedure on a patient and a proximal end adapted to be controllable by an operator. The instrument includes a pressure lumen having sufficient burst strength to conduct a high pressure liquid towards the distal end of the instrument. The pressure lumen includes at least one nozzle providing a jet opening. The nozzle is shaped to form a liquid cutting jet as a liquid at high pressure flows therethrough. The instrument further includes a rotatable shaft and a surgical component that is drivable by the shaft and is constructed and arranged for contact with tissue in a surgical operating field.

Yet another device comprises a surgical instrument having a distal end adapted to perform a surgical procedure on a patient and a proximal end adapted to be controllable by an operator. The instrument includes a rotatable shaft and a surgical component that is drivable by the shaft and constructed and arranged for contact with tissue in a surgical operating field. The instrument further includes a rotatable rotor that is drivingly coupled to the rotatable shaft, when the instrument is in operation, such that rotation of the rotatable rotor causes a corresponding rotation of the rotatable shaft. The instrument further includes a pressure lumen having a proximal end, and a distal end. The pressure lumen has a sufficient burst strength to conduct a high pressure liquid. The distal end of the pressure lumen includes a nozzle therein that is shaped to form a liquid jet as a liquid at high pressure flows therethrough. The nozzle is positioned so that at least a portion of the liquid jet emanating therefrom impacts a surface of a rotatable rotor, thereby imparting rotational motion to the rotor, such that there is essentially no change in hydrostatic pressure of the liquid comprising the liquid jet while in contact with the rotor.

Another device comprises a surgical instrument having a distal end adapted to perform a surgical procedure on a patient and a proximal end adapted to be controllable by an operator. The instrument includes a rotatable shaft having a longitudinal axis defining an axis of rotation of the shaft. The instrument also includes a surgical component that is drivable by the shaft and is constructed and arranged for contact with tissue in a surgical operating field. The instrument further includes a liquid jet-driven rotatable rotor. The rotor is drivingly coupled to the rotatable shaft, when the instrument is in operation, such that rotation of the liquid jet-driven rotatable rotor causes a corresponding rotation of the rotatable shaft. The rotatable rotor is configured to rotate about an axis of rotation that is essentially perpendicular to the axis of rotation of the rotatable shaft.

Yet another device comprises a surgical instrument having a distal end adapted to perform a surgical procedure on a patient and a proximal end adapted to be controllable by an operator. The instrument includes a rotatable shaft having a longitudinal axis defining an axis of rotation of the shaft. The instrument also includes a surgical component that is drivable by the shaft and is constructed and arranged for contact with tissue in a surgical operating field. The instrument further includes a liquid jet-driven rotatable rotor, drivingly coupled to the rotatable shaft, when the instrument is in operation, such that rotation of the liquid jet-driven rotatable rotor causes a corresponding rotation of the rotatable shaft. The rotatable rotor is configured to rotate about an axis of rotation at a first rotational speed, and the rotatable shaft rotates about the longitudinal axis defining an axis of rotation of the shaft at a second rotational speed that is different from the first rotational speed.

Another device comprises a surgical instrument having a distal end adapted to perform a surgical procedure on a patient and a proximal end adapted to be controllable by an operator. The instrument includes a rotatable shaft and a surgical component that is drivable by the shaft and is constructed and arranged for contact with tissue in a surgical operating field. The instrument further includes a liquid jet-driven rotatable saw-tooth rotor. The saw-tooth rotor is drivingly coupled to the rotatable shaft, when the instrument is in operation, such that rotation of the liquid jet-driven rotatable saw-tooth rotor causes a corresponding rotation of the rotatable shaft.

In another aspect, a method for performing a surgical procedure is disclosed. The method comprises inserting a surgical instrument into a surgical field of a patient, creating a liquid cutting jet with the surgical instrument, cutting or ablating a first selected tissue of the patient with the liquid cutting jet, rotating a rotatable component of the surgical instrument, contacting a rotating surface of the rotatable component with a second selected tissue, and grinding, cutting, or ablating the second selected tissue with the rotating surface.

In yet another aspect, a pressure-tight sealing component is described. The pressure-tight sealing component comprises an element that is constructed and arranged to be slidably moveable within a cylinder. The element is positionable on a shaft within the cylinder such that the element moves within the cylinder upon motion of the shaft. The element is shaped to include an integral, flared sealing flange portion that is constructed and arranged to make sealing contact with an internal surface of the cylinder while preventing contact both between the cylinder and the shaft, and between the cylinder and any other portion of the element. The flared sealing flange portion of the element when in contact with the internal surface of the cylinder, provides a leak-tight seal at the point of contact between the flared sealing flange portion of the element and the internal surface of the cylinder. This seal is able to withstand a differential in pressure of at least 1,000 psi without leakage of fluid therethrough.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 11A is a schematic illustration of one embodiment of a configuration for providing evacuation for a surgical instrument;

FIG. 11B is a schematic illustration of another embodiment for providing evacuation for a surgical instrument;

FIG. 13 is a schematic, cross-sectional illustration of the pressure-tight sealing component and spacer component of the liquid flow directing valve as in FIG. 12;

DETAILED DESCRIPTION

Figure 1:
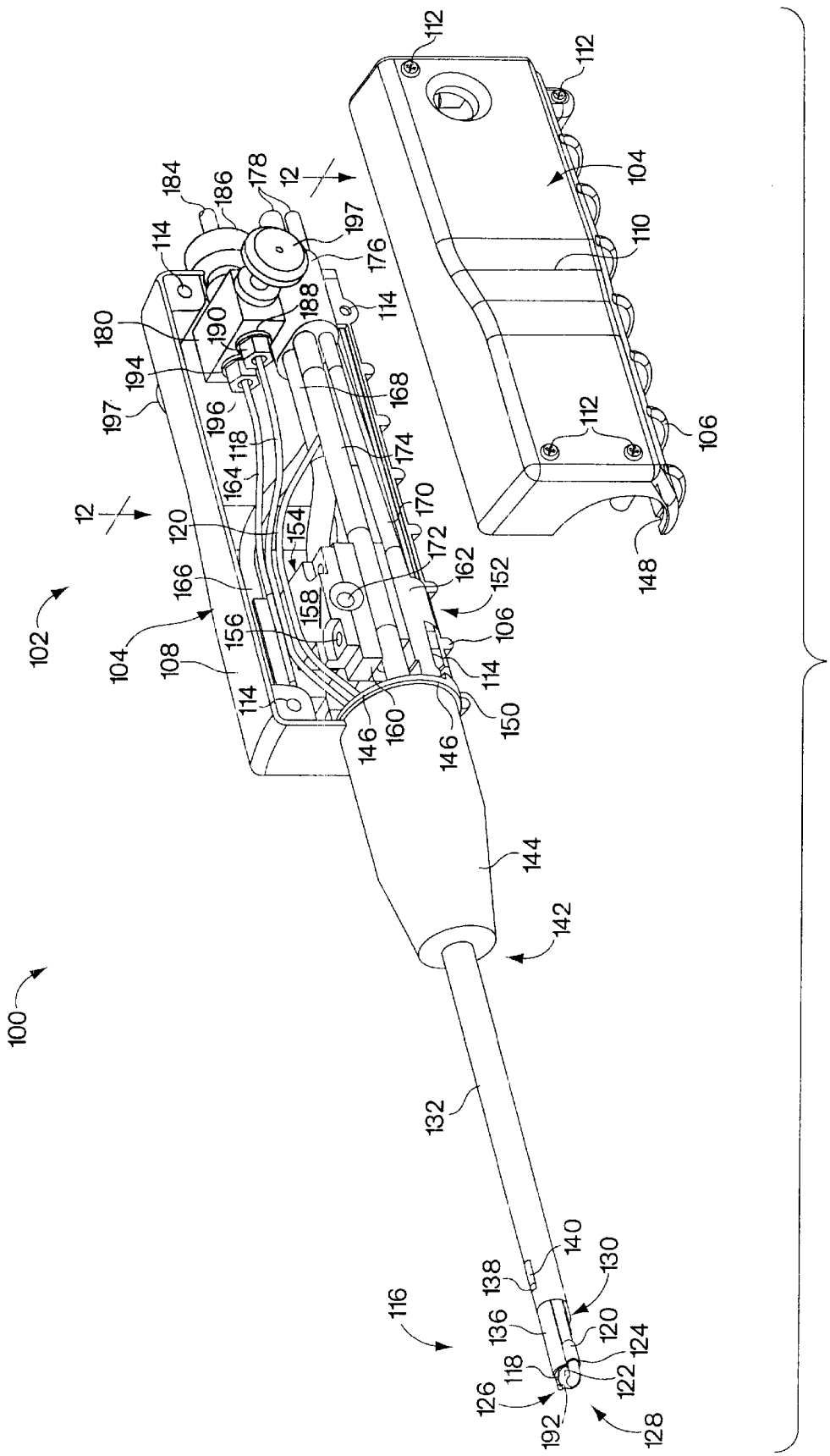
FIG. 1 is a schematic, perspective illustration of a surgical liquid jet instrument providing a liquid cutting jet and a rotating burr at its distal end, with the body of the instrument disassembled to show the internal components thereof.

The present invention provides a variety of liquid jet instruments useful in a variety of applications, many of which instruments are especially well suited for performing a variety of surgical procedures. The liquid jet instruments provided by the invention can be configured in a variety of different ways for use in various surgical operating fields. Furthermore, the liquid jets created by the instruments can be used for a wide variety of purposes; for example, as liquid cutting jets to cut, ablate, sculpt, debride, delaminate, etc. various tissues of a human or animal body. The term "tissue" as used herein refers broadly to a component of a human or animal body, such components including but not limited to muscle, skin, cartilage, tendon, bone, tooth, brain, cardiac tissue, vessels, internal organs, tissue of the eye, etc.

The liquid jets may also be used to provide driving power to rotate rotatable shafts provided by instruments according to certain embodiments of the invention. The rotatable shafts of such instruments can be used for performing various surgical tasks, such as grinding, abrading, cutting, drilling, polishing, screwing, powering fastening tools, etc.

Certain preferred surgical instruments, provided according to the invention, are configured as surgical handpieces having a proximal end with a grasping region, or body, shaped and configured to be comfortably held in the hand of an operator. The instruments also have a distal end that includes at least one component constructed and arranged for contact with tissue. As discussed in more detail below, in certain embodiments, the above-mentioned component can comprise the distal end of a rotatable shaft, which may include, for example, a grinding burr, a cutting blade, a drill, a screwdriver, or other component.

In certain preferred embodiments, the instruments have a distal end that includes at least one nozzle for forming a liquid cutting jet. The distal end of the various inventive surgical instruments can be utilized, in certain preferred embodiments, to perform a surgical procedure on a patient. Although the surgical instruments described herein are shown as having a handpiece configuration, it should be understood that the invention is not strictly limited to surgical handpieces, and that the invention may also be practiced utilizing instruments including at least one liquid jet forming component but having a variety of alternative configurations and purposes. For example, instead of being configured as a surgical handpiece, the inventive surgical instruments could be configured for manipulation by machine control, such as a X/Y/Z positioning machine. Also, for embodiments involving instruments providing a liquid cutting jet at the distal end of the instrument, the liquid jet instrument can be used in a wide variety of surgical applications and utilize the high pressure liquid cutting jet to cut, drill, bore, perforate, strip, delaminate, liquefy, ablate, shape, form, etc. various tissues, organs, etc. of the body of a patient.

The liquid jet surgical instruments provided by the invention preferably include at least one pressure lumen that has a distal end terminating in at least one nozzle that provides a liquid jet opening, and that has a proximal end that is connectable so as to be in fluid communication with a source of liquid under high pressure, supplied, for example, by a high pressure pump or high pressure liquid dispenser. The liquid jet nozzle is shaped to form a liquid jet as a liquid under high pressure flows through the nozzle as described in greater detail below. The liquid jet, in certain embodiments, is used to create a driving force for rotating a rotatable shaft of the instrument that can extend, in preferred embodiments, from the body of the surgical instrument towards the distal end of the instrument. In some embodiments, the instrument includes a pressure lumen that conducts a high pressure liquid toward the distal end of the instrument and that includes at least one nozzle that creates a liquid cutting jet as a high pressure liquid flows therethrough. The liquid cutting jet, for embodiments wherein the surgical instrument provides a liquid cutting jet at its distal end, can be used to cut, ablate, sculpt, trim, form, debride, etc., various tissues of a patient in surgical procedures.

In some especially preferred embodiments, the surgical instruments provided by the invention include two pressure lumen, one for forming a liquid cutting jet at the distal end of the instrument and the other for forming at least one liquid jet utilized to drive the rotation of a rotatable shaft included in the surgical instrument. In some preferred embodiments, the liquid pressure supplied to the instrument by a high pressure pump or high pressure dispenser can be variably controllable by an operator of the instrument so that the cutting or ablating power of the liquid cutting jet, or the power supplied to rotate the rotatable shaft, is adjustable by the operator. This adjustability of the pressure can allow an operator to create a liquid cutting jet with the instrument that can differentiate between different types of tissue within a surgical operating field and/or can allow an operator to rotate a rotatable shaft of the instrument at varying rotational speeds with varying maximum achievable levels of torque according to the particular needs of the surgical procedure for which the distal end of the rotating shaft is being utilized.

For example, for embodiments including a liquid cutting jet provided at the distal end of the instrument, a lower pressure can be utilized for cutting or ablating a soft tissue, such as fat, from a surface of a harder tissue, such as muscle or bone, where the liquid jet has sufficient strength to cut or ablate the soft tissue without damaging the underlying harder tissue. A higher pressure can then be selected that is sufficient to form a liquid cutting jet capable of cutting or ablating hard tissue, such as muscle or bone. For embodiments including liquid jet-driven rotatable shafts, a relatively low pressure liquid can be utilized for embodiments wherein a relatively low rotational speed and/or low torque is required, for example for embodiments having a cutting blade disposed at the distal end of the rotatable shaft that is used for cutting or trimming relatively soft tissue, and a high pressure liquid may be utilized for surgical procedures where higher rotational speeds and/or maximum torques are required, for example for embodiments where a grinding burr comprises, or is connectable to, the distal end of the rotatable shaft and is used, for example, for grinding hard tissue such as bone. In this way, the liquid jet surgical instruments provided by the invention, can, in many embodiments, provide highly selective and controllable tissue cutting, ablating, grinding, etc., in various surgical procedures. In addition, as discussed in more detail below, for embodiments involving surgical instruments providing both a liquid cutting jet and a rotatable shaft for performing surgical procedures, a liquid flow directing valve may be included within the body of the surgical instrument. The valve can function to direct a high pressure liquid to the pressure lumen within the surgical instrument that is in fluid communication with the liquid cutting jet forming nozzle at the distal end of the instrument, to the pressure lumen that is in fluid communication with the nozzle forming a liquid jet configured to drive rotation of the rotatable shaft, or to both simultaneously.

Preferred embodiments of the inventive surgical instruments that are configured to provide a liquid cutting jet at their distal end also include a liquid jet target or dissipater that is locatable opposite the jet opening orifice in the nozzle from which the liquid cutting jet is emitted (hereinafter referred to the "liquid jet opening" or "jet opening") at a predetermined distance from the liquid jet opening in order to receive and/or dissipate energy of a liquid cutting jet, when the instrument is in operation. Embodiments including a target or dissipater are preferred because the target/dissipater prevents the liquid cutting jet from being misdirected during use and potentially causing damage to unintended tissue sites in the surgical operating field. The target/dissipater enables the instrument to provide a predetermined liquid cutting jet length defined by the predetermined distance between the liquid jet opening in the nozzle and the surface of the target/dissipater upon which the cutting jet impinges. With such embodiments, the liquid cutting jet can be utilized for performing surgical cutting or ablating of tissue with a reduced danger of causing unintended collateral damage to tissue lying beyond the target/dissipater in the surgical operating field.

In some embodiments, the target/dissipater can be simply a solid surface capable of dissipating the energy of a liquid cutting jet by transforming the liquid jet into a harmless spray. In more preferred embodiments, however, the target is defined by a jet-receiving opening included in an evacuation lumen that forms part of the surgical instrument. In the preferred embodiments of instruments including an evacuation lumen having a jet-receiving opening, in addition to providing a defined liquid jet length (defined by the predetermined distance between the liquid jet opening and the jet-receiving opening) and preventing unintended damage as discussed above, the evacuation lumen can also be utilized for removing liquid, ablated tissue, and debris from the surgical field. In some embodiments of surgical jet instruments having an evacuation lumen for receiving a liquid cutting jet according to the invention, an external source of suction, for example a vacuum pump or aspirator, can be provided in fluid communication with a proximal end of the evacuation lumen in order to provide the suction driving force required for evacuating material from the surgical field via the jet-receiving opening. In some preferred embodiments, however, the invention provides surgical instruments having an evacuation lumen that is shaped and positionable relative to the jet nozzle forming the liquid cutting jet (as will become apparent to those of ordinary skill in the art from the detailed description below) to enable evacuation of essentially all of the liquid comprising the liquid cutting jet as well as ablated tissue and debris from the surgical site without requiring an external source of suction. In some preferred embodiments, the evacuating force created by the liquid cutting jet being directed into the evacuation lumen is sufficient to evacuate material from the operating site to a drainage reservoir located at the proximal end of the evacuation lumen or an evacuation conduit connected to the proximal end of the evacuation lumen. In such embodiments, the liquid cutting jet and the evacuation lumen together act as an eductor pump, which utilizes the momentum and kinetic energy of the moving fluid of the liquid cutting jet to create an evacuating force capable of driving liquid, ablated material, and debris through the evacuation lumen and away from the surgical site.

As discussed in detail below, the invention teaches that the effectiveness of evacuation of material through the evacuation lumen without the use of an external source of suction (i.e., via eductor pump action) can be improved, in some instances, by designing certain inventive instruments to provide particular geometrical relationships between the components for forming the liquid cutting jet and the components for receiving the liquid cutting jet, relating, for example, the size of the jet-receiving opening in the evacuation lumen to the predetermined distance between the jet-receiving opening and the jet opening for forming the liquid cutting jet with the nozzle. Also, as taught by the invention, interrelated with the above-mentioned geometrical relationships for providing effective eductor pump action is the design of the liquid jet nozzle and the shape of the jet-receiving opening in the distal end of the evacuation lumen.

The liquid jet surgical instruments provided according to the invention may be utilized for performing surgical procedures, involving liquid cutting jets and/or rotatable tissue contacting surgical components, in a wide variety of surgical fields, including those comprising both liquid-filled and gaseous environments. As described below, certain of the inventive surgical instruments providing liquid cutting jets at their distal ends are especially well suited for performing surgical procedures in a liquid-filled surgical environment, where the distal end of the instrument, including, in some embodiments, the nozzle for forming the liquid cutting jet and the jet-receiving opening, are submerged in a liquid when the instrument is in operation. Such devices can be configured as surgical handpieces for use, for example, in endoscopic, arthroscopic, or other surgical procedures.

As is described herein, and in much greater detail in commonly owned co-pending U.S. patent application Ser. No. 09/313,679, entitled FLUID JET SURGICAL INSTRUMENTS, incorporated herein by reference, the inventive surgical liquid jet instruments that provide a liquid cutting jet at their distal end, can be configured to effectively remove material from the surgical site and transport the material through an evacuation lumen without the need for an external source of suction for a wide variety of angular orientations between the central region of the liquid cutting jet and the longitudinal axis of the evacuation lumen. The term "central region of the liquid jet" as used herein refers to a region defining a geometric center of the liquid jet. This region is typically an essentially cylindrical region of the liquid jet confined within a cylinder whose outer surfaces are shaped and whose perimeter is defined by the inner circumference of the liquid jet opening in the nozzle, which circumference is projected from the liquid jet opening to the jet-receiving opening along an axis that is colinear with the longitudinal axis of the jet nozzle. The "longitudinal axis" of the jet nozzle, as will be described in more detail below, is defined by the axial center line of the nozzle region of the pressure lumen. The "longitudinal axis" of the evacuation lumen refers to an axis defining the geometric center of the evacuation lumen in a region that is proximal to the jet-receiving opening. As used herein in the context of describing geometric relationships between longitudinal axes of various components, the term "co-linear" refers to components whose longitudinal axes are superimposed on essentially the same line and space. The term "parallel" when used in the same context refers to longitudinal axes that are not necessarily co-linear, but that are oriented in an essentially identical direction in space. Accordingly, surgical instruments provided according to certain embodiments of the invention enable effective evacuation of material and debris from the surgical site via a liquid cutting jet evacuation lumen, without the need for an external source of vacuum connected in fluid communication with such lumen, for a wide variety of liquid cutting jet angular configurations, including instruments providing liquid cutting jets that are directed axially, transversely, or at any angle between 0 and 180° with respect to a longitudinal axis defining the proximal end or body of the surgical instrument.

For embodiments involving surgical instruments including an evacuation lumen for receiving a liquid cutting jet, plugging of the evacuation lumen can be prevented by constructing the evacuation lumen receiving the liquid cutting jet to have a region that is within and/or downstream of the jet-receiving opening that is designed to be able to macerate at least a portion of the tissue trained by the liquid jet into a plurality of particles when the instrument is in operation. The term "macerate" as used herein refers to a disaggregation of entrained material, for example an entrained tissue, by a liquid within the evacuation lumen undergoing intensely turbulent flow that creates a region of extremely high fluid shear and impacting forces capable of partitioning the material into particles having a size small enough to pass through the evacuation lumen without plugging the lumen. In preferred embodiments, the evacuation lumen is able to macerate a substantial fraction of the tissue entrained into a plurality of essentially microscopic particles. "Microscopic" as used herein refers to particles having a dimension too small to be visualized unaided by the human eye.

Prevention of blow-by (defined as a portion of a liquid cutting jet or high velocity fluid entrained by the liquid cutting jet having a cross-sectional area, at the plane of the jet-receiving opening, that is larger than the cross-sectional area of the jet-receiving opening so that at least a portion of the liquid cutting jet or high velocity fluid misses or "blows by" the jet-receiving opening) can be accomplished by providing a surgical jet instrument having a distal end configured so that, when in operation, the liquid cutting jet and the high velocity fluid entrained by the liquid cutting jet occupies a substantial fraction of the cross-sectional area of the jet-receiving opening, but does not occupy a region larger than the cross-sectional area of the jet-receiving opening. As discussed in more detail below, this "substantial fraction" refers to at least 50%, but less than 100% of the cross-sectional area of the jet-receiving opening being occupied by an entrainment region created by the liquid cutting jet.

As discussed above, certain embodiments of the surgical instruments provided according to the invention include a rotatable shaft, which, in some preferred embodiments, extends from the body of the instrument, or from the proximal end of the instrument, towards the distal end of the instrument. The rotatable shafts provided according to the invention can have distal ends comprising, or reversibly connectable to, a surgical component that is constructed and arranged for contact with tissue in a surgical operating field. The "distal end" of the rotating shaft as used herein refers to a portion of the rotating shaft located at the distal end of the instrument and within a surgical operating field when the instrument is in operation. It should be emphasized that the distal end of the rotatable shaft can include, in some embodiments, regions proximal to the extreme distal tip of the rotatable shaft that are still within the surgical operating field when the instrument is in operation.

Components constructed and arranged for contact with tissue can be components that are comprised by the distal end of the rotatable shaft itself or, alternatively, can be components that are removably attachable/connectable to the distal end of the rotatable shaft. Such components may, as apparent to those of ordinary skill in the art, be provided in a wide variety of forms for performing a wide variety of functions useful in various surgical procedures. For example, in some embodiments, the component can be constructed and arranged to cut, grind, ablate, shape, drill, bore, pulverize, polish, liquefy, screw, etc., a tissue within the operating field. In addition, as described in more detail below, the rotatable shaft can be permanently, or semi-permanently, contained within the surgical instrument or, alternatively and more preferably, can be configured to be removable and exchangeable with other rotatable shafts, for example those having different components at their distal ends for performing different surgical functions. It is also contemplated that the rotatable shaft can be configured within the surgical instrument so that its distal end, including the component constructed and arranged for contact with tissue, is selectively retractable so that, under control of an operator, the distal end of the rotatable shaft may be selectively deployed into the surgical operating field for performing a surgical procedure and, when the procedure is completed, retracted into the instrument and away from the surgical field. Such a retractable configuration can be especially useful for instruments including both a rotatable shaft and a liquid cutting jet at the distal end of the instrument, wherein during a surgical procedure requiring the rotatable shaft, the shaft may be deployed into the surgical operating field, but during a procedure requiring use of only the liquid cutting jet, the rotatable shaft may be withdrawn from the surgical field, if desired.

For instruments provided according to the invention including a rotatable shaft therein, the proximal end of the rotatable shaft is typically disposed within a body or at a user-controllable proximal end of the instrument. The proximal end of the shaft is drivingly coupled to a mechanism that is constructed and arranged to impart a rotating motion to the rotatable shaft. The term "drivingly coupled" as used herein refers to the shaft being interconnected with a drive mechanism such that motion of a component of the drive mechanism imparts rotational motion to the rotatable shaft. Such coupling can be accomplished, as would be apparent to those of ordinary skill in the art, by a variety of means such as, but not limited to, gear drives, belt drives, chain drives, friction drives, etc. The drive mechanism utilized to rotate the rotatable shaft within the instrument can comprise one or more of a variety of drive mechanisms including, but not limited to, electric motors, pneumatic turbines, etc., as apparent to those of ordinary skill in the art. However, in preferred embodiments, the invention utilizes an inventive liquid jet-driven rotatable rotor, preferably positioned within the body or at the proximal end of the instrument, to impart rotational motion to the rotatable shaft.

Preferred embodiments of the liquid jet-driven rotatable rotor mechanism provided according to the invention utilize a pressure lumen, having a liquid jet forming nozzle at a distal end thereof, to direct a liquid jet so that it impacts an impacting surface on the rotatable rotor, thus driving rotation of the rotor, which, in turn, creates a corresponding rotation of the rotatable shaft that is drivingly coupled thereto. Unlike typical prior art fluid driven turbine mechanisms, the preferred shaft-drive mechanism provided according to the invention does not utilize an expanding gas or, as is the case with typical prior art liquid-driven turbines, confine the rotor and liquid flow path within in an enclosed duct or channel such that the rotor is essentially completely submerged in a liquid during its rotation. In such typical prior art "reaction" turbines, the liquid driving the rotor undergoes a substantial change in hydrostatic pressure while in contact with the driving surface of the rotor. In contrast, the liquid jet-driven rotatable rotor mechanism provided according to the invention preferably maintains the liquid jet-driven rotor within a surrounding gaseous environment while it is being rotatably driven by a liquid jet during operation, so that essentially no part of the rotor is submerged in liquid during operation. In other words, the liquid that is in contact with the rotatable rotor, according to the invention, is essentially limited to a region of the liquid jet contacting a jet impacting surface of the rotatable rotor. As described in more detail below, the mechanism functions by directing an essentially collimated liquid jet, from a jet opening in the nozzle of the pressure lumen, across a gas filled gap so that it impacts a surface of the rotor, imparting rotational motion thereto. While in the embodiments illustrated below a single liquid jet is directed so that it impacts an impacting surface on a rotatable rotor, thus driving rotation of the rotor, in other embodiments, multiple nozzles in the pressure lumen and/or multiple pressure lumen may be utilized to direct multiple liquid jets at one or more impacting surfaces of a single or multiple rotatable rotors within the instrument for driving the rotatable shaft, or, alternatively, for driving multiple rotatable shafts.

In some preferred embodiments, the rotatable rotor is contained within a housing within the body of the instrument, which housing is evacuated to remove any accumulated liquid therein so that the rotatable rotor remains essentially unsubmerged in a surrounding liquid during operation. In especially preferred embodiments, described in more detail below, an evacuation lumen including a jet-receiving opening therein is positioned opposite the jet opening in the nozzle of the rotor-driving pressure lumen and downstream of the impacting surface of the rotatable rotor so that it receives and evacuates the liquid comprising the rotor-driving liquid jet. Similarly to the evacuation lumen utilized for receiving and evacuating liquid cutting jets described above, the evacuation lumen utilized for receiving and evacuating the rotor-driving liquid jet can, in some embodiments, be placed in fluid communication with an external source of suction or can, in more preferred embodiments, be configured to enable evacuation of essentially all of the liquid comprising the liquid rotor-driving jet without the need for an external source of suction connected thereto. Except as specifically described below, the configurations useful for the nozzle and evacuation lumen utilized in the inventive rotor-driving mechanism can be similar to those described below for forming and evacuating a liquid cutting jet.

The preferred liquid jet-driven rotatable rotor described above utilizes primarily the impulse force resulting from a change in the momentum of the liquid jet, upon contact with an impacting surface of the rotor, to impart rotational motion to the rotor. In the inventive configuration, liquid leaves the nozzle of the pressure lumen as a jet having a free-surface, at the jet opening, in the surrounding gaseous environment. In such configuration, essentially the entire pressure drop of the liquid comprising the jet to atmospheric pressure takes place within the nozzle. By contrast, typical prior art fluid-driven drive mechanisms for use in surgical devices employ a turbine-driving fluid stream that is confined within a channel and utilize the acceleration of the fluid, while it is in contact with a turbine or rotor, characterized by a change in the hydrostatic pressure of the fluid while in contact with the turbine/rotor, to drive rotation of the turbine/rotor. The present inventors have determined that the preferred liquid jet-driven rotor mechanism provided according to the invention can, under certain conditions, provide improved efficiency of operation as well as improved torque vs. load characteristics, as compared with prior art mechanisms.

Also, as described in more detail below, for many embodiments of the invention, it is often desirable to provide a mechanism for drivingly coupling a liquid jet-driven rotor to a rotatable shaft of a surgical instrument so that the rotational speed of the rotatable shaft is different from that of the rotational speed of the liquid jet-driven rotor. Such rotational speed-changing drive mechanisms are well know to those of ordinary skill in the art. In the context of the present invention, a preferred drive coupling mechanism utilizes a gear reduction drive. The gear reduction drives utilized according to the invention can be configured in a variety of forms as apparent to those of ordinary skill in the art, including, but not limited to, screws and worm gears, helical gears, spur gears, etc. Some preferred embodiments of the invention utilize a gear reduction drive coupling mechanism providing a rotational speed of the rotatable shaft that is a defined fraction of the rotational speed of the liquid jet-driven rotatable rotor. By utilizing such a gear reduction mechanism, the maximum torque obtainable at the distal end of the rotatable shaft for rotating a tissue contacting surgical component, such as a grinding burr, can be larger, by a factor of the degree of gear reduction, than the torque that would be obtainable utilizing a direct drive coupling mechanism with the same diameter rotatable rotor. This can enable the use of a smaller diameter rotatable rotor for obtaining a particular value of maximum torque under maximum load conditions (i.e., when the rotatable shaft is completely stalled so that its rotational speed is essentially zero). As will be discussed in more detail below, a particularly advantageous configuration of a driving mechanism for providing rotary motion to the rotatable shaft, according to the invention, utilizes a liquid jet-driven rotatable rotor that rotates about an axis of rotation that is essentially perpendicular to the axis of rotation of the rotatable shaft (defined by the longitudinal axis of the shaft) of the surgical instrument. This configuration provides a compact and effective means for coupling rotation of the rotatable rotor to the rotatable shaft through the gear reduction mechanism.

The inventive surgical instruments will now be described in more detail in the context of several specific embodiments illustrated in the appended figures. It is to be understood that the embodiments described are for illustrative purposes only and that the novel features of the invention, as described in the appended claims can be practiced in other ways or utilized for instruments having other configurations, as apparent to those of ordinary skill in the art.

FIG. 1 shows one embodiment of a surgical instrument 100, provided according to the invention. Surgical instrument 100 illustrated is configured as a surgical handpiece having a proximal end 102 including a body 104 having grasping regions 106 configured for placement in the hand of an operator of the instrument. Body 104 as shown can be formed, in preferred embodiments, from a rigid plastic material, and is preferably configured so that it can be separated into adjoining sections so that components disposed within the body may be accessible. In the illustrated embodiment, body 104 comprises two halves 108, 110 joined together by means of screws 112 which mate with threaded bores 114. It should be understood that a variety of other means of joining the sections of the housing together can be utilized, as apparent to those of ordinary skill in the art, for example, such means including but not limited to, ultrasound welding, snap fitting, solvent welding, etc.

Surgical instrument 100 has a distal end 116 including a pressure lumen 118 and an evacuation lumen 120. Distal end 116 of instrument 100 further includes a rotatable grinding burr 122 disposed at the distal end of a rotatable shaft 124 (seen more clearly in FIG. 2A). "Distal end" when used herein in the context of a region of a surgical instrument refers to a portion of a surgical instrument that is adapted to perform a surgical procedure on a patient and which is inserted into a surgical field during operation of the instrument. The distal end 116 of instrument 100 can, in some embodiments, comprise only the distal ends 126, 128 of pressure lumen 118 and evacuation lumen 120 respectively as well as the distal end 130 of rotatable shaft 124 (see FIG. 2A) including grinding burr 122. In other embodiments, distal end 116 of instrument 100 can also include components proximal to the distal ends of the pressure lumen, evacuation lumen, and rotatable shaft that are also inserted into a surgical operating field of a patient during operation of the instrument. In addition, in other embodiments, not shown, the instrument may provide only a rotatable shaft and may not include a pressure lumen and an evacuation lumen at the distal end of the instrument. In yet other embodiments, the instrument may not include a rotatable shaft and grinding burr as shown but may instead include only a pressure lumen at the distal end of the instrument or, in other embodiments, a pressure lumen together with a target or evacuation lumen positioned opposite the pressure lumen to receive a liquid cutting jet.

In the illustrated embodiment, surgical instrument 100 further includes a sheath 132 which at least partially surrounds pressure lumen 118, evacuation lumen 120, and rotatable shaft 124. As explained in more detail below, sheath 132 aids in supplying support for the lumen to assist in maintaining and/or establishing a desired geometric configuration between pressure lumen 118 and evacuation lumen 120 to prevent relative motion of the lumen and misdirection of a liquid cutting jet. In addition, sheath 132 can be used for providing support and evacuation to distal end 130 of rotatable shaft 124. As discussed in more detail below in the context of FIGS. 2A–2C, removably coupled to distal end 116 and sheath 132 is burr tip support 136 including a snap tab 138 which fits into snap-lock slot 140 on sheath 132 to enable removable coupling thereto. Burr tip support 136 also serves to provide a bearing surface for distal end 130 of rotatable shaft 124, as well as to provide support to pressure lumen 118 and evacuation lumen 120.

Proximal end 142 of sheath 132 is sealingly coupled to the distal end of collar 144, whose function will be more thoroughly explained in the context of FIG. 4 below. Collar 144 includes a seating flange 146 which is held in place by slots 148 in body 104 when the instrument is assembled. Flange 146 also includes projecting ridge 150 which mounts within a complementary groove within body 104, in order to prevent collar 144 from rotating during operation of the instrument.

Contained within body 104 of instrument 100 is driving mechanism 152 configured for driving rotatable shaft 124. The specific details of the structure and operation of driving mechanism 152 are described in more detail below in the context of FIGS. 8A–8E. Drive mechanism 152 includes a liquid jet-driven rotor and gear reduction mechanism, shown and described in more detail below, enclosed in a three-part rotor housing 154 held together by screw fasteners 156 and comprising an upper rotor housing cap 158, a rotor housing block 160, and a rotor housing bottom component 162. High pressure liquid is supplied to drive mechanism 152 via rotor drive pressure lumen 164. Rotor housing 154 is evacuated of liquid via rotor jet evacuation lumen 166, rotor housing block evacuation conduit 168, and rotor housing bottom evacuation conduit 170. Also visible in FIG. 1 is rotor bearing 172. Bearings for use in the current invention for rotatably mounting a rotor or components of drive mechanism 152 coupled to rotatable shaft 124 can comprise any suitable type of bearing known in the art, for example ball bearings, journal bearings, or hydrodynamic bearings. In the illustrated embodiment, the bearings comprise ball bearings.

Also contained within body 104 is rotatable shaft evacuation conduit 174 for providing evacuation to sheath 132 surrounding the rotatable shaft and disposed in proximity to grinding burr 122. Body 104 also includes an evacuation conduit connecting block 176, which serves to couple the evacuation conduits (168, 170, and 174) and evacuation lumen 120 and 166 to evacuation tubing 178 exiting the proximal end of the instrument. Connecting block 176 can include any one of a variety of low pressure tubing connectors known to those of ordinary skill in the art, such as barbed connectors, Leur-lock connectors, press-fit connections, etc.

In the illustrated embodiment, including both a pressure lumen 118 for forming a liquid cutting jet at the distal end 116 of the instrument and a pressure lumen 164 for forming a liquid jet that provides rotational driving force to a rotatable shaft, a liquid flow directing valve 180 may be included. The structure and function of liquid flow directing valve 180 is described in greater detail below in the context of FIG. 12. Liquid flow directing valve 180 has an inlet 182 coupled to high pressure liquid supply conduit 184 by means of a manually tightenable high pressure tubing coupling 186. Valve 180 also includes a first outlet 188 that is coupled via high pressure connector 190 to pressure lumen 118 supplying high pressure liquid to nozzle 192 disposed at distal end 116 of the instrument for forming a liquid cutting jet. Valve 180 also includes a second outlet 194 coupled via high pressure connector 196 to pressure lumen 164 supplying high pressure liquid to rotatable shaft drive mechanism 152. Liquid flow directing valve 180 can be manually adjusted by an operator, via sliding motion of knobs 197, which are coupled to a shaft 198 (see FIG. 12), to enable liquid supplied via conduit 184 to be directed to either pressure lumen 118 or pressure lumen 164, depending upon the position of knobs 197, or to be directed to both pressure lumens simultaneously.

High pressure connectors 186, 190, and 196 may comprise any type of suitable high pressure connection known to those of ordinary skill in the art that is capable of withstanding, for example, pressures in excess of 1,000 psig, and preferably is capable of withstanding pressures up to at least about 50,000 psig. Such connectors may comprise welded/brazed fittings, flanged fittings, swaged fittings, etc., as apparent to those of ordinary skill in the art. In a preferred embodiment, as illustrated, the high pressure fittings utilized include highly compressed elastomeric O-rings and are configured as described in commonly owned U.S. Pat. No. 5,713,878, incorporated herein by reference.

Figure 2A:
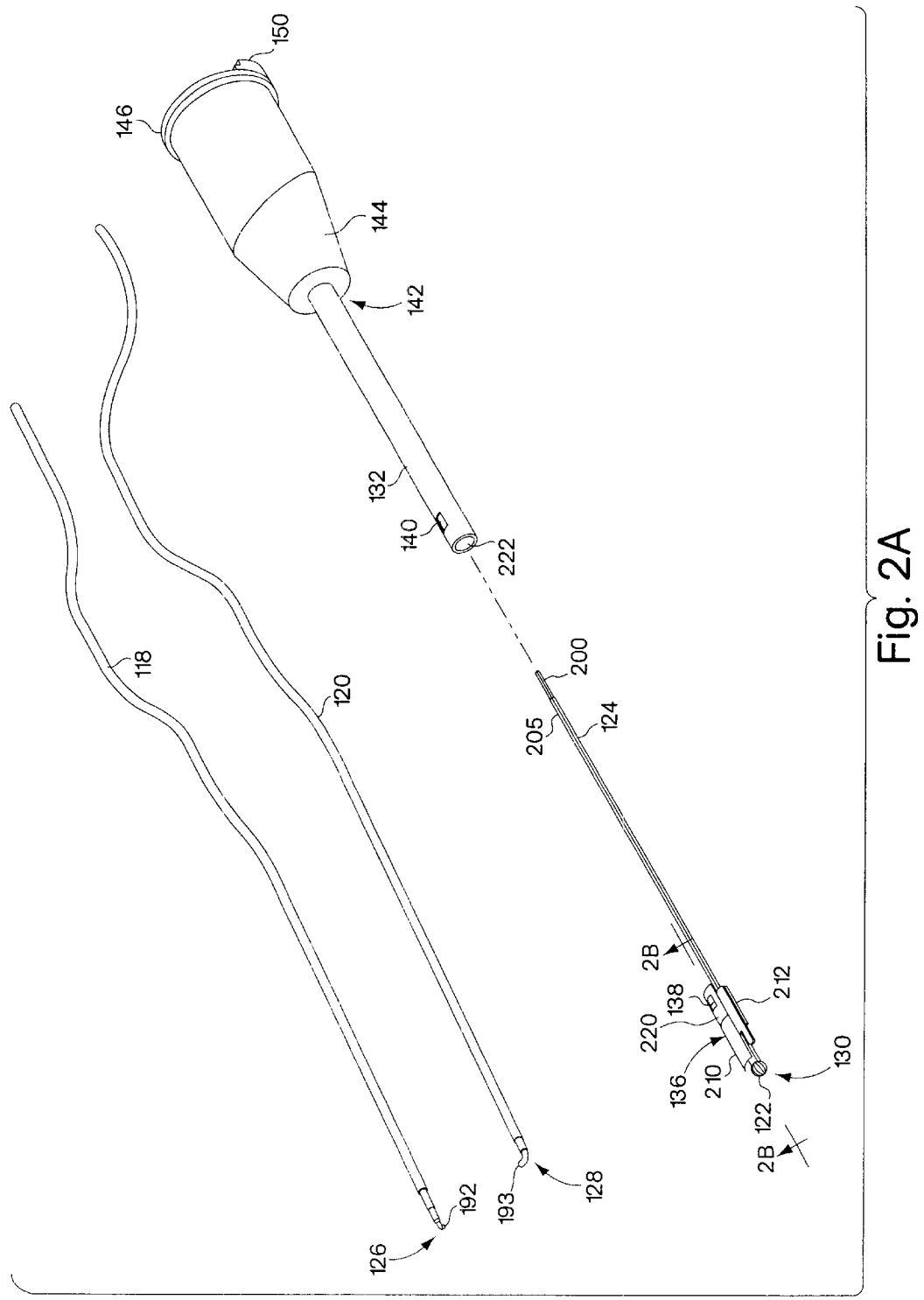
FIG. 2A is a schematic, exploded, perspective illustration of a portion of the surgical instrument as in FIG. 1 showing the sheath and collar and components contained therein.
Figure 2B:
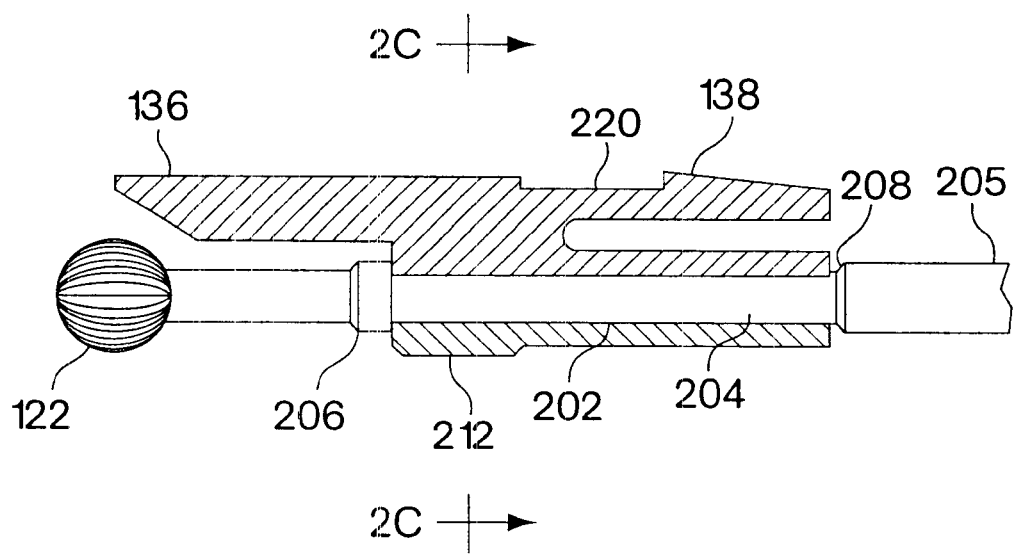
FIG. 2B is a schematic, cross-sectional illustration of the distal end of the surgical instrument as in FIG. 2A showing the distal end of the rotatable shaft and the support element therefor.

FIG. 2A is an exploded perspective view of the portions of surgical instrument 100 disposed distal to body 104. As illustrated in FIG. 2A, rotatable shaft 124, pressure lumen 118 and evacuation lumen 120 are shown removed from sheath 132 for clarity. Pressure lumen 118 and evacuation lumen 120 are preferably constructed from a surgical grade stainless steel, however, in alternative embodiments, either or both of the lumen may be constructed from other suitable materials, for example certain polymeric materials, as apparent to those of ordinary skill in the art. Regardless of the specific material from which the pressure lumen is constructed, pressure lumen 118 (as well as pressure lumen 164 supplying drive mechanism 152) must have sufficient burst strength to enable the lumen to conduct a high pressure liquid to the nozzle, for example nozzle 192, at the distal end of the pressure lumen in order to form a liquid jet. The burst strength of the pressure lumen utilized in the surgical instrument should be selected to meet and preferably exceed the highest contemplated pressure required for use in the specific surgical procedure to be performed. Typically, surgical instrument 100 will operate at liquid pressures of between about 500 psig and about 50,000 psig, depending on the intended material to be cut and/or ablated and/or the required rotational speed and maximum torque of the rotatable shaft. Those of ordinary skill in the art will readily be able to select appropriate materials for forming the pressure lumen of the instrument and the evacuation lumen for particular surgical requirements based on the functional requirements of each described herein.

Also illustrated in FIG. 2A is a preferred configuration for supporting rotatable shaft 124 and lumens 118 and 120 within sheath 132. Rotatable shaft 124 includes a coupling region 200, having a reduced cross-sectional area and a non-circular cross sectional shape, disposed at its proximal end. Coupling region 200, as described in more detail below, enables rotatable shaft 124 to be coupled in driving engagement with shaft drive mechanism 152. Supporting the distal end 130 of rotatable shaft 124 is burr tip support 136. Shown in more detail in FIG. 2B and FIG. 2C, burr tip support 136, when assembled, provides a central shaft bearing region 202 surrounding a region 204 of rotatable shaft 124 having a circular cross sectional shape and a reduced cross sectional dimension when compared to the central region 205 of rotatable shaft 124. Region 204 is surrounded by shaft distal bearing region 202 of burr tip support 136 and rotates therewithin, when the instrument is in operation. Longitudinal movement of rotatable shaft 124 with respect to burr tip support 136 and sheath 132 is prevented by shaft bearing flange 206 and bearing lip 208 of rotatable shaft 124.

Figure 2C:
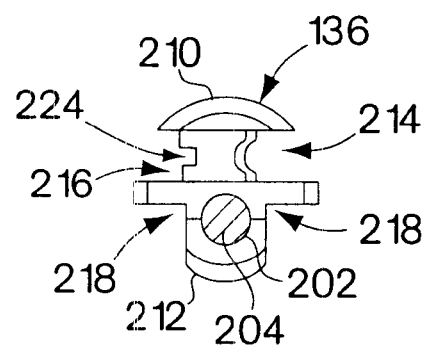
FIG. 2C is a schematic, cross-sectional illustration of the rotatable shaft and support element of the instrument as in FIG. 2B.

FIG. 2C shows a cross-sectional view of burr tip support 136 as viewed from the distal end of the instrument. Burr tip support 136 includes an upper support member 210 and a lower support member 212, which are separable one from the other when disassembled from sheath 132, and which, when coupled together, form shaft bearing channel 202. As shown in FIG. 2C, burr tip support 136 further includes an evacuation lumen slot 214 and a pressure lumen slot 216 for holding and supporting evacuation lumen 120 and pressure lumen 118 within sheath 132 respectively, when the instrument is assembled for use. Burr tip support 136 also includes evacuation channel slots 218 which, when the device is assembled, provide fluid communication, between the inside of sheath 132 and the region distal to burr tip support 136 within the surgical field, for evacuating tissue and debris surrounding grinding burr 122 from the surgical field and away from the patient. As discussed in more detail below, this evacuation may be provided by means of a source of external suction coupled in fluid communication with the proximal end of sheath 132 or, in alternative embodiments, may be generated by the rotation of rotatable shaft 124 itself.

Burr tip support 136 enables easy disassembly and exchange of rotatable shaft 124 and grinding burr 122. In this manner, a variety of grinding burrs, or other components for performing a surgical function on tissue of a patient can be interchanged during the course of a procedure or between surgical procedures. Replacement or exchange of a rotatable shaft/burr element can be performed as follows. While in an assembled configuration, for example as shown in FIG. 1, the user depresses snap tab 138 on the spring flange region 220 of burr tip support 136 and slides the burr tip support and rotatable shaft from bore 222 of sheath 132. Pressure lumen 118 and evacuation lumen 120 are rigidly connected at their proximal ends within body 104 of instrument 100 and remain within the sheath during removal of the rotatable shaft and burr tip support. While removing burr tip support 136 from sheath 132, the distal ends of pressure lumen 118 and 120 slide through pressure lumen slot 216, including a nozzle slot 224 therein, and evacuation lumen slot 214. Upon removal of burr tip support 136 and rotatable shaft 124, upper support member 210 and lower support member 212 can be separated, rotatable shaft 124 can be exchanged with another rotatable shaft having, for example, a different component at a distal end thereof, the upper support and lower support can be reassembled, and the burr tip support/rotatable shaft unit can be reinserted into bore 222 of sheath 132 until snap tab 138 snaps into snap lock slot 140 of the sheath, thus completing the exchange process. Those of ordinary skill in the art will readily envision a variety of alternative means for providing exchangeability of rotatable shaft 124 of instrument 100, all of which are deemed to be within the scope of the present invention.

Upon assembly, burr tip support 136, in addition to providing a distal bearing for rotatable shaft 124, also supplies support for pressure lumen 118 and evacuation lumen 120 to assist in maintaining and/or establishing a desired geometric configuration between the pressure lumen and the evacuation lumen when instrument 100 is in operation. In preferred embodiments, pressure lumen 118 and evacuation lumen 120 are supported by burr tip support 136, when the instrument is assembled, so that the distal ends of the lumen are sufficiently stiff to prevent deflection of the lumen, by, for example, contact with surfaces within the surgical operating space, which deflection could potentially lead to misdirection of the liquid cutting jet formed by nozzle 192 as high pressure liquid flows therethrough so that the cutting jet is no longer incident upon jet-receiving opening 193 in evacuation lumen 120, thus potentially causing unintended tissue damage to the patient.

Figure 3:
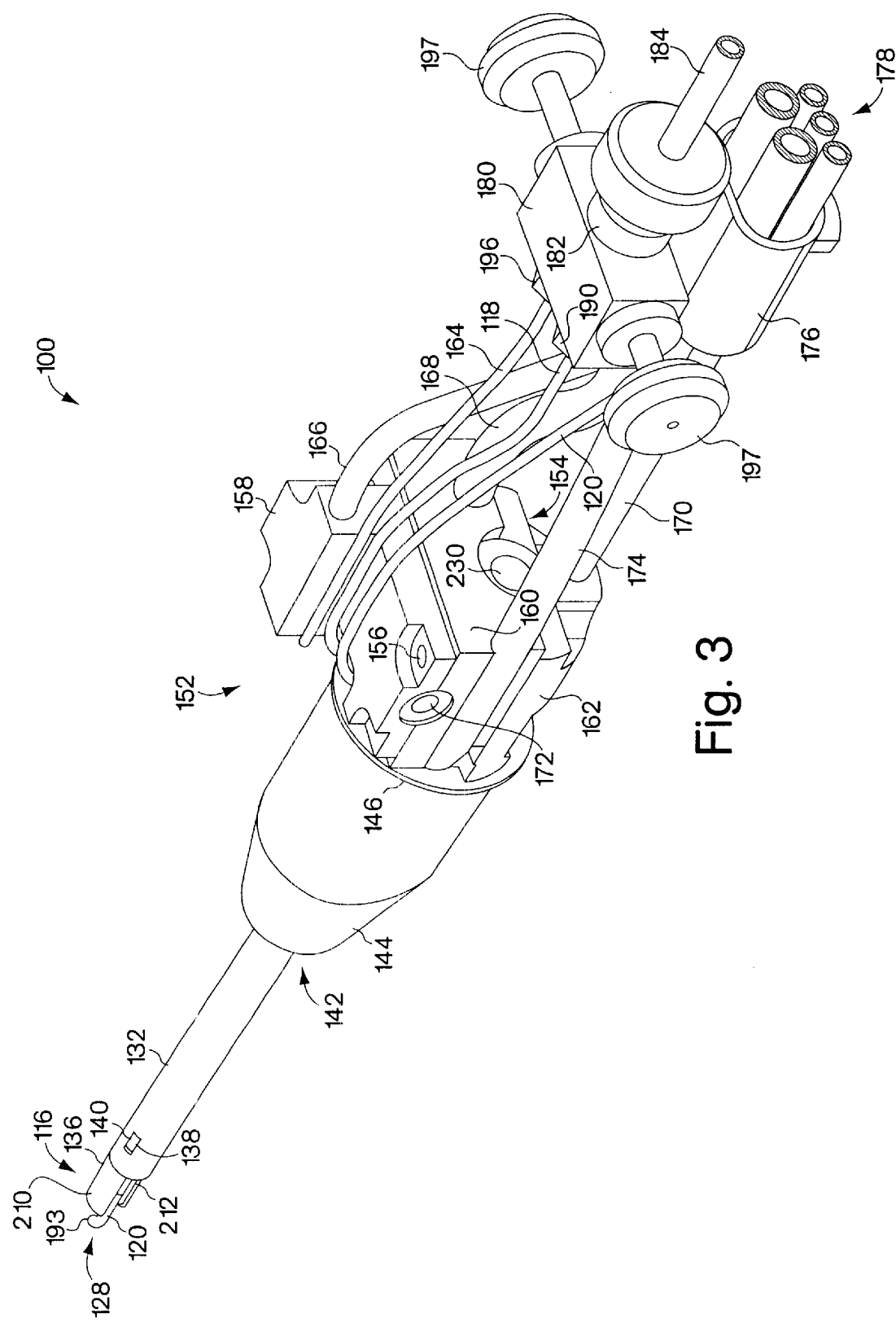
FIG. 3 is a schematic, perspective illustration of the surgical instrument as in FIG. 1, excluding the body of the instrument, and as viewed from the proximal end of the instrument.

FIG. 3 is a perspective view showing surgical instrument 100 as viewed from a proximal end thereof. FIG. 3 illustrates the assembled surgical instrument except excluding body 104 to show the internal components with greater clarity. The particular view illustrated shows more clearly the back view of shaft drive mechanism 152 showing shaft drive bearing 230 as well as the locations for attachment to rotor drive jet evacuation lumen 166, rotor housing block evacuation conduit 168, and rotor housing bottom evacuation conduit 170. Also shown more clearly is high pressure conduit 184 and evacuation conduits 178. High pressure liquid supply conduit 184 must have a burst strength capable of withstanding the highest liquid pressures contemplated for using instrument 100 for a particular surgical application. In some embodiments, high pressure liquid supply conduit 184 comprises a burst-resistant stainless steel hypotube constructed to withstand at least 50,000 psig. In some embodiments, the hypotube may be helically coiled to improve the flexibility and maneuverability of surgical instrument 100. In preferred embodiments, especially those including integrated electrocautery as discussed below, high pressure liquid supply conduit 184 is comprised of an electrically insulating material such as a Kevlar®-reinforced nylon tube. The liquid contained in evacuation conduits 178 (as well as evacuation conduits 168, 170, and 174 within the body of the instrument) is under relatively low pressure and, accordingly, the evacuation conduits may be constructed, in preferred embodiments, of a low cost flexible material, for example, polymeric tubing such as polyvinyl chloride (PVC), silicone, polyethylene, rubber, etc., tubing. Evacuation lumen 120 and at least the distal end (i.e. that contained within housing 154 and surrounding the rotor, as shown in FIGS. 8C–8E below) of evacuation lumen 166 are preferably constructed of a rigid material, such as stainless steel. In preferred embodiments, evacuation conduits 178 should have a minimum internal cross-sectional area that equals or exceeds the maximum internal cross-sectional area of the evacuation lumens and conduits within body 104 of instrument 100 to which the evacuation conduits are coupled in fluid communication.

Figure 4:
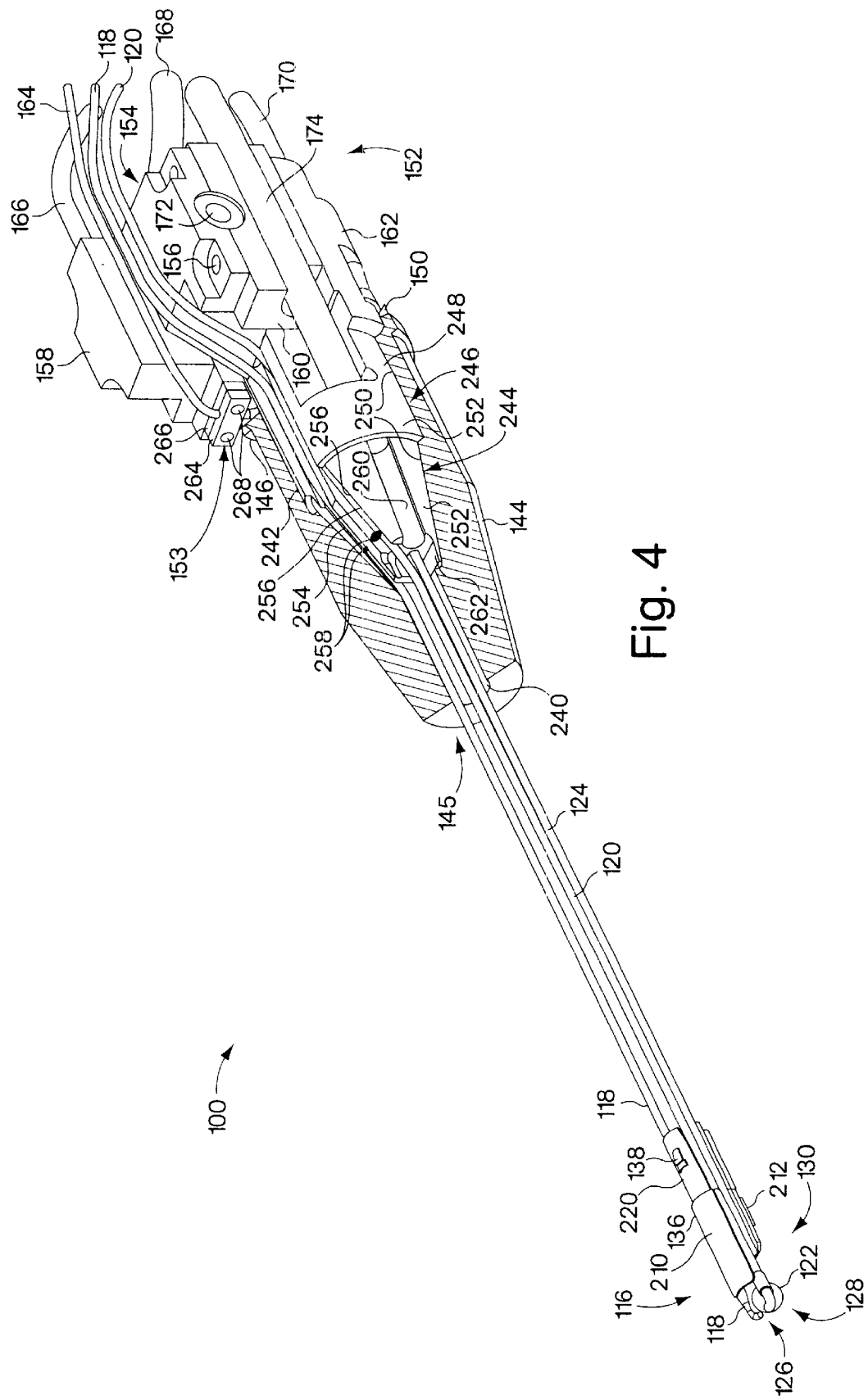
FIG. 4 is a schematic, partially-cutaway, perspective illustration of the surgical instrument as in FIG. 1, wherein the sheath component has been rendered transparent.

FIG. 4 is a perspective illustration showing surgical instrument 100 as viewed from its distal end 116. In FIG. 4, surgical instrument 100 is shown without sheath 132 or body 104 to more clearly illustrate the internal configuration of the collar 144 providing fluid communication between sheath 132 and shaft evacuation conduit 174, as well as to more clearly illustration of the distal side 153 of rotatable shaft drive unit 152.

Collar 144 is shown partially cutaway in FIG. 4. Collar 144 can be comprised of a metal, such as surgical stainless steel, or in more preferred embodiments, can be comprised of a rigid plastic, such as polycarbonate, nylon, acetal polymers, etc., as apparent to those of ordinary skill in the art. Collar 144 has a distal end 145 with a centrally disposed bore 240 therethrough surrounding pressure lumen 118, evacuation lumen 120 and rotatable shaft 124. Bore 240 is sized and configured so that proximal end 142 of sheath 132 can be press-fit therein to form a continuous, leak-tight path for fluid communication between shaft evacuation conduit 174 and evacuation channel slots 218 of burr tip support 136, when the instrument is assembled as shown in FIGS. 1 and 2A–2C. In the illustrated embodiment, evacuation is supplied to the distal end of the instrument surrounding grinding burr 122 by coupling shaft evacuation conduit 174 in fluid communication with a source of external suction, such as a suction pump or aspirator. As described below, in alternative embodiments, rotatable shaft 124 can be configured such that rotation of the shaft is able to impart a driving force for removing material from the region surrounding the grinding burr without requiring conduit 174 to be attached to the source of external suction.

Collar 144 further includes a centrally disposed cavity 242 therein having a distal region 244, which is conically tapered, and a proximal region 246, which is essentially cylindrical in shape. Distal end 248 of rotor housing base 162 is shaped to mate with inner sealing surfaces 250 of cavity 242 in collar 144, to create a vacuum-tight seal between surface 252 of the distal end of the bearing block and inner sealing surface 250 of the collar.

Distal end 248 of rotor housing base 162 includes grooves 254, 256 machined therein, which grooves form channels for passage of pressure lumen 118 and evacuation lumen 120 respectively. In order to prevent leakage of evacuated fluid and a loss of suction through grooves 254 and 256 during operation of the device, a bead of sealant 258 can be used to surround the lumen and create a vacuum-tight seal with inner sealing surface 250 of collar 144, upon assembly of the device. Such sealant can be comprised of a polymeric foam or RTV sealant, as would be apparent to those of ordinary skill in the art.

Proximal end 248 of rotor housing base 162 further includes a sheath evacuation channel 260 machined therein for providing a fluid flow path for transport of fluid and debris between cavity 262, comprising a sheath evacuation region, and evacuation conduit 174. During operation of the device, when a suction is applied to evacuation conduit 174, liquid and debris will flow into sheath 132 via evacuation channel slots 218 of burr tip support 136, then through bore 240 of collar 144 into sheath evacuation cavity 262, through sheath evacuation channel 260, and finally through evacuation conduit 174 for removal from the instrument.

Also shown in FIG. 4 are rotor jet pressure lumen mounting blocks 264, 266 which are utilized to mount rotor drive pressure lumen 164 to rotor housing block 160 via, for example, screws 268. As described in more detail below, the rotor jet pressure lumen mounting blocks enabled precise alignment and direction of the liquid jet formed by the nozzle of pressure lumen 164 onto an impacting surface of a rotor utilized for driving rotatable shaft 124, when the device is in operation.

Figure 5A:
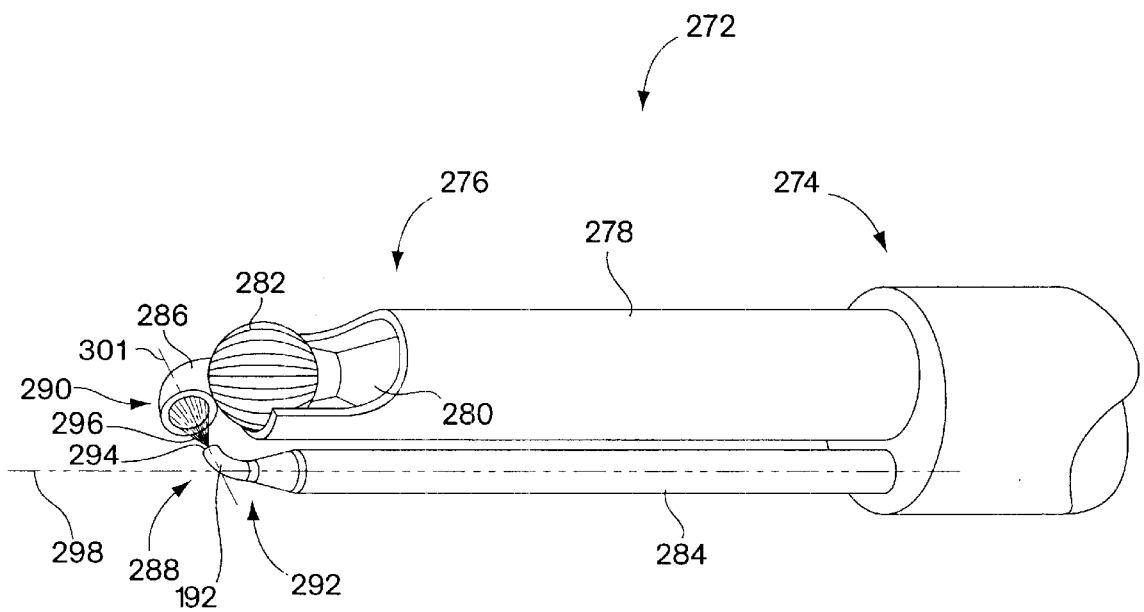
FIG. 5A is a schematic, perspective illustration of a portion of a surgical instrument showing an alternative embodiment for providing a distal end including a liquid cutting jet and a rotatable grinding burr.

FIG. 5A illustrates an alternative embodiment for configuring the distal end of a surgical instrument providing both a liquid cutting jet and a rotational grinding burr and also more clearly illustrates a preferred configuration for providing a liquid cutting jet nozzle and evacuation lumen distal end. Instrument 272 includes a proximal end 274 and a distal end 276. Unlike the previously illustrated embodiment, instrument 272 includes a sheath 278 surrounding only rotatable shaft 280 including, at its distal end, a grinding burr 282. Surgical instrument 272 further includes a pressure lumen 284 and an evacuation lumen 286, both of which are disposed external to sheath 278.

For embodiments of the invention utilizing rotating shafts including grinding burrs at their distal ends, a wide variety of grinding burrs can be utilized depending on the needs of the particular surgical application, as would be apparent to those of ordinary skill in the art. For example, fluted burrs and diamond burrs of various shapes and sizes can be used. For example, spherical, cylindrical, oval, flat, pear or egg shaped burrs may be utilized of various sizes for particular surgical applications. Typical burr sizes for use, for example, in bone grinding for arthroscopic procedures, can have an outer diameter ranging from about 2 mm to about 6 mm with the number of flutes, for fluted burrs, ranging from about 2 to about 20. In one particular example, involving the use of a grinding burr for bone grinding in arthroscopic procedures, a 5 mm outer diameter spherical, fluted burr having eight flutes is utilized.

Figure 5B:
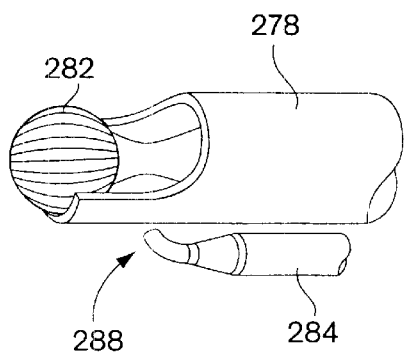
FIG. 5B is a schematic, perspective illustration of a portion of a surgical instrument showing another alternative embodiment for providing a distal end of a surgical instrument providing both a liquid cutting jet and a rotatable grinding burr.

In the configuration shown in FIG. 5A, distal tips 288 and 290 of pressure lumen 284 and evacuation lumen 286 respectively are disposed distally to grinding burr 282. In another embodiment shown in FIG. 5B, distal tips 288 and 290 may, alternatively, be disposed proximal to grinding burr 282.

Also shown in FIG. 5A is a preferred arrangement for forming nozzle 192 in a pressure lumen for creating a liquid jet, as well as a preferred configuration for the distal end 290 of the evacuation lumen of the surgical instrument configured to receive a liquid cutting jet. Pressure lumen 284, which is substantially identical in configuration to pressure lumen 118 discussed above, comprises a tubular conduit having a necked region 292 of the conduit defining nozzle 192, which necked region has an internal cross-sectional area that is less than an internal cross-sectional area of the tubular conduit outside of and proximal to necked region 292. The distal end of pressure lumen 284 is further configured to enable jet opening 294 to direct a liquid cutting jet 296 in a direction essentially transverse to the longitudinal axis 298 of pressure lumen 284. Specifically, nozzle region 292 is bent with respect to longitudinal axis 298 of pressure lumen 284 outside of jet nozzle region 292, so that jet opening 294 emits a liquid jet 296 whose central region is directed along an axis 300 that is essentially perpendicular to longitudinal axis 298. In alternative embodiments, the angle formed between jet axis 300 and longitudinal axis 298 can be any angle between about 0° and about 90° (as shown).

Nozzles provided according to the invention, both for forming liquid cutting jets and for forming liquid jets to drive rotational components of the instruments (as described in more detail below) preferably have a relatively large nozzle length to internal diameter ratio. The nozzles for use in inventive surgical instruments, both for forming liquid cutting jets and for driving rotational motion of a rotatable shaft, preferably have a region having a minimum internal diameter, which region has a length that exceeds its minimum internal diameter by at least a factor of about 2, more preferably by a factor of about 4, and even more preferably by at least a factor of about 6. In other embodiments, the region has a length that exceeds its minimum internal diameter by at least a factor of about 10. As will be discussed in more detail below, the greater the ratio of the length to minimum internal diameter of the nozzle region, the more narrowly focused and collimated will be the liquid jet that is emitted from the jet opening of the nozzle. For reasons described in more detail below, highly collimated liquid jets are preferred both for forming liquid cutting jets at the distal end of the inventive surgical instruments and for driving rotational motion of rotatable rotors and shafts provided by the inventive surgical instruments. However, in general, nozzles with ratios of length to minimum internal diameter that are very high, for example greater than about 10, tend to create a very high pressure drop through the nozzle during use without significantly improving the degree of collimation of the jet and, therefore, are less preferred for use in the inventive surgical instruments than nozzles having a ratio of length to minimum internal diameter of an intermediate value, for example about 6.

The present invention provides surgical liquid jet instruments which are specifically designed and constructed for use in a particular surgical environment. Specifically, certain embodiments of the invention provide surgical liquid jet instrument designs that are tailored to provide highly desirable liquid jet cutting characteristics in surgical operating environments where the liquid jet is submerged in a liquid environment when the instrument is in operation. More specifically, the invention provides, in such embodiments, surgical liquid jet instruments including pressure lumen and evacuation lumen that are shaped, and positioned relative to each other, to establish certain predetermined geometric relationships between the jet forming components and jet-receiving components that are specifically selected to provide the desired performance characteristics of the instrument in a liquid surgical environment.

Figure 6A:
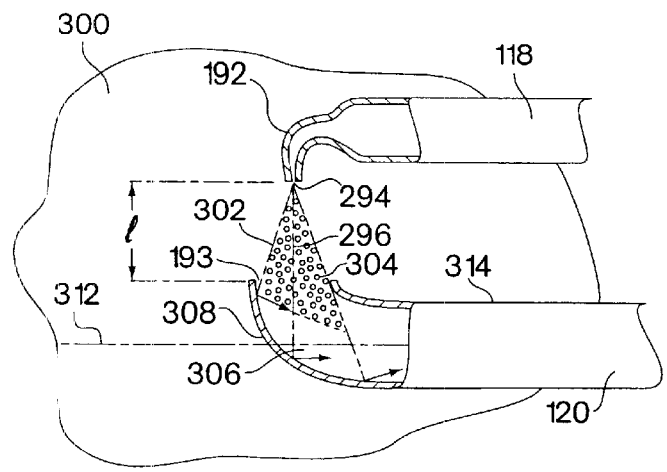
FIG. 6A is a partially-cutaway, schematic illustration of a portion of the distal end of a surgical liquid jet instrument for creating a liquid cutting jet in a surrounding liquid environment.

Reference is made in FIG. 6A for describing the operation and design characteristics of preferred devices for use in forming a liquid cutting jet that is submerged in a surrounding liquid-containing surgical environment. FIG. 6A shows a partially cutaway view of the distal ends of pressure lumen 118 and evacuation lumen 120, which can form part of a surgical instrument, for example such as that shown previously in FIG. 1. Prior to operation, the distal ends of pressure lumen 118 and evacuation lumen 120 would be inserted into the operating field and at least partially submersed in a liquid 300 therein so that at least nozzle 192 and jet-receiving opening 193 are completely surrounded by liquid 300. When the instrument is in operation, liquid under high pressure is delivered via pressure lumen 118 to nozzle 192, causing jet opening 294 to create a liquid cutting jet 296 as the high pressure liquid streams therethrough. As mentioned previously, it is preferred that the jet 296 is substantially collimated as it exits jet opening 294. The more collimated a liquid jet, the less the liquid jet will diverge or disperse as it traverses the gap between jet opening 294 and jet-receiving opening 193. Thus, a highly collimated jet will have a cross-sectional shape and area at the jet-receiving opening 193 that is substantially similar to the cross-sectional shape and area of the liquid jet at jet opening 294.

In general, the pressure of the high pressure liquid supplied to nozzle 192 for forming the liquid cutting jet 296 depends on the particular design of nozzle 192 and the hardness/toughness of tissue or material to be cut or ablated. Typically, the liquid at high pressure is supplied to jet opening 192 at a pressure of at least 500 psig, in other embodiments at a pressure of at least about 5,000 psig, and still other embodiments at a pressure of at least about 15,000 psig, and still other embodiments at a pressure of at least 30,000 psig, and in yet still other embodiments at a pressure of at least about 50,000 psig. Also as discussed previously, for embodiments where a collimated jet is desired, nozzle 192 preferably has a length to minimum internal diameter ratio of at least about four, more preferably at least about six, and in other embodiments at least about ten. Jet opening 294 typically has a circular cross-sectional area, but may, in other embodiments, have other cross-sectional shapes, such as rectangular, oval, slit-like, etc., for forming jets having different shapes for specific desired purposes. In preferred embodiments, jet opening 294 has an internal diameter of between about 0.001 and about 0.02 inches, more preferably between about 0.003 and about 0.01 inches, and most preferably about 0.005 inches.

Liquid cutting jet 296, which is collimated as it exits jet opening 294, tends to create a visible, opaque entrainment region 302 surrounding liquid cutting jet 296. Entrainment region 302 is comprised of rapidly moving liquid, which is entrained and driven by the kinetic energy of liquid cutting jet 296. Liquid cutting jet 296, as it rapidly moves through liquid environment 300, also tends to create a zone of low pressure, which is essentially coextensive with entrainment region 302. In typical embodiments involving high pressure liquids and rapidly moving liquid jets, the pressure in entrainment region/low pressure zone 302 will be lower than the vapor pressure of the surrounding liquid in liquid environment 300, thus causing cavitation of the liquid in entrainment region 302 and a resulting formation of an abundance of extremely small gas bubbles 304 within the liquid in the entrainment region 302, making the region visually opaque.

As discussed previously, it is desired, in preferred embodiments, for safety and performance that the instrument be designed to reduce, and preferably eliminate, undesirable effects, such as blow-by of the liquid jet, plugging of the jet-receiving opening and the evacuation lumen, and inefficient tissue/debris entrainment and removal. Also, as previously mentioned, in preferred embodiments, it is desirable that ablated tissue and debris be evacuated from the surgical site through the evacuation lumen, without the need for a source of external suction to be applied to the proximal end of the evacuation lumen. In order to provide the above-mentioned characteristics, the inventive surgical instruments for use in a liquid environment can include an evacuation lumen having specifically selected predetermined shapes and configurations, which is positionable relative to the jet opening at a specific predetermined distance. Specifically, in preferred embodiments, jet-receiving opening 193 is positioned, when the instrument is in operation, opposite jet opening 294, at a predetermined distance l therefrom, and provided in a nozzle 192 having a length to minimum diameter ratio so that essentially all of the fluid in liquid cutting jet 296 enters jet-receiving opening 193. As discussed above, liquid cutting jet 296 will tend to create entrainment region 302 surrounding the liquid cutting jet 296 when the instrument is in operation. Entrainment region 302 will typically be symmetrically deposed around liquid cutting jet 296 and will tend to diverge in a direction from jet opening 294 to jet-receiving opening 193. In typical embodiments where jet opening 294 is circular in shape, entrainment region 302 will have a truncated cone shape, having a truncated apex at jet opening 294 and a base defined as a cross section of the cone at the plane of jet-receiving opening 193. In preferred embodiments, the base of entrainment region 302 occupies between about 50% and about 100% of the cross-sectional area of jet-receiving opening 193 when the instrument is in operation, more preferably the entrainment region occupies at least about 75%, more preferably still at least about 90%, and most preferably at least about 95% of the cross-sectional area of jet-receiving opening 193 when the instrument is in operation.

Figure 6B:
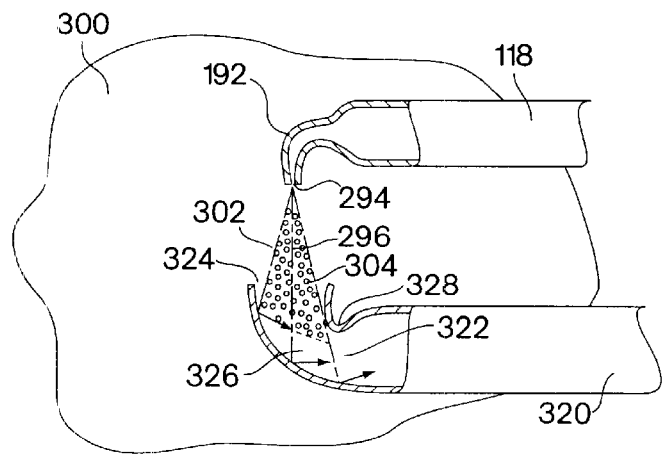
FIG. 6B is partially-cutaway, schematic illustration of a portion of the distal end of a surgical liquid jet instrument for creating a liquid cutting jet in a liquid environment, where the evacuation lumen includes a constriction.
Figure 6C:
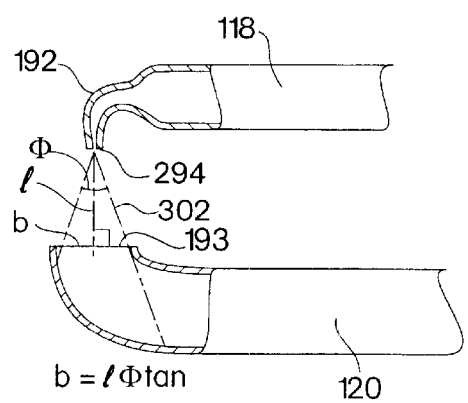
FIG. 6C is a schematic illustration of a portion of the distal end of a surgical liquid jet instrument, illustrating various geometric relationships.

As shown in FIG. 6C, the cross-sectional area of the jet-receiving opening 193 required to ensure that the entrainment region 302 occupies the desired relative fraction of the cross-sectional area of the jet-receiving opening 193, as discussed above, is functionally related to the chosen predetermined distance l between the jet opening 294 and the jet-receiving opening 193 and the degree of divergence characterizing the entrainment zone (represented by angle $\phi$ in FIG. 6C). Specifically, the desired cross-sectional radius b of the base of the entrainment region 302 at the jet-receiving opening 193 is related to predetermined distance l and the degree of divergence of the entrainment region by $b = l \tan \phi$. Predetermined distance l is typically selected based on the desired use of the surgical instrument, dictating a required fluid path cutting/ablating length. Based upon this desired predetermined distance l, the required size of the jet-receiving opening 193 is typically determined experimentally by submersing the pressure lumen 118 and nozzle 192 in a liquid environment 300, forming a liquid cutting jet 296 by supplying a liquid to the nozzle 192 at a desired predetermined pressure, and visually observing the size of the entrainment region 302 or cavitation cone created around the liquid cutting jet 296, and estimating angle $\phi$ from the observations.

As mentioned above, the predetermined separation distance l between the jet opening 294 and the jet-receiving opening 193 depends upon the requirements of the particular surgical procedure for which the surgical instrument is used; however, for some typical embodiments, the predetermined distance will have a maximum value of about 1 cm, for other typical embodiments, about 5 mm, and for yet other typical embodiments, about 1 mm. The jet-receiving opening 193 typically will have a diameter of between about 0.01 and about 0.2 inches, in other embodiments between about 0.03 and about 0.1 inches, and in some preferred embodiments a diameter of about 0.06 inches.

Referring again to FIG. 6A, a preferred configuration for evacuation lumen 120 will now be described. Preferred embodiments of evacuation lumen 120 for use in surgical instruments intended to be operated in a liquid environment include a maceration region 306 within and/or downstream and in close proximity to the inlet to evacuation lumen 120 at jet-receiving opening 193. Maceration region 306 is defined as a region that contains a liquid undergoing intensely turbulent flow and impacting an internal surface of the evacuation lumen at an acute angle, thus creating significant impacting forces capable of macerating entrained material/tissue, when the instrument is in operation. The combination of the intensely turbulent flow of the liquid in maceration region 306 and the impacting forces of liquid cutting jet 296 and the liquid in entrainment region 302 against the wall of evacuation lumen 120 enable the liquid within the maceration region to macerate at least a portion of any tissue or material entrained by the liquid in entrainment region 302 into a plurality of small particles. In preferred embodiments, the maceration region is able to macerate a substantial fraction (i.e., the majority of) the entrained tissue into a plurality of small particles. In most preferred embodiments, the plurality of particles at least partially comprises a plurality of microscopic particles too small to be seen unaided with the human eye. In all cases, the particles should be small enough to pass through evacuation lumen 120 without plugging the evacuation lumen, when the instrument is in operation.

In order to provide a maceration region, evacuation lumen 120 preferably includes a jet-deflecting portion 308 that is located adjacent to and downstream of jet-receiving opening 193. Jet-deflecting region 308 may be either a straight surface that is angled with respect to the direction of at least a central portion of liquid cutting jet 296, or in preferred embodiments, jet-deflecting region 308 comprises a smoothly curved surface upon which at least a portion of liquid cutting jet 296 impinges, where the curved surface is shaped to deflect at least a portion, and preferably all of the liquid cutting jet 296 and liquid comprising entrainment region 302 in a direction that is essentially parallel to the longitudinal axis 312 of evacuation lumen 120 in the region proximal to the jet-deflecting region 308. In preferred embodiments, the radius of curvature of the curved surface defining jet-deflecting region 308 is essentially constant, having a value of between about 0.5 and about 20 times the internal diameter of evacuation lumen 120. In one preferred embodiment, the radius of curvature of the curved surface defining jet-deflecting region 308 is essentially equal to the internal diameter of evacuation lumen 120 at jet-deflecting region 308, so that essentially no portion of jet-receiving opening 193 projects radially beyond a perimeter defined by an outer surface 314 of a portion of the evacuation lumen located proximal and adjacent to jet-deflecting region 308. It is also generally preferable for the surgical instruments provided by the invention that the liquid cutting jet be directed into the jet-receiving opening so that a direction of at least a central portion of the liquid cutting jet forms an angle of no greater than about 20 degrees, and more preferably no greater than about 10 degrees, with respect to a line normal (i.e., perpendicular) to a plane defining (i.e., co-planar to) the jet-receiving opening. In the most preferred embodiments, the central portion of the liquid jet is essentially parallel to a line that is normal to the plane defining the jet-receiving opening.

In order to provide effective eductor pump action of evacuation lumen 120, in some embodiments, evacuation lumen 120 will have an essentially constant internal cross-sectional area from jet-receiving opening 193 to a position that is proximal to the distal end of the surgical instrument where the proximal end of the evacuation lumen is located. In other embodiments, eductor pump action can be enhanced by providing an evacuation lumen having an essentially constant cross-sectional area and having a jet-receiving opening, which has a cross-sectional area that is less than the cross-sectional area of the evacuation lumen (i.e., the internal cross-sectional area of the evacuation lumen has a minimum value at the jet-receiving opening). In yet other embodiments, eductor pump action can be enhanced by providing an evacuation lumen having an internal cross-sectional area which increases continuously from a minimum value at the jet-receiving opening to a maximum value at a predetermined position located proximal to the jet-receiving opening. In such embodiments, this maximum value of the internal cross-sectional area should be essentially constant for positions within the evacuation lumen that are proximal to the above-mentioned predetermined position. In each of the above-mentioned embodiments, there are preferably essentially no reductions in the internal cross-sectional area of the evacuation lumen at any position proximal and/or downstream of the maceration region described above.

FIG. 6B shows an alternative design embodiment for the construction of the evacuation lumen for surgical instruments designed for use in a liquid surgical environment. Evacuation lumen 320 includes a constriction 322 in the internal cross-sectional area of the evacuation lumen. The constriction 322 is located proximal to jet-receiving opening 324, and is preferably positioned immediately proximal and adjacent to maceration region 326. In operation, the constriction 322 in the evacuation lumen 320 will act as a venturi as liquid within the evacuation lumen flows through the constriction, thus enhancing the eductor pump action of evacuation lumen 320. In the illustrated embodiment, constriction 322 comprises a pinch 328 in the sidewall of the tubing conduit comprising evacuation lumen 320. In preferred embodiments, the cross-sectional area of constriction 322 should be between about three and about eight times the cross-sectional area of jet-opening 294 in nozzle 192.

Referring again to FIG. 6A, evacuation lumen 120 is shaped and positioned relative to pressure lumen 118 so that at least a central portion of liquid cutting jet 296 is directed into jet-receiving opening 193 in a direction forming a non-zero angle with respect to (i.e. non-parallel with) the longitudinal axis 312 of evacuation lumen 120 in a region proximal to jet-deflecting region 308. In some embodiments, this angle can be between about 45 degrees and about 115 degrees, in other embodiments between about 80 degrees and about 100 degrees, and in some preferred embodiments, as illustrated, the angle can be about 90 degrees.

Figure 7A:
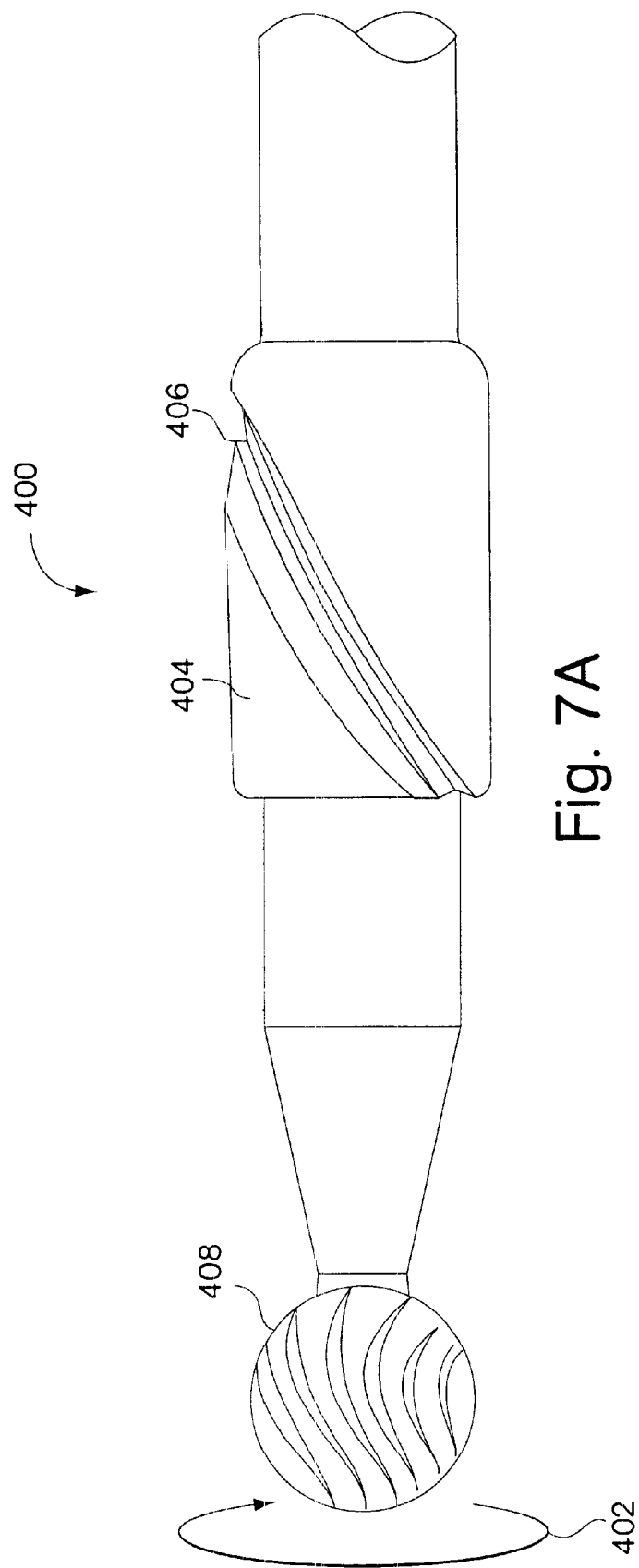
FIG. 7A is a schematic, perspective illustration of a portion of a rotatable shaft including a grinding burr at its distal end, where the rotatable shaft includes a helically grooved channel disposed on at least a portion of the outer surface of the shaft.

As described above, in some embodiments of the invention involving surgical instruments including rotatable shafts, liquid and debris surrounding a grinding burr, or other tissue contacting component at a distal end of the rotatable shaft, can be evacuated by coupling a sheath of the instrument surrounding the rotatable shaft to a source of external vacuum or suction. In other embodiments, also as mentioned above, rotation of the rotatable shaft itself may be utilized to generate an evacuating force for removing liquid and debris from an area surrounding the distal end of the rotatable shaft. FIG. 7A shows a partial section of a distal region of rotatable shaft 400 that is constructed and arranged to generate an evacuation force tending to drive liquid and debris from the distal end of a sheath surrounding shaft 400, when it is assembled within a surgical instrument according to the invention, to the proximal end of such sheath. "Constructed and arranged to generate an evacuation force" as used herein in the present context refers to the ability of a rotatable shaft, rotating either within a surrounding sheath or without a surrounding sheath, to be able to drive liquid from a region near the distal end of the rotatable shaft towards the proximal end of the rotatable shaft and out of a surgical field into which a distal end of the rotatable shaft is placed, without the need for an external source of suction.

In operation, rotatable shaft 400 rotates in a direction shown by arrow 402. Rotatable shaft 400 includes a portion 404 of increased cross sectional dimension, preferably having a cross sectional dimension only slightly less than an internal cross sectional dimension of a surrounding sheath in which rotatable shaft 400 is disposed when assembled into a surgical instrument. Region 404 includes a helically grooved channel 406 machined therein. Both region 404 and channel 406 are positioned on shaft 400 so that they are surrounded by a sheath when assembled into a surgical instrument. Rotation of shaft 400 in the direction of arrow 402 during operation creates a driving force tending to move fluid and debris from the distal end of shaft 400, in proximity to grinding burr 408, to a proximal end of the shaft and out of the surgical field in which burr 408 is operating.

Figure 7B:
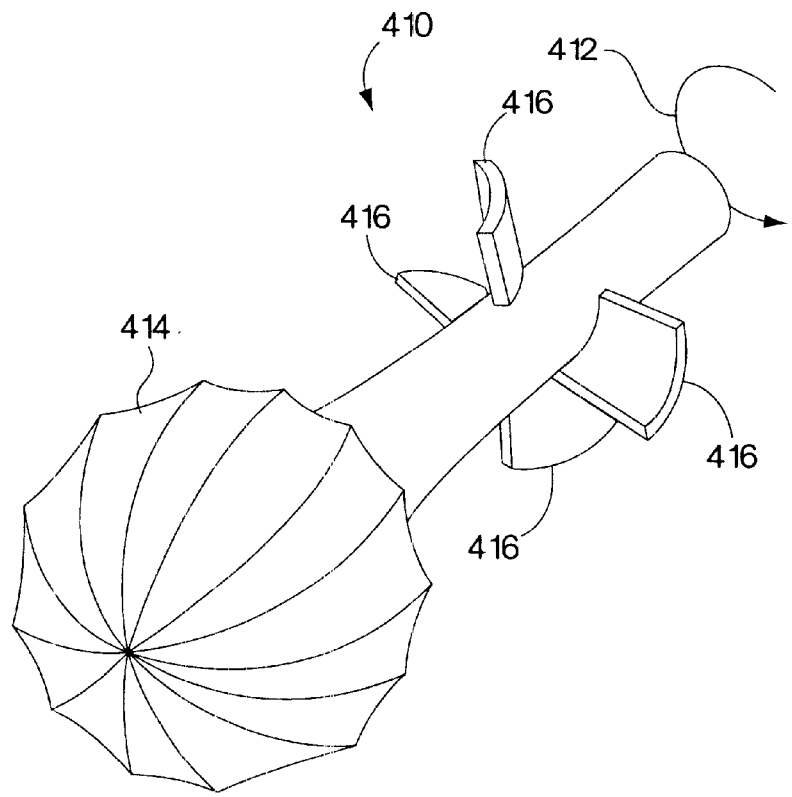
FIG. 7B is a schematic, perspective illustration of a portion of a rotatable shaft including a grinding burr, where the rotatable shaft includes an impeller thereon.

FIG. 7B shows a partial view of a distal region of an alternative embodiment of a rotatable shaft 410 that is constructed and arranged to generate an evacuation force upon rotation in the direction of arrow 412. Shaft 410 includes grinding burr 414 at a distal end thereof, and further includes impellers 416, which are disposed within a surrounding sheath when shaft 410 is assembled into a surgical instrument, according to the invention. Upon rotation within the surrounding sheath, impellers 416 generate an evacuation force tending to drive liquid and debris towards the proximal end of the shaft during operation of the instrument.

Figure 7C:
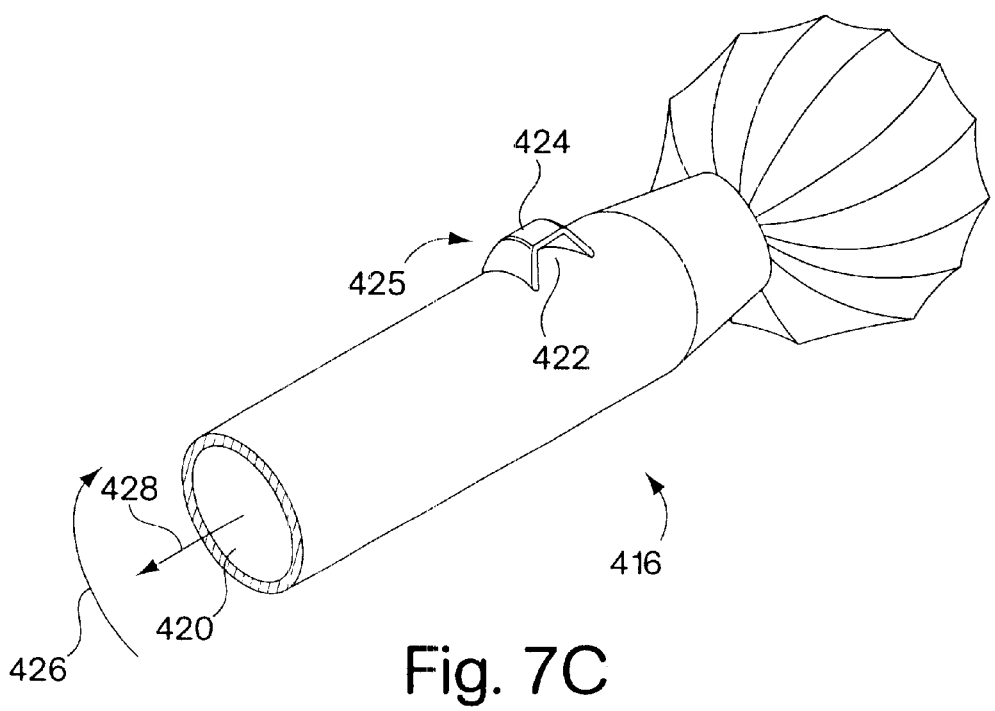
FIG. 7C is a schematic, perspective illustration of a portion of a rotatable shaft with a grinding burr thereon and including a scoop shaped aperture in fluid communication with a channel defined by a hollow center of the shaft.

FIG. 7C shows yet another embodiment of a rotatable shaft constructed and arranged to generate an evacuation force upon rotation. Rotatable shaft 416, having grinding burr 418 at a distal end thereof, has an interior that is hollow forming a channel 420, which extends distally up to at least aperture 422 in scoop 424 (scoop 424 together with aperture 422 will be hereinafter collectively referred to as a "scoop-shaped aperture" 425). Aperture 422 is in fluid communication with channel 420 formed along the hollow shaft of rotatable shaft 416. Upon rotation of shaft 416 in the direction of arrow 426 scoop-shaped aperture 425 scoops fluid and debris into aperture 422 and creates a driving force tending to move the fluid and debris in the direction of arrow 428 towards the proximal end of shaft 416. In preferred embodiments, the scoop-shaped aperture 425 is disposed within a surrounding sheath when shaft 416 is assembled into a surgical instrument, according to the invention, and the scoop-shaped aperture 425 is shaped and positioned to be able drive liquid and debris through channel 420 toward the proximal end of the surgical instrument upon rotation of shaft 416 during operation of the instrument. "Shaped and positioned to drive liquid and debris" when used in the context of the scoop-shaped aperture 425 refers to a projecting scoop 424 having an aperture 422 therein that is in fluid communication with a central channel 420 of a shaft 416 that rotates in a given direction 426, where the aperture 422 within the scoop 424 faces in a direction with respect to the rotation of the shaft such that upon rotation of the shaft, liquid and debris tends to be forced through the aperture and into and along the channel defined by the hollow shaft. As will be discussed in greater detail in the context of FIGS. 11A–11B, for embodiments including rotatable shafts that generate their own evacuation force, in addition to evacuating a region of a surgical field surrounding the distal end of the rotatable shaft, the evacuation force created by the rotating shaft may also be used to create an evacuation force tending to evacuate other regions of the surgical instrument, for example regions of the housing containing the drive mechanism for the rotatable shaft.

Figure 8A:
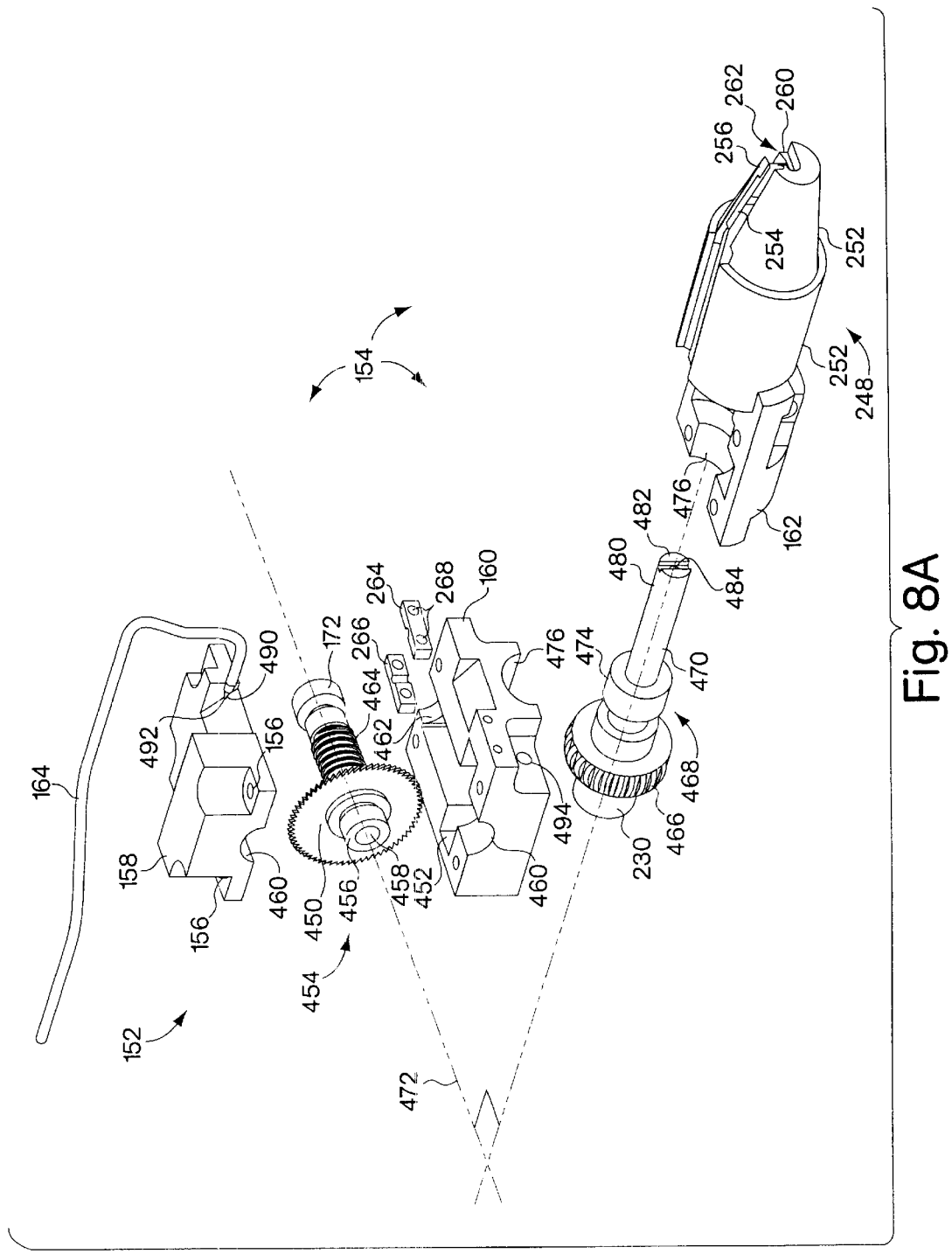
FIG. 8A is a schematic, exploded, perspective illustration of the rotatable shaft drive mechanism of the instrument as in FIG. 1.

FIG. 8A shows an exploded perspective view of one preferred embodiment for rotatable shaft drive mechanism 152. Rotatable shaft drive mechanism 152 includes a liquid jet-driven rotatable rotor 450, which in the embodiment illustrated in FIG. 8A comprises a saw-tooth rotor. Upon assembly of the three subcomponents of rotor housing 154 (i.e., rotor cap 158, rotor housing block 160 and rotor housing bottom 162), rotatable rotor 450 is contained and rotates within a rotor slot 452 included in rotor housing block 160 and rotor housing cap 158. Rotatable rotor assembly 454 includes, in addition to rotatable rotor 450, rotor bearings 172 and 456 disposed at each end of a central shaft 458, upon which the assembly rotates. Bearings 172 and 456 are held within flanges 460 and 462 upon assembly of the rotor housing.

Figure 8B:
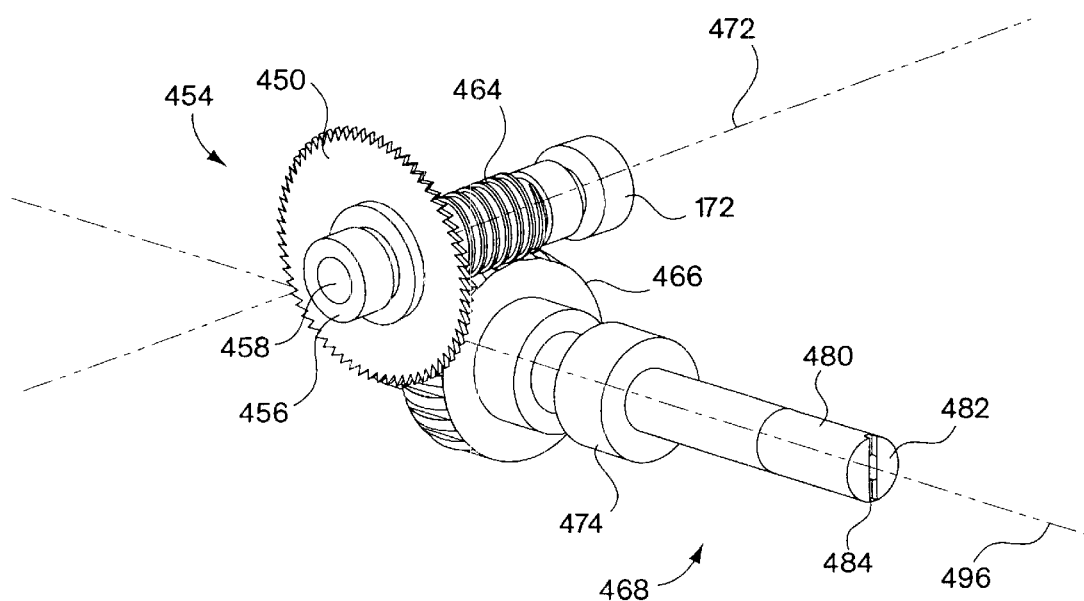
FIG. 8B is a schematic, perspective illustration of a rotor assembly and rotatable shaft drive assembly of the rotatable shaft drive mechanism as in FIG. 8A.
Figure 8C:
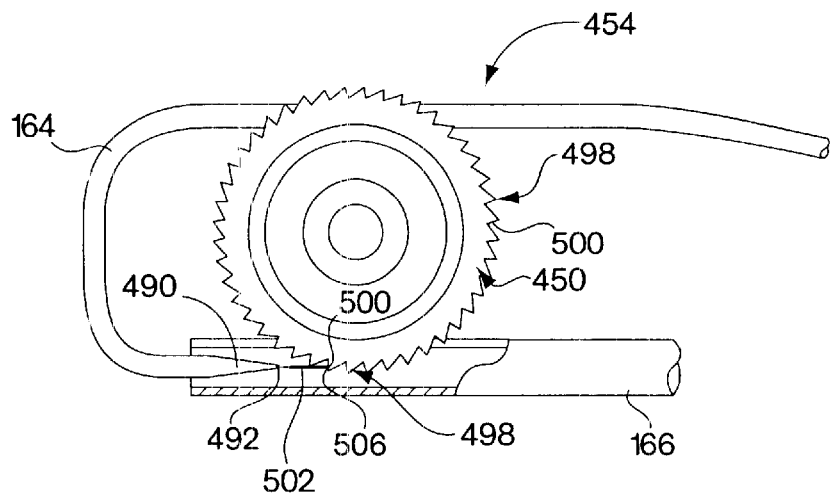
FIG. 8C is a partially-cutaway, schematic illustration of a portion of the rotatable shaft drive mechanism as in FIG. 8A showing the arrangement of the liquid jet nozzle, rotatable rotor, and liquid jet evacuation lumen.
Figure 8D:
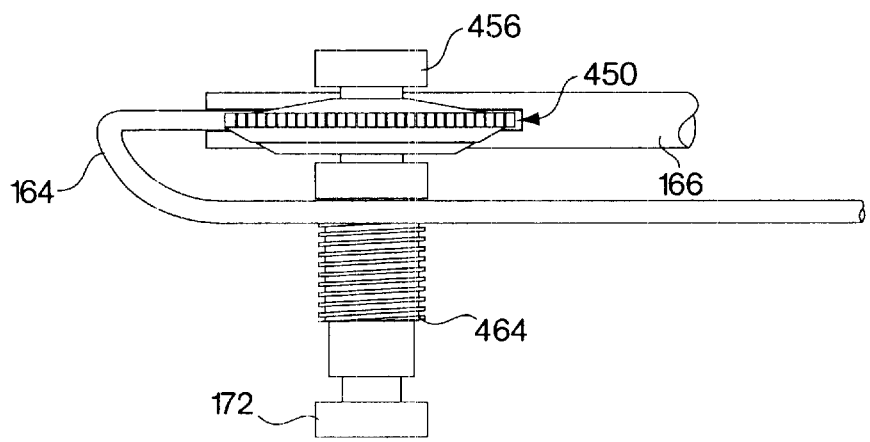
FIG. 8D is a schematic illustration of the liquid jet evacuation lumen and rotor assembly as in FIG. 8C, as viewed from above.
Figure 8E:
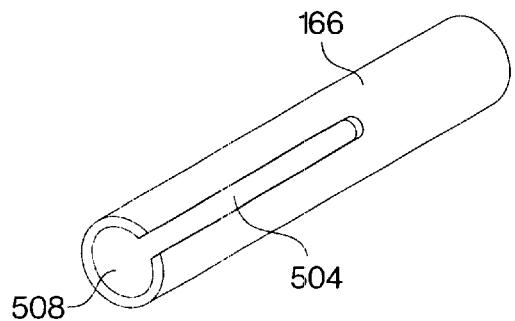
FIG. 8E is a schematic, perspective illustration of a portion of the evacuation lumen as in FIG. 8D.

Rotor assembly 454, in the illustrated embodiment, also includes a worm gear 464 which mates with a complementary worm wheel 466 located on rotatable shaft drive assembly 468 (shown more clearly in an assembled state in FIG. 8B). Gear reduction mechanisms utilizing worm gears, such as illustrated in FIG. 8A, are preferred for some embodiments because they provide relatively high gear reduction ratios for their size. In other embodiments, where a lower degree of gear reduction and a lower difference in rotational speed between rotatable rotor 450 and drive shaft 470 of rotatable shaft drive assembly 468 is required or desired, other means of gear reduction, for example spur gears, helical gears, or any other suitable gear reduction mechanisms apparent to those of ordinary skill in the art can be utilized. In addition, for embodiments where high speeds are required or desired or only low torques are necessary during operation, the gear reduction mechanism may be eliminated entirely and the rotatable rotor assembly 454 may be utilized to drive rotatable shaft 124 directly. In such an embodiment, rotatable shaft drive mechanism 152 could dispense entirely with rotatable shaft drive assembly 468, and instead couple the rotatable shaft 124 directly to rotatable rotor assembly 454. Of course, in such embodiments, it is desirable to position rotatable rotor assembly 454 so that its longitudinal axis 472 is aligned parallel to longitudinal axis of rotatable shaft 124 (i.e., it would be desirable to orient rotatable rotor assembly 452 in the orientation currently shown for rotatable shaft drive assembly 468 in FIG. 8A).

Rotatable shaft drive assembly 468, as illustrated, is comprised of drive shaft 470 to which is attached worm wheel 466. The assembly also includes two shaft drive bearings 230 and 474 which permit rotation of drive shaft 470 upon assembly of rotatable shaft drive mechanism 152. Bearings 230 and 474 are held by flanges (e.g., 476) provided in the housing components, upon assembly of the mechanism. Bearings 172, 456, 230, and 474, as illustrated, comprise ball bearings; however, in alternative embodiments the bearings may comprise journal bearings, hydrodynamic bearings, or any other suitable bearings as apparent to those of ordinary skill in the art.

The components comprising rotatable shaft drive mechanism 152 are preferably formed from a rigid, durable material, such as a variety of metals, for example surgical grade stainless steel. Because rotatable rotor assembly 454 and rotatable shaft drive assembly 468 rotate at high velocity during operation of the instruments, it will be apparent to those of ordinary skill in the art that the rotatable rotor 450, worm wheel 466, and other components comprising the assemblies should be properly balanced so that they can rotate at high rotational speeds without undue vibration of the instrument. Rotatable shaft drive assembly 468 further includes attached to its distal end rotatable shaft mounting component 480 having a distal surface 482 including a rotatable shaft mounting slot 484 that is sized and shaped to surround and couple to coupling region 200 of rotatable shaft 124, when the instrument is fully assembled.

Rotatable shaft drive mechanism 152 includes pressure lumen 164 which supplies high pressure liquid to nozzle 490 having jet opening 492 therein for forming a liquid jet that is directed to impinge upon rotatable rotor 450, thus driving rotation of the rotor and the rotatable shaft, when rotatable shaft drive mechanism 152 is assembled and operated. Upon assembly, as previously illustrated in FIG. 4, pressure lumen 164 is held in position to rotor housing block 160 by means of rotor jet pressure lumen mounting blocks 264, 266. Upon assembly and attachment of pressure lumen 164 to rotor housing block 160, nozzle 490 passes into rotor housing block 160 through orifice 494 so that jet opening 492 is oriented to properly direct a liquid jet at rotatable rotor 450 (shown more clearly in FIGS. 8C and 8D and discussed below). In addition, and not shown in the current figure, rotor jet evacuation lumen 166, rotor housing cap evacuation conduit 168, and rotor housing bottom evacuation conduit 170 are connected to the various components of rotatable shaft drive mechanism 152, as shown and discussed previously, to enable essentially complete evacuation of liquid from the internal spaces surrounding the rotatable components of the mechanism, upon assembly of the mechanism, to prevent submersion of rotatable rotor or the rotatable components in liquid, when the instrument is in operation.

FIG. 8B is a perspective view of rotatable rotor assembly 454 and rotatable shaft drive assembly 468 as they are coupled upon assembly of rotatable shaft drive mechanism 152. As shown in FIG. 8B, the various housing components have been eliminated to show assemblies 454 and 468 with greater clarity. As is shown in the figure, for embodiments having a drive mechanism including gear reduction (e.g., provided by worm gear 464 and worm wheel 466 as illustrated) it is preferred to align rotatable rotor assembly 452 such that its longitudinal axis 472 is essentially perpendicular to longitudinal axis 496 of rotatable shaft drive assembly 468.

As will be apparent to those of ordinary skill in the art, the particular rotational speeds of rotor 450, rotor drive assembly 454, and drive shaft 470 of rotatable rotor drive assembly 468 must be selected based upon the needs of the particular surgical application and on the characteristics of the particular rotatable component being utilized for tissue contact and being rotated by the rotatable shaft. For typical applications utilizing the inventive surgical instruments, the rotational speed of rotatable rotor 450 will be at least about 16,000 RPM, in other embodiments at least about 65,000 RPM, in yet other embodiments at least about 130,000 RPM, in yet other embodiments at least about 250,000 RPM, and in still other embodiments at least about 500,000 RPM. The diameter of rotatable rotor 450 is typically at least about 0.5 inch, in other embodiments at least about 1 inch, in other embodiments at least about 2 inches, in other embodiments at least about 5 inches, and in yet other embodiments at least about 10 inches. The gear reduction mechanism is selected and configured in preferred embodiments, so that the rotational speed of rotatable rotor 450 will exceed the rotational speed of drive shaft 470 of rotatable rotor drive assembly 468. In typical embodiments, the rotational speed of rotatable rotor 450 will exceed that of drive shaft 470 by at least about a factor of 2, in other embodiments by at least about a factor of 5, in other embodiments by at least about a factor of 10, in other embodiments by at least about a factor of 20, and in yet other embodiments by at least about a factor of 30. In one particularly preferred embodiment involving a surgical instrument including a rotatable shaft having a 5 mm diameter fluted burr at a distal end thereof, which is utilized for bone grinding in a surgical operating field, rotatable rotor 450 comprises a 1 inch diameter saw-tooth rotor having between about 10 and 200 teeth, and in one preferred embodiment about 80 teeth, which is driven at a rotational speed during operation of about 130,000 RPM and is coupled to drive shaft 470 via a worm-gear reduction mechanism such that the rotational speed of drive shaft 470 is about 1/10th that of rotatable rotor 450 during operation.

For embodiments utilizing a rotatable rotor which is a saw-tooth rotor, depending on the diameter of the saw-tooth rotor and the size of the teeth when compared to the diameter of the rotor, the number of teeth provided on the rotor can range from about 10 to about 200. As discussed immediately above, one particularly preferred saw-tooth rotor embodiment comprises a 1 inch diameter rotor having a thickness of about 0.040 inch and having about 80 teeth therein, each tooth providing a jet impacting surface about 0.040 inch wide by 0.040 inch in height.

FIGS. 8C–8E are detailed views of rotatable rotor 450 and rotatable rotor assembly 454 showing the configuration of the rotatable rotor with relation to liquid jet forming nozzle 490 and rotor jet evacuation lumen 166, when rotatable shaft drive mechanism 152 is assembled. For clarity, components other than the rotatable rotor assembly, pressure lumen and evacuation lumen are not shown in the figures. Referring to FIG. 8C, rotatable rotor 450 comprises a saw-tooth rotor including a plurality of teeth 498 each including an essentially planar impacting surface 500 upon which liquid jet 502 impacts, when the instrument is in operation. Nozzle 490 of pressure lumen 164 is preferably configured to create an essentially collimated liquid jet as a high pressure liquid streams therethrough. The particular configuration of nozzle 490 can be essentially equivalent to that discussed previously with respect to preferred nozzles for forming liquid cutting jets at the distal end of the surgical instrument. Specifically, nozzle 490, in preferred embodiments, has a length to minimum internal diameter ratio of between about 2 and about 10 with a preferred length to minimum internal diameter ratio of about 6. Jet opening 492 is positioned at a selected predetermined distance from the impacting surface 500 upon which liquid jet 502 impacts, when the instrument is in operation. This predetermined distance, in preferred embodiments, is the minimum distance possible, without having teeth 498 of the rotor impacting nozzle 490 upon rotation of the rotor. For example, when utilizing a 1 inch diameter saw-tooth rotor having teeth 498 with a height of about 0.040 inch, the distance between jet opening 492 and the impacting surface of the saw tooth upon which the liquid jet impacts, is preferably less than about 1 cm, and more preferably less than about 1 mm.

In preferred embodiments, predetermined distance, nozzle length to minimum internal diameter ratio, and the size of each impacting surface 500 are chosen so that essentially the entirety of liquid jet 502 impacts an impacting surface 500 of the rotor during operation. In other words, the above parameters are preferably selected so that at the point of impact 506 of liquid jet 502 with an impacting surface 500, the cross-section of liquid jet 502, within the plane of impacting surface 500, is essentially entirely incident on impacting surface 500 so that essentially no part of the liquid jet "misses" or "blows by" the impacting surface.

In such a situation, the momentum of the entire liquid jet can potentially be imparted to rotatable rotor 450 to create rotational motion of the rotor.

The distal end of rotor jet evacuation lumen 166 is shown partially cutaway in FIG. 8C to more clearly show nozzle 490, liquid jet 502, and rotatable rotor 450, as positioned within the distal end of the lumen. As shown more clearly in FIGS. 8D and 8E, the distal end of evacuation lumen 166, which is disposed within rotor housing block 160 upon assembly of rotatable shaft drive mechanism 152, includes a slit 504 in which a portion of rotatable rotor 450 is located during operation. Furthermore, the distal end of pressure lumen 164 including nozzle 490 is also positioned within and essentially completely surrounded by the distal end of evacuation lumen 166 when the drive mechanism is assembled. This configuration serves to maximize the containment of any spray that is created upon the impacting of liquid jet 502 with an impacting surface 500 of rotatable rotor 450. This is especially important for periods of operation of the instrument where the rotatable shaft of the instrument is subjected to significant torque tending to inhibit its rotation. During such periods of operation, rotatable rotor 450 will tend to rotate at a speed that is less than the velocity of liquid jet 502. Under such conditions, liquid jet 502 can have a tendency to form spray or mist upon impacting an impacting surface 500. By contrast, under conditions of free rotation, rotatable rotor 500 rotates at a speed essentially equal to the speed of liquid jet 502, so that the trajectory of liquid jet 502 remains essentially constant even after impacting an impacting surface 500, and minimal spray is created. In an alternative embodiment, the evacuation lumen can be configured and positioned so that it does not surround and enclose any portion of the distal end of pressure lumen but, instead, is positioned distally of the nozzle in the pressure lumen, preferably with a jet-receiving opening positioned within about 0.01 inch of the jet opening in the nozzle.

The design of evacuation lumen 166 as illustrated enables effective evacuation of essentially all of the liquid comprising liquid jet 502 from the housing enclosing the rotatable rotor assembly during operation of the device under a wide range of loads and resistances applied to the rotatable shaft of the instrument. In certain embodiments, the proximal end of evacuation lumen 166 can be placed in fluid communication with a source of external suction in order to effect evacuation of liquid comprising liquid jet 502. In some preferred embodiments, liquid jet 502, via eductor pump action, described previously, is able to create its own evacuation force tending to evacuate the liquid comprising liquid jet 502, together with any spray formed upon impacting with a surface of the rotor, from the distal end of evacuation lumen 166 without the need for an external source of suction.

In typical embodiments, jet opening 492 in nozzle 490 has a diameter of between about 0.001 and about 0.02 inch, more preferably between about 0.003 and 0.01 inch, and in one preferred embodiment has a diameter of about 0.005 inches. In typical embodiments, liquid is supplied to nozzle 490 to form a liquid jet at a pressure of at least about 1,000 psig, in other embodiments at least about 5,000 psig, in another embodiments at least about 15,000 psig, and yet in other embodiments, at least about 30,000 psig. In one preferred embodiment, liquid is supplied to nozzle 490 to form a liquid jet at a pressure of about 8,000 psig. Evacuation lumen 166, in typical embodiments, has a jet receiving opening 508 having a diameter of between about 0.01 and about 0.3 inches, more preferably between about 0.05 and about 0.2 inches and in one preferred embodiment about 0.12 inches. As will be discussed below in more detail in the context of FIGS. 11A–11B, for embodiments wherein liquid jet 502 is directed into an evacuation lumen 166 creating an evacuation force by eductor pump action without the need for an external source of suction, this evacuation force can be utilized not only to evacuate liquid comprising liquid jet 502, but also to evacuate or assist in evacuating other components of the surgical liquid jet instrument.

Figure 9A:
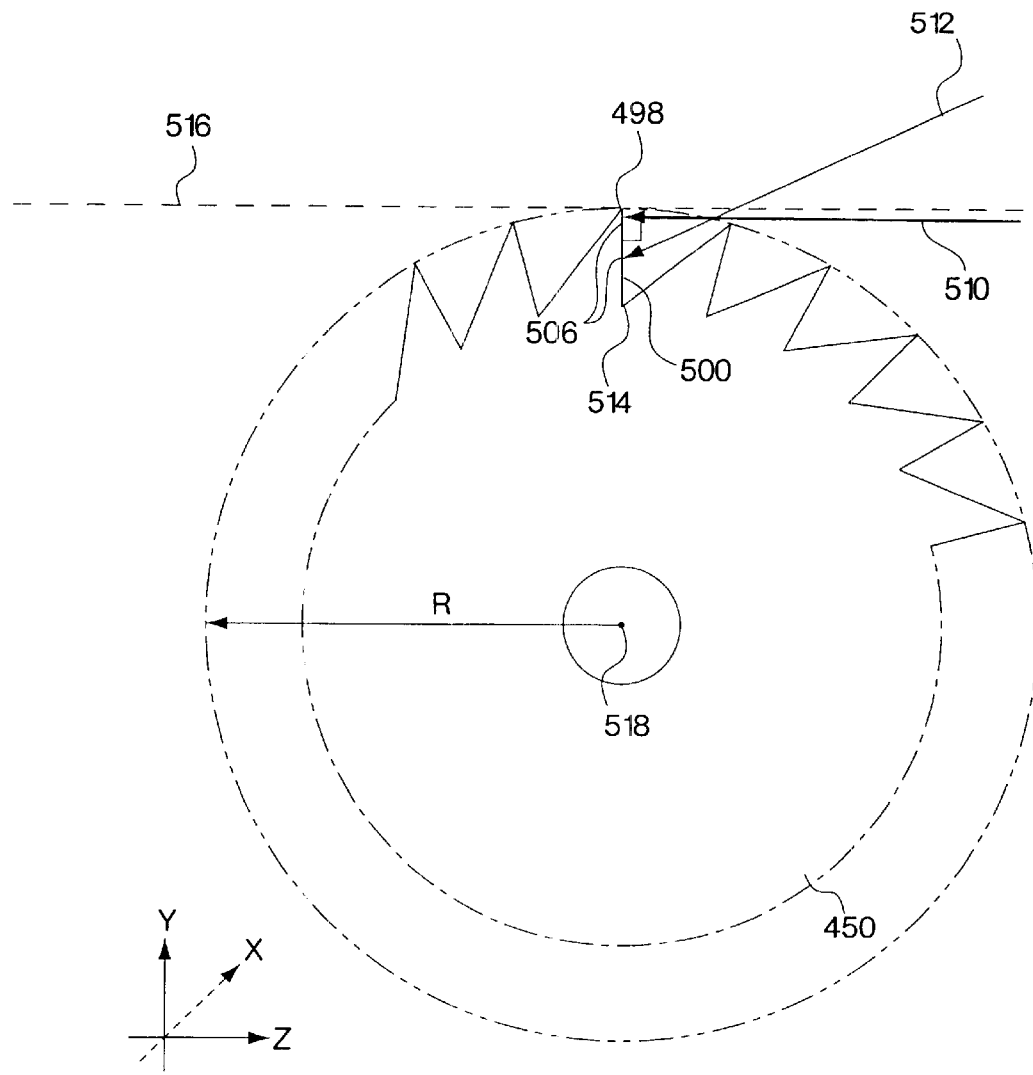
FIG. 9A is a schematic illustration of a saw-tooth rotor.
Figure 9B:
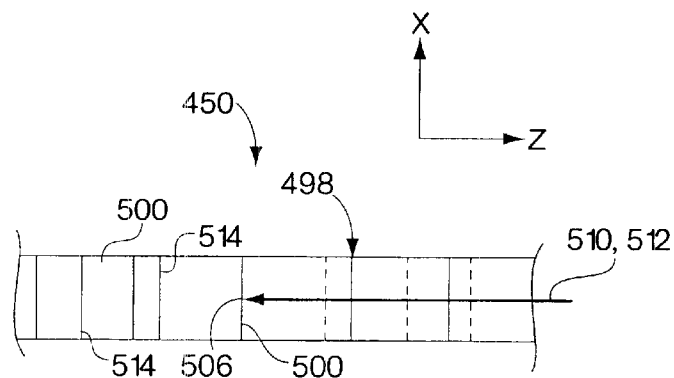
FIG. 9B is a schematic illustration of a portion of the saw-tooth rotor as in FIG. 9A, as viewed from above.

Rotatable rotor 450 is shown schematically and in greater detail in FIGS. 9A and 9B. FIG. 9A shows rotatable rotor 450 as viewed from the same orientation as shown in FIG. 8C above. FIG. 9A illustrates a preferred embodiment for orientating and directing liquid jet 502 at an impacting surface 500 of saw teeth 498 on rotatable rotor 450. FIG. 9B shows rotatable rotor 450 as viewed from above, more clearly showing the orientation of the fluid jet within the plane of the rotor. The direction of the liquid jet is shown by arrows 510 and 512 in the figures. As shown in the figures, it is preferred to direct the liquid jet towards surface 500 of rotatable rotor 450 so that it impacts the surface at a non zero angle (i.e., the liquid jet is not directed tangentially to the surface). Even more preferably, as shown in FIG. 9B, the liquid jet is directed towards impacting surface 500 of rotatable rotor 450 such that the direction of the liquid jet 510, 512 is essentially perpendicular to the surface, at least as measured in the x-z plane as illustrated in FIG. 9B. As shown in FIG. 9A, in some embodiments, for example those having a liquid jet directed along direction 510, the liquid jet can be directed at surface 500 so that it is also essentially perpendicular to the surface as measured in the y-z plane, illustrated in FIG. 9A. In other embodiments, the liquid jet can be directed along liquid jet direction 510, such that the liquid jet is directed toward surface 500 at a relatively small angle as measured within the y-z plane so that the liquid jet is angled somewhat to impinge closer to the base 514 of saw tooth 498. The term "essentially perpendicular," when used in the context of describing the direction of a liquid jet with respect to an impacting surface of a rotatable rotor, refers to the liquid jet being directed towards the impacting surface of the rotatable rotor such that it is essentially perpendicular to the surface in at least the x-z plane as illustrated in FIG. 9B.

Preferred saw tooth rotors have liquid jet impacting surfaces that are essentially planar. Furthermore, as described above in the preceding paragraph, the surfaces are preferably oriented with respect to the rotor such that each impacting surface is oriented essentially perpendicularly (or is essentially perpendicular to) a liquid jet impacting thereon at at least one rotational position of the rotatable rotor. Furthermore, in preferred embodiments, each liquid jet impacting surface 500 of rotatable rotor 450 is also oriented at an angle of between about 75 degrees and about 105 degrees with respect to a line 516 tangent to the circle circumscribed by the outermost perimeter of the rotor as it rotates about its axis of rotation 518. In some especially preferred embodiments, each liquid jet impacting surface 500 of rotatable rotor 450 is oriented essentially perpendicularly to line 516

Figure 10A:
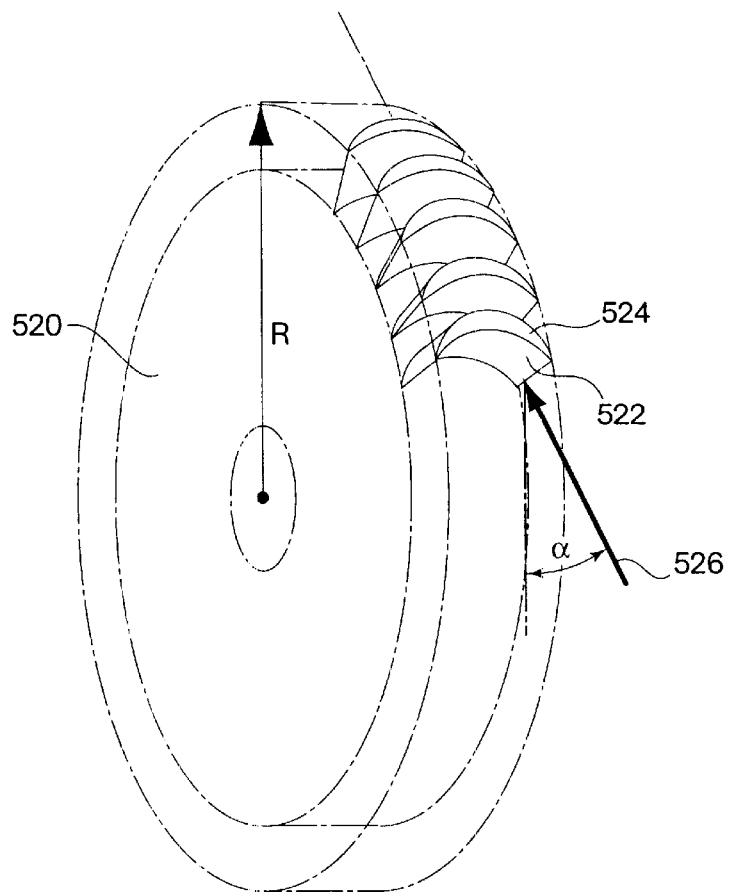
FIG. 10A is a schematic, perspective illustration of a curved-vein rotor.

In alternative embodiments, a rotor having liquid jet impacting surfaces that are curved may be utilized in place of a saw tooth rotor having planar impacting surfaces, as previously described. FIG. 10A shows a perspective view of a curved-vane rotor 520 having curved liquid jet impacting surfaces 522. Curved impacting surfaces 522 are defined by a series of curved vanes 524 positioned along the periphery of rotor 520. As illustrated, preferred curved-vane rotors have impacting surfaces 522 that are oriented to provide an impacting surface that is concave with respect to the direction of an incoming liquid jet, shown by arrow 526. In the illustrated embodiment, curved impacting surfaces 522 comprise semi-cylindrical surfaces. For embodiments utilizing rotors having smoothly curved liquid jet impacting surfaces 522, it is preferred for the liquid jet to be oriented in a direction 526 such that it is directed toward surface 522 essentially tangentially to the surface.

Figure 10B:
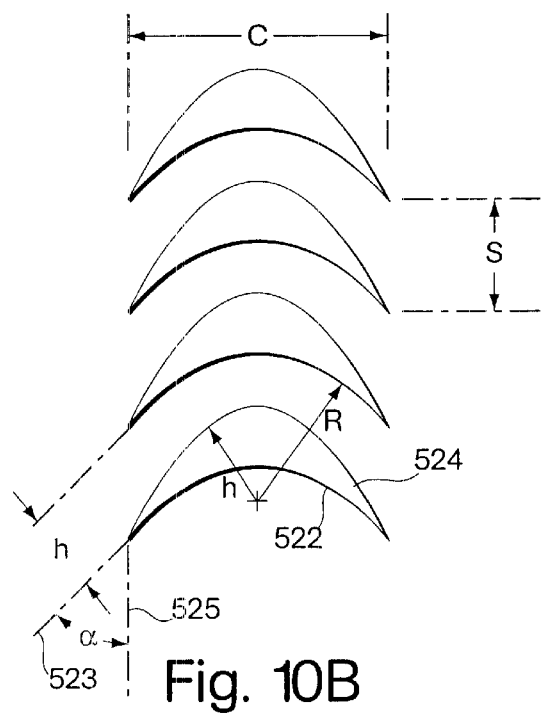
FIG. 10B is a schematic illustration of several curved veins of the curved-veined rotor as in FIG. 10A.

FIG. 10B illustrates a particularly preferred configuration for orienting and positioning curved vanes 524 around the periphery of rotor 520. As illustrated in FIG. 10B, in a preferred embodiment, angle α formed between the line 523 tangent to impacting surface 522 of the curved vane and the line 525 defining the edge of rotor 520 should be between about 5 degrees and about 30 degrees, and in a preferred embodiment is about 17 degrees. In addition, channel width h between curved vanes 524, through which the liquid comprising an impacting liquid jet flows when the rotor is in operation, is preferably between about the diameter of the impacting liquid jet at the point of impact and a value of about twice the diameter of the liquid jet. In addition, the width of curved vanes 524 (C) is preferably chosen with respect to the inter-vanes spacing (S) such that the ratio (C/S) is between about 1.0 and about 1.5. In yet other embodiments, a smoothly curved jet impacting surface may be provided by utilizing a Terry rotor for driving the rotatable shaft of the surgical instrument. Terry rotors are known in the mechanical arts and are described in greater detail in, for example, Balje, O. E. *Turbomachines: A Guide to Design, Selection, and Theory,* John Wiley & Sons, New York, N.Y., 1981, pp. 252–256.

FIGS. 11A and 11B show two potential configurations for supplying evacuation to the various evacuation lumen and conduits of surgical instrument 100. In another embodiment, not illustrated, an external source of suction is coupled in fluid communication to each of the evacuation lumen and evacuation conduits of surgical instrument 100 in order to provide a suction force to each that is generated by the external source of suction. In alternative embodiments, suction created by the eductor pump action of cutting jet evacuation lumen 120, rotor jet evacuation lumen 164, and/or the suction force created by any of the self-evacuating rotatable shaft designs shown previously in FIGS. 7A–7C can instead be utilized to supply a source of suction for evacuating various other evacuation conduits of instrument 100.

FIG. 11A illustrates one embodiment for evacuating the various evacuation lumen and conduits of instrument 100. For the illustrated embodiment, the rotatable shaft of the surgical instrument would not be configured to provide self-evacuation. Accordingly, an external source of suction 530 is coupled in fluid communication to evacuation conduit 532, which in turn, is in fluid communication with the sheath 132 surrounding the rotatable shaft. By contrast, the remaining evacuation lines of the instrument are each connected to a manifold 534 configured as shown. Fluid momentum supplied by the eductor pump action of the rotor jet evacuation lumen 166 in combination with liquid cutting jet evacuation lumen 120 is utilized to create a suction force within manifold 534 sufficient to evacuate the evacuation conduit 168 connected to rotor housing base 162 and the evacuation conduit 170 connected to rotor housing cap 158. It should be understood that manifold 534 may be formed by connecting the exhaust lumen/conduits in the manner shown in FIG. 11A outside of the body of the surgical instrument (as would be the case if using surgical instrument 100 as illustrated in FIG. 1 above); however, in other embodiments, manifold 534 can be configured to and contained within the body of the surgical instrument.

FIG. 11B shows an alternative embodiment for a surgical fluid jet instrument that includes a rotatable shaft configured to create an evacuation force upon rotation of the shaft, as previously described in FIGS. 7A–7C. With such a configuration, the external source of suction can be eliminated entirely, and the entire surgical instrument can be configured to be self-evacuating without the need for an external source of suction. In the illustrated embodiment, the various evacuation lumen and conduits are connected to a manifold 542. In the illustrated embodiment, the liquid momentum supplied by the eductor pump action of rotor jet evacuation lumen 166 and liquid cutting jet evacuation lumen 120 are utilized in combination with the liquid motive force supplied by the rotatable shaft through sheath 132 to create a sufficient suction in manifold 542 to evacuate evacuation conduit 168 connected to rotor housing block 160 and evacuation conduit 170 connected to the rotor housing base 162 of the surgical instrument.

Figure 12:
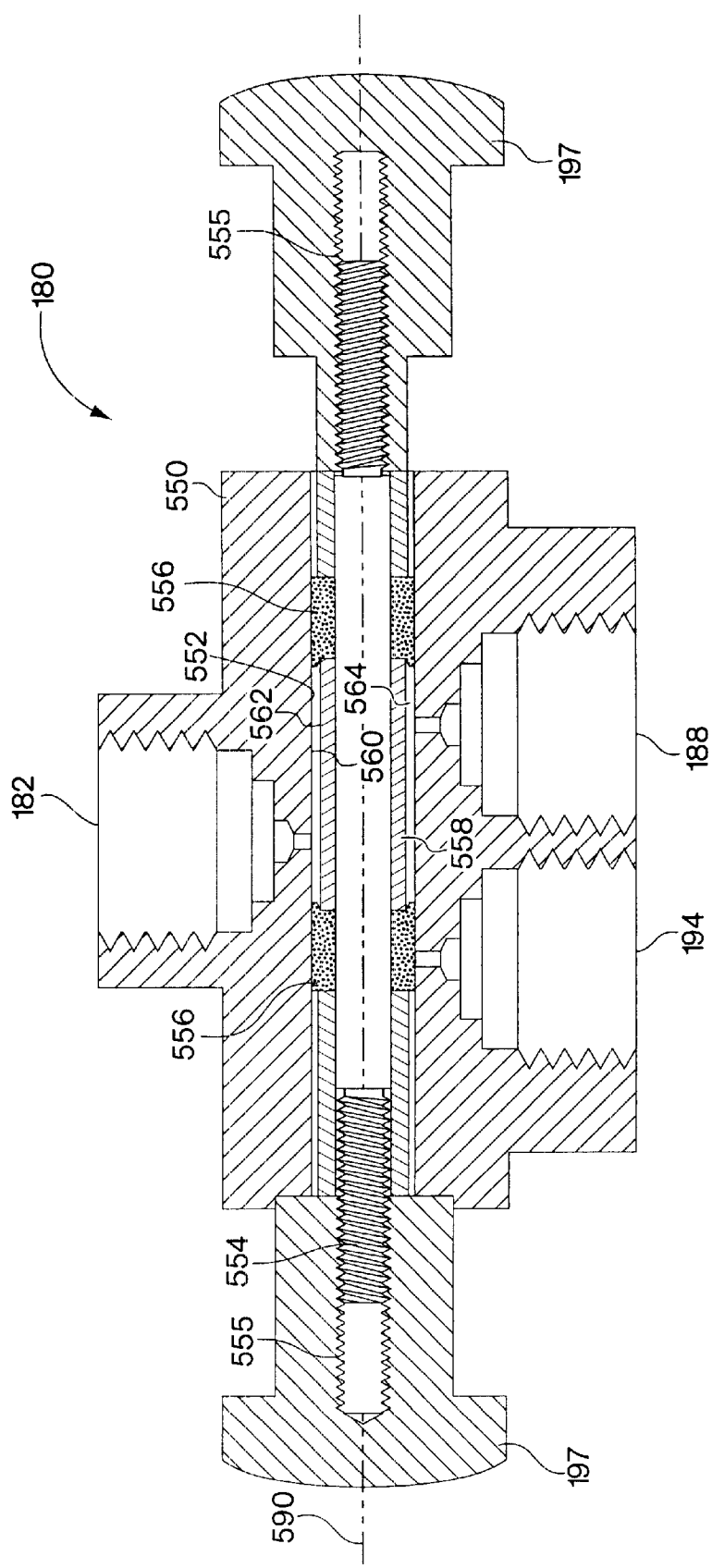
FIG. 12 is a schematic, cross-sectional illustration of the liquid flow directing valve of the instrument as in FIG. 1.

A cross-sectional view showing the internal details of liquid flow directing valve 180 is illustrated in FIG. 12. Liquid flow directing valve 180 includes a valve body 550 formed of a rigid sturdy material, for example surgical grade stainless steel, having a centrally disposed bore therein forming a cylinder 552 internal to valve body 550. Valve 180 is configured as a slidable three-way valve. Valve body 550 further includes an inlet 182 comprising a bore having threaded walls configured to mate with a high pressure tubing coupling 186 (shown in FIG. 1). Similarly, valve body 550 further includes a first 188 and a second 194 outlet configured with internally threaded surfaces for coupling to high pressure connectors 190 and 196 respectively.

Disposed within centrally disposed cylinder 552 is a shaft 554, preferably comprised of a rigid, durable metal such as surgical grade stainless steel, connected by threads 555 at each end to user actuated knobs 197. Also disposed on shaft 554 are two elements 556 comprising pressure tight sealing components for preventing leakage of high pressure liquid from and within valve 180. Elements 556 comprising the pressure tight sealing components are described in greater detail below in the context of FIGS. 13A and 13B. Elements 556, while shown for use within the context of liquid flow directing valve 180, can also be used for a wide variety of other applications where a high pressure, slidable sealing component is needed to form a high pressure seal between a shaft or piston and the walls of a cylinder. Pressure tight sealing components 556 are separated along shaft 554 by a cylindrical spacer sleeve 558 surrounding shaft 554 and disposed between the pressure tight sealing components. Pressure tight sealing components 556 are forced against spacer 558 to prevent relative motion between shaft 554 and the pressure tight sealing components by tightening knobs 197 onto the threaded ends of shaft 554 to provide a biasing force pushing the pressure tight sealing components 556 against spacer 558.

Spacer 558 has an external diameter less than that of the internal diameter of inner surface 560 of cylinder 552. Thus, a space provided between the outer surface 562 of spacer 558 and the inner surface 560 of cylinder 552 defines a flow channel 564 through which high pressure liquid flows from inlet 182 to either or both of outlets 188 and 194, when the instrument is in operation. In some preferred embodiments, valve 180 can be adjusted by the user, by manipulating the position of shaft 554 with knobs 197, to provide three user-selectable positions. In especially preferred embodiments, the three user-selectable positions can be defined by discreet stops along the direction of movement of shaft 554 within cylinder 552. For example, in one particular embodiment, the shaft and cylinder sliding mechanism can be configured, upon a force applied to one or both of knobs 197 to move between three discreet positions along the length of travel of the shaft within the cylinder, each position defining a particular flow path and requiring a force applied to knobs 197 to dislodge the shaft from the discreet position. A variety of mechanisms for providing such discreet sliding action between predefined positions are well known to those of ordinary skill in the art. In other embodiments, where liquid flow exiting both outlets simultaneously is not desired, shaft 554 of valve 180 may be configured, for example with a bistable mechanism, to permit valve 180 to be adjusted by the user to one of two discreet positions, one for directing flow to outlet 188 and the other for directing flow to outlet 194.

As illustrated in FIG. 12, shaft 554 has been moved to the far right of its permissible range of motion. This position defines a first user-selectable position directing a high pressure liquid from inlet 182 through flow channel 564 and out of the valve through outlet 188, which is fluid communication with pressure lumen 118 supplying high pressure liquid to liquid cutting jet nozzle 192 shown in FIG. 1. Such position would be selected by the user of the surgical jet instrument in order to create a liquid cutting jet with the surgical instrument without creating rotation of the liquid jet-driven rotatable shaft of the surgical instrument. A second user-selectable position would be the position obtained by sliding shaft 554 to its leftmost range of travel. In this configuration, high pressure liquid would flow from inlet 182 through flow channel 564 and out of the valve through outlet 194, which is in fluid communication with rotor drive pressure lumen 164. This configuration can be utilized for driving a liquid jet-driven rotatable shaft of the instrument without simultaneously creating a liquid cutting jet with the instrument. Yet a third user-selectable position, in some embodiments, can be achieved by positioning shaft 554 at a position roughly equidistant between its rightmost and leftmost ranges of travel. In this third user-selectable position, high pressure liquid will flow from inlet 182 through flow channel 564 and out of the valve through both outlets 188 and 194. In this configuration, the user may create a liquid cutting jet with the instrument while simultaneously powering a liquid jet-driven rotational shaft of the instrument.

Elements 556 are shown in greater detail in FIG. 13. Element 556 is configured as a pressure-tight sealing component. A "pressure-tight sealing component" as used herein refers to a component that is able to form a pressure-tight seal between two regions of a cylinder, each containing a fluid therein, wherein the fluids contained in the two regions are at different hydrostatic fluid pressures. A "fluid" when in the present context can comprise a liquid, gas, supercritical fluid, slurry, suspension, or any mixture of the above, and refers to the thermodynamic state of the material present in the regions of the cylinder at the temperature and pressure at which the component is used in operation. In the context of use of the pressure-tight sealing component within liquid flow control valve 180, the fluid contained in at least one of the above-mentioned regions of the cylinder will comprise a liquid; however, as apparent to those of ordinary skill in the art, element 556 can also be used for a wide variety of other pressure sealing applications not necessarily involving pressurized liquids.

Element 556 is shown in cross section of FIG. 13 together with a portion of spacer 558. Shaft 554 has been removed in the figure to show the illustrated components with greater clarity. Element 556 may be comprised of a wide variety of materials capable of withstanding the pressures contemplated, such as, for example, a variety of metals, ceramics, plastics, etc. Element 556 is, in preferred embodiments, comprised of a non-elastomeric, semi-rigid plastic that is dimensionally stable within the range of operating pressures contemplated. Preferred plastics include crystalline polymers or semi-crystalline polymers, or amorphous polymers having a glass transition temperature higher than the operating temperature of the apparatus utilizing element 556 as a sealing component. Element 556 can be constructed from a wide variety of engineering plastics, for example, polytetrafluorethylene (PTFE), polypropylene, polyethylene, polyvinylchloride, polyamides, polysulfone, polystyrene, mixtures thereof, etc., as apparent to those of ordinary skill in the art. In one particular preferred embodiment, element 556 is formed from an acetal polymer, for example, polyoxymethylene (Delrin™).

Element 556 includes an integral, flared sealing flange portion 559 that is constructed and arranged to make sealing contact with the internal surface 560 of cylinder 552 within valve 180, while preventing contact between internal surface 560 and both shaft 554 and between internal surface 560 and any other portion of element 556 outside of flange region 559. "Constructed and arranged to make sealing contact" as used herein in reference to flared sealing flange portion 559 refers to at least an outer surface 561 of the flange portion being sized and shaped to form an essentially continuous contact with inner surface 560 of cylinder 552 (i.e., having an outer perimeter with a shape essentially conforming to the shape of cylinder 552). It should be emphasized, that while, in the illustrated embodiment, the shape of cylinder 552 and the outer perimeter of outer surface 561 is essentially circular in cross-section (i.e. cylinder 552 as illustrated comprises a circular cylinder), in other embodiments, the shape of the cylinder and the outer perimeter of outer surface may be other than circular in cross-section, for example, the cylinder may comprise a cylindrical channel with a rectangular, elliptical, triangular, polygonal, or other cross-sectional shape, with the integral, flared sealing flange portion of the sealing element being similarly shaped so that that is constructed and arranged to make sealing contact with the internal surface of the cylinder. Flared sealing flange portion 559 of element 556, when in sealing contact with inner surface 560 of cylinder 552, provides a leak-tight seal at the point of contact between the flared sealing flange portion of the element and the internal surface of the cylinder that is able to withstand a differential in liquid pressure of at least about 1,000 psi without leakage of liquid through the seal. A "differential in liquid pressure" as used herein in the present context refers to a difference in hydrostatic pressure between a liquid contained within flow channel 564 of cylinder 552 and a pressure outside of the region of flow channel 564 (e.g., atmospheric pressure) within cylinder 552. In more preferred embodiments, the seal formed between flange region 559 and surface 560 of cylinder 552 is capable of withstanding a differential in liquid pressure of at least 8,000 psi, more preferably at least 25,000 psi, and most preferably at least 50,000 psi without leakage of liquid through the seal.

In the illustrated embodiment, element 556 is shaped to include a main body portion 563 having a cylindrical shape with an outer diameter $D_f$. As illustrated, flange portion 559 of element 556 is formed integral to surface 565 abutting spacer 558. Surface 565 also includes a ridge 566 for seating against angled internal surface 568 of spacer 558. In other embodiments, flared sealing flange portion 559 may be located along main body portion 563 at a position intermediate spacer abutting surface 565 and knob abutting surface 570. It should also be understood that in other applications element 556 may be configured as a cap having surface 565 extending completely across the centrally disposed bore 572 within the interior of the element. Such a configuration could potentially be useful for use as a pressure sealing cap on the end of a shaft.

As configured for use in liquid directing valve 180, element 556 has a main body portion 563 configured with a tube-like annular shape, wherein centrally disposed bore 572 is disposed entirely through the central region of the element, permitting the element to be mounted to shaft 554, which shaft passes through centrally disposed bore 572, when the element is mounted to the shaft.

Flared sealing flange portion 559 of element 556 has a predefined length 574 and is angled to extend away from outer surface 576 of main body portion 563 and toward inner surface 560 of cylinder 552 of valve 180 when the valve is assembled. The flared sealing flange portion 559 extends away from surface 576 of main body portion 563, as shown, to form a cantilevered circumferential flange around the periphery of element 556. A "cantilevered circumferential flange" refers to a flange that circumscribes the entire outer perimeter of the main body portion of the element and is attached to the main body portion along one of its sides, while having at least two additional sides or faces (e.g., surfaces 561, 577, and 578) not attached to or integral with the main body portion of the element (i.e., having a triangular cross-sectional shape or a trapezoidal or rectangular cross-sectional shape).

Predefined length 574 and minimum thickness 580 of sealing flange portion 559 tend to vary approximately linearly with the size of cylinder 552 in which sealing element 556 is disposed during operation. In one exemplary embodiment utilizing a Delrin plastic element having a main body portion with an external diameter $D_I$ of about 0.182 inch that is used as a pressure-tight sealing component within a cylinder having an internal diameter of about 0.1875 inch, length 574 is about 0.025 inch and thickness 580 is about 0.003 inch.

Sealing element 556 has a second outer diameter $D_O$ defined by an outermost periphery 582 of flange portion 559 that exceeds the outer diameter $D_I$ of main body portion 562. When element 556 is disassembled from cylinder 552 of valve 180, outer diameter $D_O$ of the outermost periphery 582 of flange portion 559 exceeds outer diameter $D_I$ of main body portion 563 by at least about 1%, in other embodiments by at least about 3%, in other embodiments by at least about 5%, and in yet other embodiments by at least about 10%. In one preferred embodiment, outer diameter $D_O$ exceeds diameter $D_I$ by about 5%. Cylinder 552 of valve 180, containing element 556 upon assembly of the valve, has an internal diameter that exceeds outer diameter $D_I$ of main body portion 563 but that is somewhat less than outer diameter $D_O$ of outermost periphery 582 of flange portion 559 of element 556. It should be emphasized that outer diameter $D_O$ of outermost periphery 582 of flange portion 559 as described herein refers to the diameter as measured with element 556 disassembled from valve 180 and not contained within cylinder 552. When element 556 is inserted into cylinder 552, flange portion 559, which is pivotally flexible with respect to main body portion 563, will tend to have a maximum outer diameter of outermost periphery 582 of flange portion 559 that is essentially equal to the inner diameter of cylinder 552. Referring now to the maximum outer diameter $D_O$ of outermost periphery 582 of flange portion 559, as measured with element 556 not assembled into cylinder 552, cylinder 552 typically has an internal diameter less than diameter Doby at least about 0.5%, and in other embodiments at least about 1%, and in yet other embodiments by at least about 2%. In a preferred embodiment, the internal diameter of cylinder 552 is less than external diameter $D_O$ by about 1%.

Flange portion 559 of element 556, in preferred embodiments, has an outer surface 561 extending away from surface 576 of main body portion 563 at an angle γ, with respect to the direction of longitudinal axis 590 of main body portion 563, of between about 1 degree and about 11 degrees. Furthermore, in preferred embodiments, flange portion 559 has an inner surface 578 extending away from surface 565 of main body portion 563 at an angle β, with respect to the direction of longitudinal axis 590, of between about 15 degrees and about 30 degrees. In preferred embodiments, the absolute value of the difference between angles γ and β varies from between about 5 degrees and about 20 degrees. In one preferred embodiment, angle γ is about 8 degrees and angle β is about 20 degrees.

Another aspect of the present invention provides a series of liquid jet surgical instruments including integrated electrocautery for cauterizing blood vessels or other tissue in a surgical field with an electric current. The term "integrated electrocautery" as used herein to refer to certain embodiments of surgical instruments provided by the invention, refers to the inventive surgical liquid jet instruments including one or more electrodes, preferably located at the distal end of the instrument for placement in the surgical field during operation, which electrodes comprise an integral or attached component of the surgical instrument, such that electrocautery can be performed with the surgical instrument without the need for insertion into the surgical field of any additional instrumentation, and without the need for removal and replacement of the surgical instrument from the surgical field. Integrated electrocautery capability in certain embodiments of the inventive surgical instruments can be configured with a single positive electrode located near the distal end of the surgical instrument and can be operated in a monopolar mode. For such embodiments, the electrode provided by the instrument acts as the positive electrode and the body of a patient acts as a source of ground potential, for example via contact with a grounding pad in electrical communication with an external power supply. A "positive electrode" or "positive terminal" as used herein refers to an electrode or terminal of a surgical instrument or external power supply having an electrical potential differing from that of ground potential (0 volts). A "source of ground potential" as used herein refers to an electrode, surface, terminal, etc., that is maintained at essentially ground potential during performance of electrocautery with a surgical instrument.

Preferred surgical instruments, according to the invention, including integrated electrocautery further include at least one lumen therein able to conduct an electrically conductive liquid to the distal end of the instrument for insertion into a surgical field. Such a lumen is able to add conductive liquid to the surgical field in order to maintain an electrocautery electrode at the distal end of the instrument submerged in an electrically conductive liquid so as to enable current flow from a positive electrocautery electrode to a source of ground potential within the environment of the surgical field during electrocautery. Especially preferred instruments including integrated electrocautery include a pressure lumen therein able to conduct a high pressure liquid to the distal end of the instrument and able to form a liquid cutting jet within the surgical field. Some preferred surgical instruments will also include an exhaust lumen with a jet-receiving opening, positioned opposite a jet opening in a nozzle region of the above-mentioned pressure lumen, for evacuation of liquid and debris from the surgical field. Some preferred embodiments of surgical instruments including integrated electrocautery can also include a rotatable shaft therein for powering a tissue contacting component, for example a grinding burr. Such an instrument was described previously in the context of FIG. 1 and is shown and described, as configured with integrated electrocautery below in the context of FIGS. 16A and 16B.

In general, the inventive configurations for providing integrated electrocautery described below may be utilized in a wide variety of surgical instruments capable of delivering a conductive fluid, such as physiological saline or lactated Ringer's solution, to a surgical field of a patient, as would be apparent to those of ordinary skill in the art. In other embodiments, where the distal end of the surgical instrument is utilized in surgical fields that are naturally submersed in conductive fluids or are perfused by other means with conductive fluids, the instruments provided by the invention including integrated electrocautery can lack lumen for delivering conductive fluid to the surgical field, but may instead comprise, for example, a surgical instrument providing only a rotatable shaft that is powered by a liquid jet-driven rotatable rotor positioned within the body of the instrument and drivingly coupled to the rotatable shaft, such that rotation of the liquid jet-driven rotatable rotor causes a corresponding rotation of the rotatable shaft of the instrument as well as rotation of a component at the distal end of the rotatable shaft, such as a grinding burr, etc., which is able to perform a desired surgical task within the surgical operating field.

Some preferred embodiments for providing integrated electrocautery provide surgical instruments having at least two electrodes positioned at the distal end of the instrument and within a surgical operating field during operation of the instrument. Such instruments can be operated in a bipolar mode, where each of the electrodes is maintained at a differing electrical potential, such that there exist a difference in electrical potential between different electrodes of the instrument, tending to drive electrical current along a conducting path within a surgical operating field from one electrode to another. In preferred embodiments of instruments configured with at least two electrodes, at least one of the distal electrodes comprises a positive electrode and at least one other of the distal electrodes comprises a ground potential electrode, such that a complete current path between the positive electrode and the ground electrode at the distal end of the instrument is provided within the surgical field during operation of the instrument.

As discussed above, integrated electrocautery, as provided by the invention, may be configured to be utilized with a wide variety of surgical instruments both described herein and available in the prior art. For example, a particular embodiment of a deployable liquid jet surgical cutting instrument previously disclosed and described in detail in commonly owned U.S. patent application Ser. No. 09/313,679 configured with the inventive system of integrated electrocautery is described below in the current text of FIGS. 14A–14D. It should be understood that in addition to the embodiment illustrated in FIGS. 14A–14D, any of the other embodiments of surgical liquid jet cutting instruments described in U.S. patent application Ser. No. 09/313,679 could be similarly configured with integrated electrocautery as provided by the current invention. As described below, in some preferred embodiments, the at least one integrated electrocautery electrode provided at the distal ends of surgical instruments according to the invention comprises at least a portion of a distal end of a lumen of the surgical instrument configured to either supply liquid to a surgical field (e.g., a pressure lumen) or withdraw liquid from a surgical field (e.g., an evacuation lumen). In some such preferred embodiments, as discussed in more detail below, electrodes are provided at the distal end of one or more lumen of the surgical instruments by selectively coating the external surface of such lumens with an essentially continuous layer of an electrical insulator, while leaving certain regions the lumen uncoated, which uncoated regions providing an electrode surface. An "essentially continuous layer" of electrical insulation as used herein for describing certain coated regions of conductive lumen or other surfaces of the surgical instrument according to the invention refers to such surfaces being coated with an electrical insulator such that there is essentially no, or an acceptably low level of, electrical conduction between the coated region of the surface and another surface or medium through the electrically insulating layer at any electrical potentials up to the maximum electrical potential rating of the surgical instrument (about 1500 volts for typical electrocautery instruments as described herein). In other embodiments, the electrode(s) may comprise probes or conductive elements that are separate or separable from the fluid conducting lumen of the instruments.

Figure 14A:
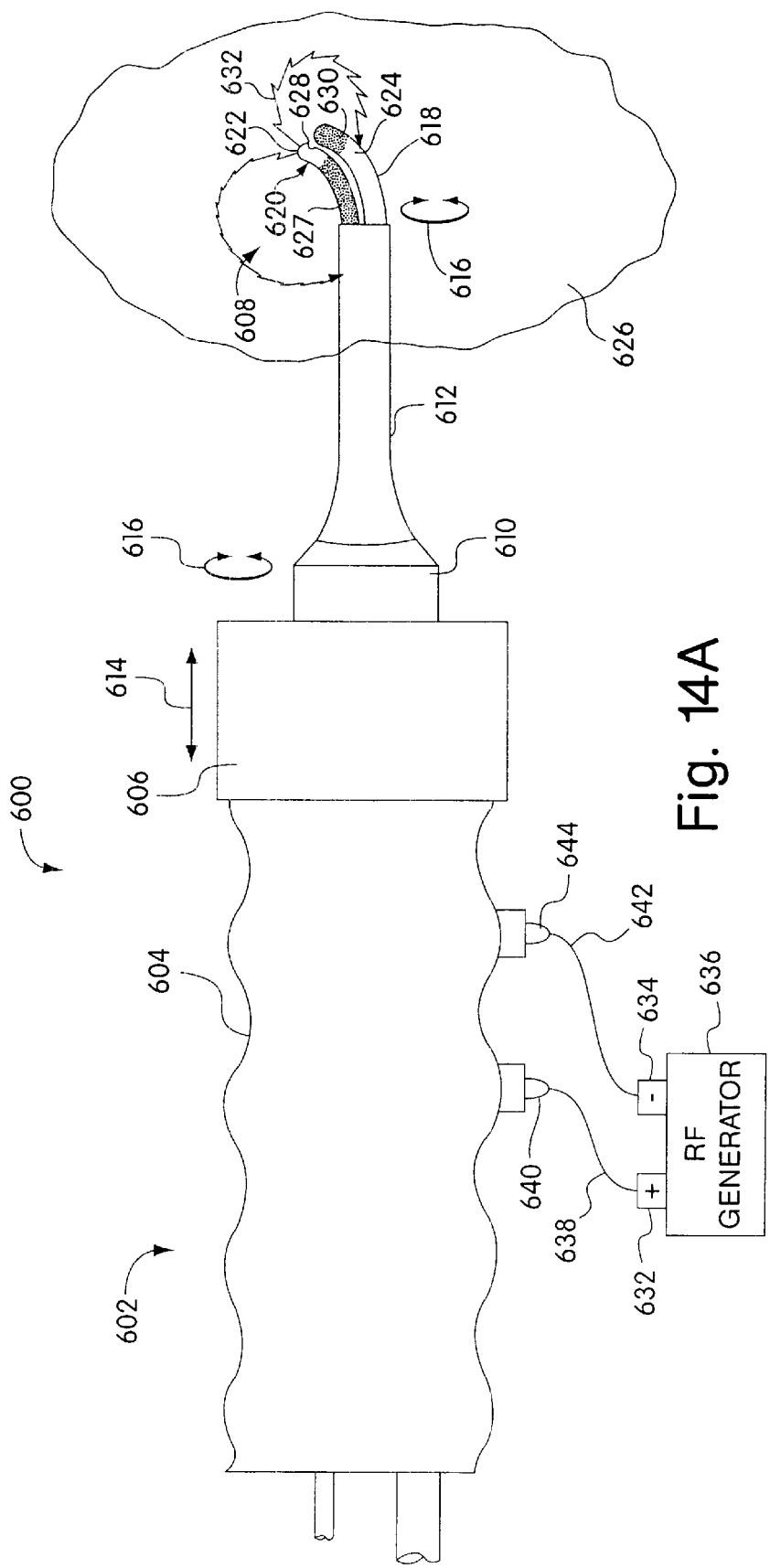
FIG. 14A is a schematic illustration of a rotatably deployable surgical liquid jet instrument including integrated electrocautery electrodes.

An illustrative embodiment for a rotatably deployed surgical liquid jet instrument is shown in FIGS. 14A–14F. Referring to FIG. 14A, surgical instrument 600 includes a body 602 having a grasping region 604 configured to be held within the hand of an operator and an actuating element 606 that comprises a slidable sleeve or collar, which is used to deploy the distal end 608 of surgical instrument 600. Slidable sleeve 606 is positioned to be easily actuated by a single hand of an operator of instrument 600. Slidable sleeve 606 can enable the operator to hold body 602 in at least two different hand/grasping region 604 orientations, so that the operator can actuate slidable sleeve 606 while holding body 602 in either of the at least two hand/grasping region 604 orientations. For example, an operator can grip body 602 in a hand position where the thumb of the operator is located near the distal end of gripping region 604. In such position, the operator can actuate slidable sleeve 606 by moving the slidable sleeve with her thumb. In a second hand/grasping region orientation, the operator can grip body 602, for example, with her thumb positioned toward the proximal end of body 602, while actuating slidable sleeve 606 via one or more of the other four fingers of her hand.

Surgical instrument 600 also includes a collar 610 that is rotatably mounted within body 602. Rotatably mounted collar 610 is typically a cylindrically-shaped sleeve, which may be attached to, or form part of, sheath 612. Distal end 608 of surgical instrument 600 is shown in FIG. 14A in an undeployed configuration. Sliding sleeve 606 in the direction of arrows 614 causes a rotational motion of rotatably mounted collar 610 in the direction shown by arrows 616, which, in turn, causes a rotation of evacuation lumen 618 about a longitudinal axis of sheath 612, which is essentially parallel to the longitudinal axis of body 602 and the longitudinal axis of the portion of evacuation lumen 618 within sheath 612. In other embodiments, upon deployment, evacuation lumen 618 may rotate about the longitudinal axis of sheath 612, which is essentially collinear to the longitudinal axis to of the portion of evacuation lumen 618 within sheath 612, both of which axes are essentially parallel to the longitudinal axis of body 602. In yet alternative embodiments, instead of evacuation lumen 618 rotating upon deployment of instrument 600, evacuation lumen 618 may instead be immobile with respect to body 602 and pressure lumen 620 may rotate upon actuation of slidable sleeve 606.

Surgical instrument 600 as shown is also configured with integrated bipolar electrocautery capability. In the illustrated embodiment, pressure lumen 620 is configured to include a positive electrocautery electrode 622 at its distal end, and evacuation lumen 618 includes a conductive portion 624 of its outer surface, located within surgical field 626 during operation, which act as a ground electrode. Pressure lumen 620 is coated with an essentially continuous layer 626 (shaded region) of an electrical insulator along essentially its entire length, except in a region 622 at its distal end surrounding nozzle 628, which is uncoated and has a conductive surface providing a positive electrode. In preferred embodiments, as shown, evacuation lumen 618 is uncoated along its length, except in a region 630 (shaded region) at its distal end, which region, surrounding the jet-receiving opening, is coated with an essentially continuous layer of electrical insulation. In other embodiments, the roles of pressure lumen 620 and evacuation lumen 618 may be reversed so that evacuation lumen 618 is coated along its length except at its distal end and acts as the positive electrode, and pressure lumen 620 has an outer surface that is conductive along its length, except at its distal end which is coated, and provides a ground electrode. In yet other embodiments, both the positive and ground electrodes may be positioned on the same lumen (i.e. on the pressure lumen or the evacuation lumen). For example, in one such alternative embodiment, the pressure lumen can be configured as described above (i.e. having an essentially continuous layer of an electrical insulator disposed along essentially its entire length, except in a region at its distal end surrounding the nozzle, which is uncoated and has a conductive surface providing a positive electrode) except also including a ground electrode disposed along or wrapped around the outer, insulated surface of the pressure lumen, where the ground electrode has a distal end that is disposed proximal to the conductive region of the outer surface of the lumen that provides the positive electrode. In such an alternative embodiment, the other lumen, which does not provide an electrode (e.g. the evacuation lumen in the above-described configuration), can be, if desired, constructed from an electrically non-conductive material, such as plastic.

FIG. 14A shows the distal end of instrument 600 submersed in an electrically conductive fluid in a surgical field 626. Pressure lumen 620 is coated with insulating layer 626 except at its distal tip. The uncoated, uninsulated distal tip 622 forms the positive integrated electrocautery electrode. Evacuation lumen 618, in the illustrated embodiment, is uninsulated except at distal tip 630. In the illustrated embodiment, distal tip 630 of evacuation lumen 618 is insulated in order to increase the minimum length of the conductive path 632 that electrocautery current travels along within surgical field 626 to prevent burning of tissue at the surface of the ground electrode 624 and to reduce any arcing, shorting, or burning of tissue that may be caused by providing a conductive path length that is too short. This can be especially important when performing electrocautery with surgical instrument 600 in an undeployed configuration, as shown, where the distal ends of pressure lumen 620 and evacuation lumen 618 are in very close proximity.

Upon operation of electrocautery, current will flow from electrode 622 and through the target tissue and electrically conductive fluid in surgical field 626 to a conducting surface at ground potential, for example the uninsulated surface 624 of evacuation lumen 618 and sheath 612, which is in electrical communication with lumen 618. Positive electrode 622 and ground electrode surface 624 of evacuation lumen 618 within the surgical field are preferably sized, based on the power rating of the power supply supplying power to the positive electrode, to focus electrical energy at the positive electrode and disperse the energy at the ground electrode. In typical prior art electrocautery instruments for performing bipolar electrocautery, the positive and ground electrodes are of essentially equal size. In such prior art instruments, essentially all of the tissue located between the electrodes gets desiccated by electric current during operation of the instrument. In the inventive configuration, it is preferred that the surface area of the ground electrode surfaces that are submerged in conductive liquid within surgical field 626 exceed the surface area of positive electrode 622 by at least a factor of 2, more preferably by at least a factor of 5, and most preferably by at least about a factor of 10. In all cases, the ground electrode should be sized, with respect to the size of the positive electrode and the power supplied to the positive electrode, so that it is large enough to prevent boiling of any of the liquid contained within surgical field 626, when performing electrocautery with the instrument. For example, in the embodiment illustrated, positive electrode 622 comprises a positive electrode surface area of about 0.2 cm$^2$, while the insulated surface 630 of the distal end of evacuation lumen 618 comprises the distal-most about 0.20 inch of the lumen, providing a conductive surface 624 of evacuation lumen 618 in surgical field 626 comprising a ground electrode that has a surface area of at least about 2 cm$^2$.

Pressure lumen 620 and evacuation lumen 618, are connected in electrical communication with positive terminal 632 and ground terminal 634 of external power supply 636 respectively. External power supply 636 preferably comprises a radio frequency (RF) generator. For embodiments where the surgical instrument is configured to provide bipolar electrocautery, surgical instrument 600 can potentially be used with the bipolar output of essentially any commercially available RF generators for use in electrocautery. Such generator are typically configured to supply frequencies of between about 500 KHz and about 2 MHz at power supply levels up to about 80 watts. Positive terminal 632 of power supply 636 is in electrical communication with body 602 of instrument 600 via electrical connector 638 and jack 640. Ground terminal 634 of power supply is in electrical communication with body 602 of instrument 600 via electrical connector 642 and jack 644. Jack 640 is, in turn, in electrical communication with pressure lumen 620 within body 602 and jack 644 is, in turn, in electrical communication with evacuation lumen 618 within body 602 by connections best illustrated in FIG. 14D and described below. Jacks 640 and 644 and connections 638 and 642 can be any of a wide variety of electrical connection means readily apparent to those of ordinary skill in the art. In one particular example, electrical connections between body 602 of instrument 600 are made through standard "banana" jacks that are mounted to the instrument. In some preferred embodiments, jacks 640 and 644 are eliminated, and connectors 638 and 642 are connected directly to pressure lumen 620 and evacuation lumen 618, respectively, within body 602, similar to the connection of connectors 668 and 669 to the lumen, as described below in the context of FIG. 14D. In an alternative embodiment, the inventive electrocautery instruments can also be operated in a bipolar mode by connecting the instrument to the monopolar output of a commercially available monopolar power supply for use in electrocautery. In such embodiments, pressure lumen 620, providing the positive electrode can be connected in electrical communication with the positive monopolar terminal of the power supply, while evacuation lumen 618, providing an electrode at ground potential, can be connected in electrical communication with the power supply's grounding connection. Also power supplied to the instrument from, for example, power supply 636 for performing electrocautery may, in some embodiments, be user controllable via a switch or other means provided on power supply 636, body 602, or via a remote switch, for example a foot operated switch, etc., as apparent to those of ordinary skill in the art.

In the illustrated embodiment, the pressure and evacuation lumen are constructed from a conductive material, such as stainless steel, that has a relatively low resistance to electrical current flow. The insulating coating provided on the outer surfaces of the lumen as described can comprise any insulating coating known to those of ordinary skill in the art. In one preferred embodiment, the coating comprises a polymeric coating formed on the surfaces of the lumen as shown using commercially available shrink-wrap tubing, for example polyvinylidene fluoride (PVDF) shrink wrap tubing. In another embodiment, the insulating coating comprises a polymeric coating (e.g. PVDF) formed on the outer surface by a variety of well known coating methods, for example spray coating, brush coating, dip coating, etc. with a variety of commercially available polymer layer forming solutions as known in the art. In one preferred embodiment, the insulating layer formed on pressure lumen 620 comprises a polymeric coating formed on the surface of the lumen using PVDF shrink-wrap tubing, while the insulating layer formed on the distal end of evacuation lumen 620 is formed by spray coating with a PVDF layer forming solution.

The thickness of the electrical insulating layer should be chosen to prevent electrical conduction through the layer during operation at maximum expected operating potentials of the instrument. The thickness will depend upon the well known electrical properties of the particular type of commercially available electrical insulation chosen and can be readily determined by those of ordinary skill in the art. In one embodiment, PVDF shrink-wrap tubing having a thickness of between about 0.004 inch and about 0.006 inch is used as the electrical coating for an instrument having a 1,500 volt peak-to-peak rating.

Figure 14B:
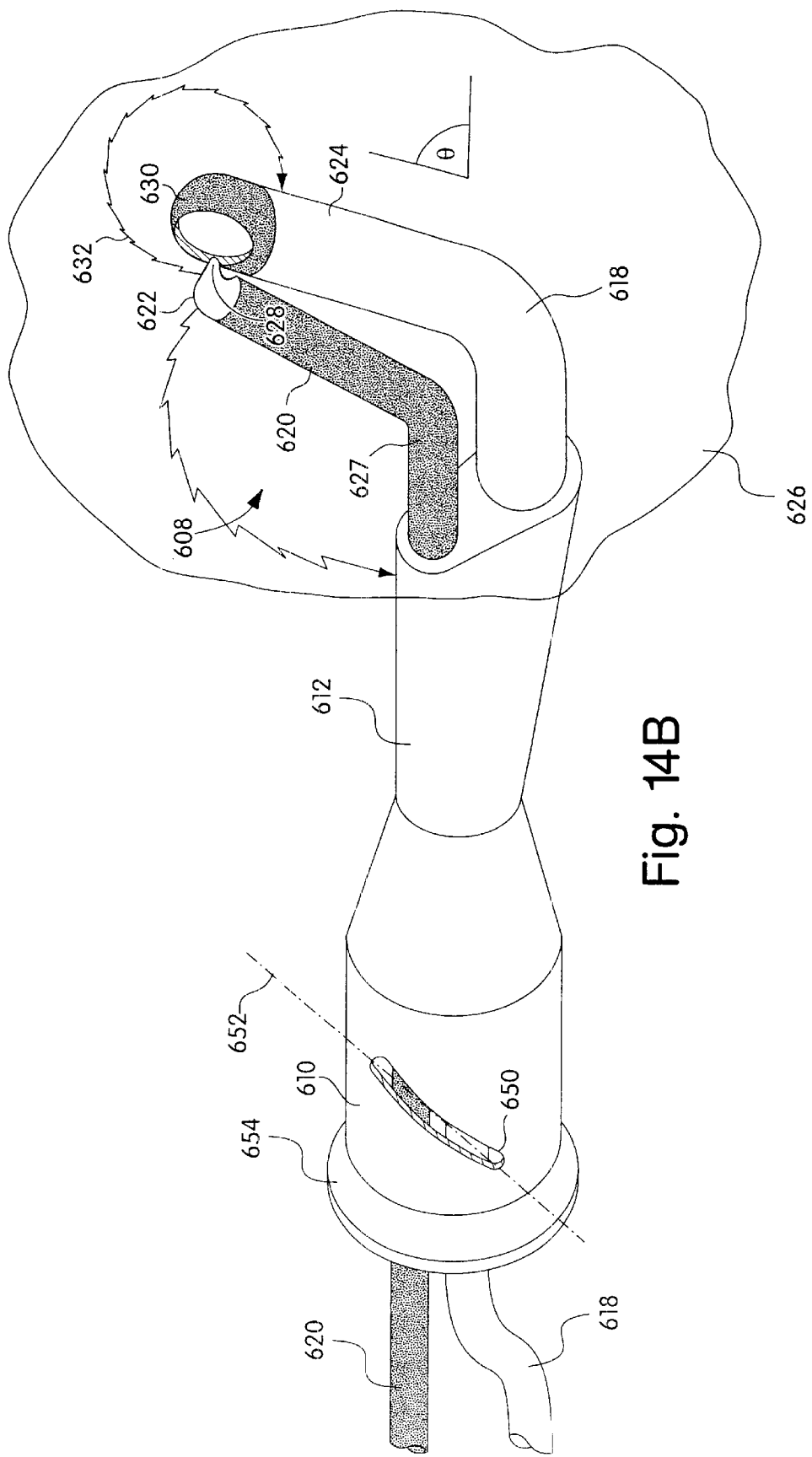
FIG. 14B is a schematic illustration of a portion of the surgical liquid jet instrument as in FIG. 14A showing more clearly the distal end of the instrument, when in the undeployed configuration.
Figure 14C:
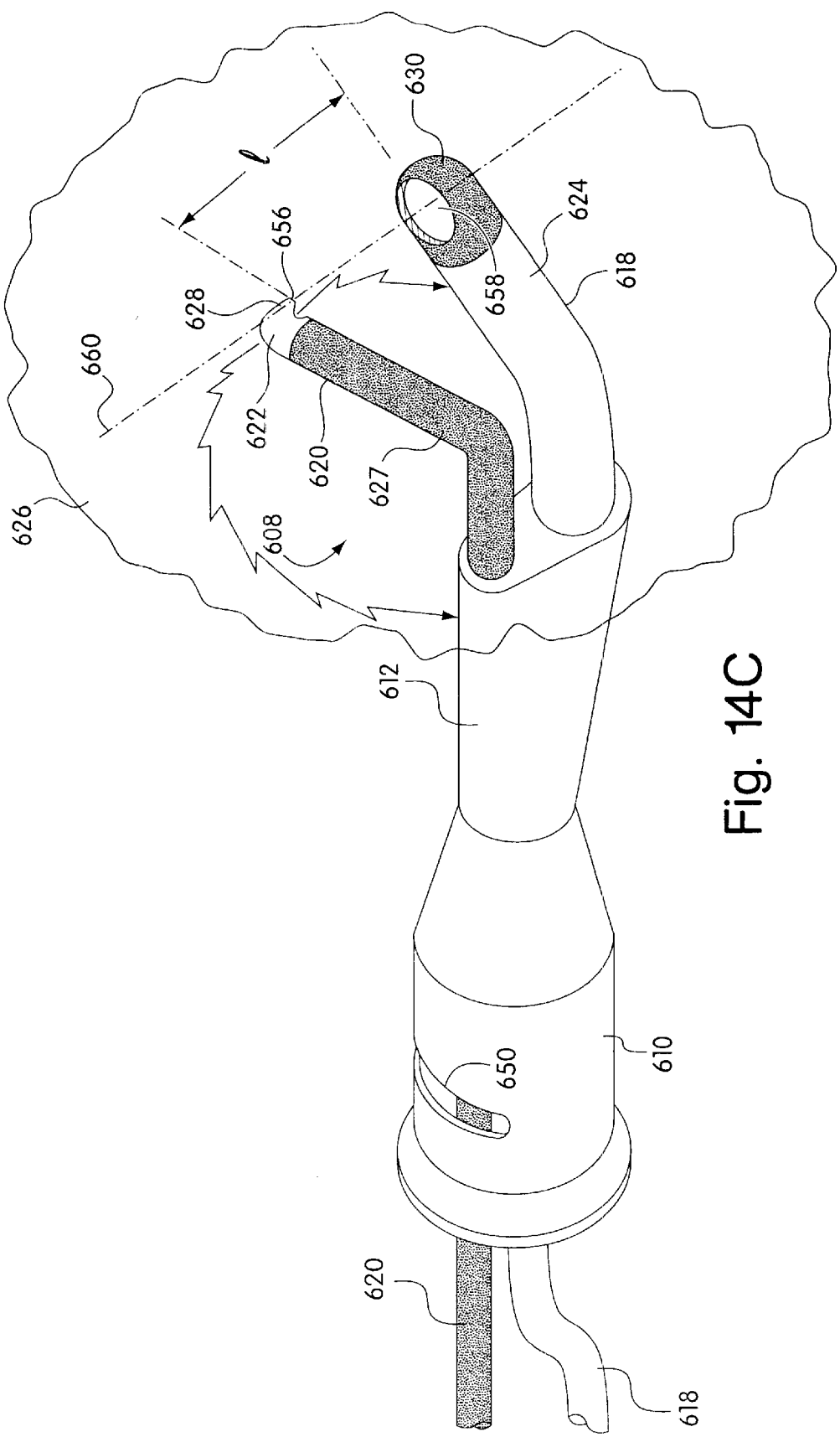
FIG. 14C is a schematic illustration of a portion of the liquid jet instrument as in FIG. 14A showing more clearly the distal end of the instrument, when in the deployed configuration.

The distal end of surgical instrument 600 is shown in greater detail in FIGS. 14B and 14C. FIGS. 14B and 14C also show sheath 612 and rotatably mounted collar 610 in greater detail. Distal end 608 of surgical instrument 600 is shown in FIG. 14B in the undeployed position and in FIG. 14C in the deployed position. In the undeployed position, distal end 608 has a cross-sectional dimension, length, and angular orientation θ with respect to the longitudinal axis of the sheath 612 and the longitudinal axis of the body 602 of instrument 600, which are selected to facilitate insertion of distal end 608 into a confined surgical operating space, for example a joint capsule, for a particular surgical procedure. For example, for arthroscopy, at least one cross-sectional dimension of distal end 608, when in the undeployed configuration, should be no greater than about 2.8 mm, the length of distal end 608 is preferably between 10 and 15 mm, and angle θ is preferably about 15 degrees. Pressure lumen 620 is fixably mounted within body 602, so that it is essentially immobile with respect to body 602, and is rotatably mounted within sheath 612 and rotatably mounted collar 610 so that the sheath can rotate around the outer surface of the pressure lumen upon deployment of distal end 608. By contrast, evacuation lumen 618 is fixably mounted to sheath 612 and/or rotatably mounted collar 610, but is rotatably moveable within body 602 upon rotation of rotatably mounted component 610, so that rotation of rotatably mounted collar 610 and sheath 612 causes a corresponding rotation of evacuation lumen 618 resulting in deployment of distal end 608. Rotatably mounted collar 610 includes a slot or groove 650 having a longitudinal axis 652 that is non-parallel with respect to the longitudinal axis of rotatably mounted collar 610 and the longitudinal axis of body 602 of instrument 600. Slot 650 is used to create rotation of rotatably mounted collar 610 upon movement of slidable sleeve 606, as described in more detail below. Rotatably mounted collar 610 also includes a bearing flange 654 which is mounted within body 602 of instrument 600 to allow for rotation of collar 610, as described in more detail below. Deployment of distal end 608, as shown in FIG. 14C, establishes a separation distance l between jet opening 656 in nozzle 628 and jet-receiving opening 658 at the distal end of evacuation lumen 618. Separation distance l defines a liquid jet path length, when the instrument is in operation. In certain preferred embodiments, axis 660 which defines the direction of a central region of the liquid jet emitted from jet opening 656 when the instrument is in operation, is non-parallel with respect to the longitudinal axes of sheath 612 and body 602 of instrument 600. Typically, for such embodiments, axis 660 forms an angle with respect to the longitudinal axis of body 602 that is between about 45 and 115 degrees, more typically between about 80 and about 100 degrees, and most typically about 90 degrees.

Figure 14D:
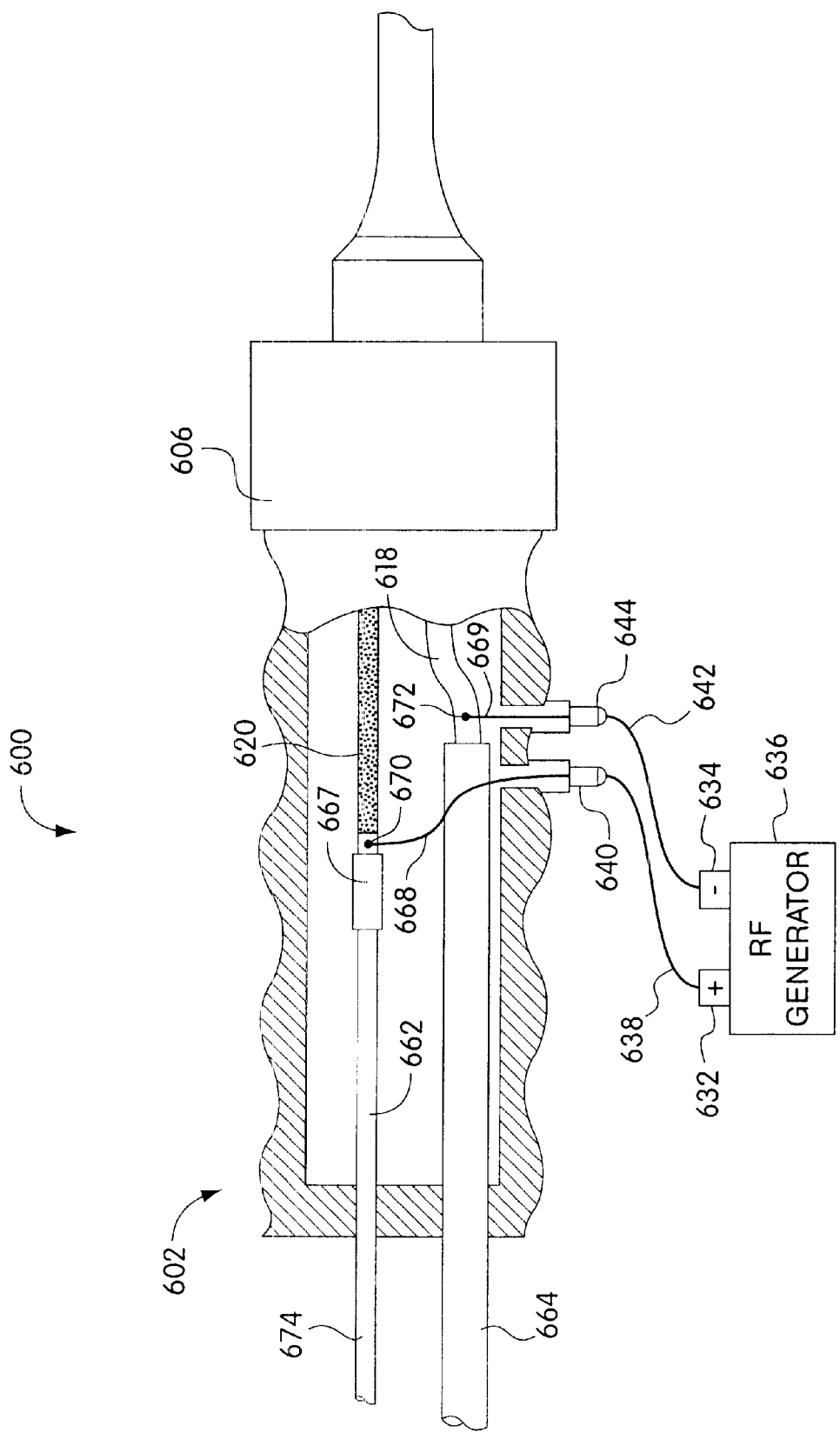
FIG. 14D is a partially-cutaway, schematic illustration of a portion of the surgical liquid jet instrument as in FIG. 14A.

FIG. 14D shows a partially cutaway view of surgical instrument 600 showing more clearly the proximal end of body 602 and the connection of pressure lumen 620 to high pressure liquid supply conduit 662 and evacuation lumen 618 to evacuation conduit 664. Pressure lumen 620 can be connected to high pressure liquid supply conduit 662 via any of a wide variety of high pressure tubing connectors 667 well known in the art. Pressure lumen 620 and/or high pressure liquid conduit 662 are fixably mounted within body 602 to prevent movement of pressure lumen 620 with respect to body 602 during deployment. Evacuation lumen 618 rotates within body 602 upon movement of actuating element 606. Evacuation lumen 618 is connected to evacuation conduit 664, which is flexible and/or twistable within body 602, to allow evacuation lumen 618 to rotate.

FIG. 14D also illustrates one embodiment for providing electrical connections between pressure lumen 620 and positive jack 640 and between evacuation lumen 618 and ground jack 644 within body 602. Positive jack 640 is electrically connected to pressure lumen 620 via a wire or other electrical connector 668, and ground jack 644 is electrically connected to evacuation lumen 618 via a wire or other electrical connector 669. Wire/connector 668 is, in turn, crimped to, soldered to, or otherwise connected in electrical contact (by any suitable means known to those of ordinary skill in the art) to an electrically conductive surface of pressure lumen 620 at point 670; likewise, wire/connector 669 is, in turn, crimped to, soldered to, or otherwise connected in electrical contact to an electrically conductive surface of pressure lumen 618 at point 672. Either or both of high pressure conduit 662 and high pressure connector 667 should be constructed from, or coated with, an electrically insulating material (e.g. a plastic material) to prevent exposure of an operator to electrical shock via contact with the region 674 of the high pressure conduit extending outside of body 602.

Figure 14E:
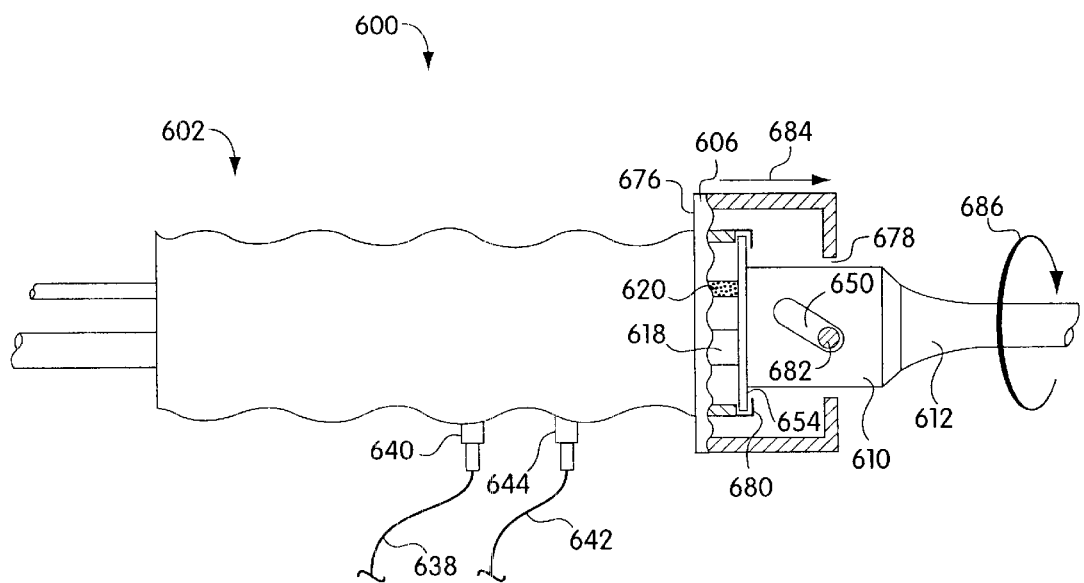
FIG. 14E is a partially-cutaway, schematic illustration of a portion of the surgical liquid jet instrument as in FIG. 14A.
Figure 14F:
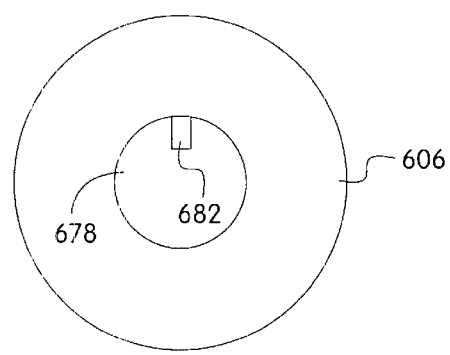
FIG. 14F is a schematic illustration of the actuating element of the surgical liquid jet instrument as in FIG. 14A.

The actuating mechanism by which actuating element 606 causes rotation of rotatably mounted collar 610 and sheath 612, in order to deploy distal end 608 of instrument 600, is shown more clearly in FIGS. 14E and 14F. Referring to FIG. 14E, a cut away view of actuating element 606 is shown. Actuating element 606 can be generally cylindrical in shape and includes two apertures 676 and 678. Aperture 676 is located on the proximal surface of actuating element 606 and allows actuating element 606 to accommodate body 602 of instrument 600. Aperture 678 is located on the distal surface of actuating element 606 and has a circumference that is nearly equal or slightly greater than the outer circumference of rotatably mounted collar 610, thus allowing rotatably mounted collar 610 to pass through, and rotate within, aperture 678. Bearing flange 654 of rotatably mounted collar 610 is rotatably mounted within bearing slots 680 of body 602. Shown in FIG. 14F, actuating element 606 includes a pin 682 mounted within aperture 678. As shown more clearly in FIG. 14E, when assembled, pin 682 fits within slot 650 of rotatably mounted collar 610 so that as an operator slides actuating element 606 in the direction of arrow 684, pin 682 slides forward in slot 650 causing rotation of rotatably mounted collar 610 in the direction shown by arrow 686, thus causing deployment of the distal end of instrument 600.

Figure 15:
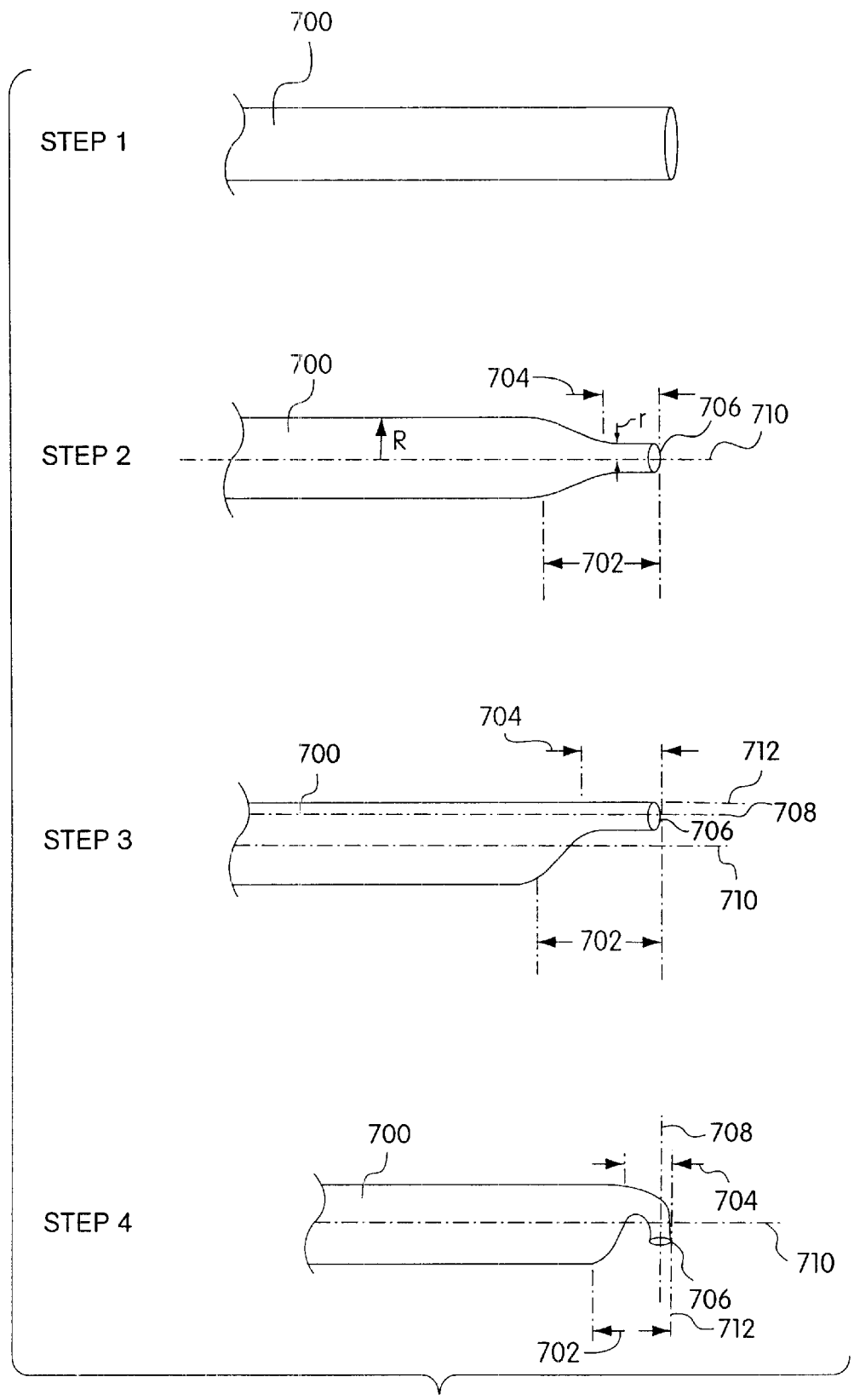
FIG. 15 is a series of schematic illustrations illustrating a method for forming a liquid jet nozzle region.

FIG. 15 illustrates a preferred method, according to the invention, for forming the nozzle shown above in FIGS. 14A and 14B for deployable liquid jet instruments having adjustable liquid jet cutting path lengths. Such instruments and nozzles are described in greater detail in commonly owned U.S. patent application Ser. No. 09/313,679. Step 1 of FIG. 15 entails providing a tubular conduit 700 for use in forming a pressure lumen. The tubular conduit is typically formed of a biocompatible metal such as surgical stainless steel and is selected to have a burst strength sufficient to withstand the contemplated liquid pressures (e.g., a burst strength of at least 50,000 psig).

Step 2 of the method comprises necking down an end of conduit 700 to form a necked region 702 having a reduced cross-sectional area, which necked region tapers into a jet nozzle region 704 having an essentially constant internal cross-sectional area. Jet nozzle region 704 terminates at its distal end in jet opening 706. Necked region 702 can be formed in conduit 700 by a variety of means known in the art, for example by swaging, crimping, or hot-drawing the distal end of conduit 700 to form necked region 702 and jet nozzle region 704. At the end of Step 2, pressure lumen conduit 700 has an internal radius R, jet nozzle region 704 has a minimum internal radius r, and jet nozzle region 704 is essentially co-linear with the axial center line 706 of the tube comprising the pressure lumen 700 outside of necked region 702.

Step 3 of the method involves offsetting jet nozzle region 704 with respect to tube 700 so that the axial center line 708 of nozzle region 704 is offset from the axial center line 710 of tube 700 outside of necked region 702, by a distance D=R−r, so that the jet nozzle region 704 and the tubular conduit 700 abut each other along at least one line 712 co-linear to an external surface of tubular conduit 700.

For embodiments where it is desired that at least a central region of the liquid jet emitted from jet opening 706 be directed in an orientation that is not parallel with axis 710, jet nozzle region 704 may be bent with respect to axis 710 as shown in optional Step 4. In typical embodiments, nozzle region 704 is bent so that the axial center line 708 of jet nozzle region 704 forms an angle with respect to axis 710 that is between 45 degrees and 115 degrees, more typically between about 80 degrees and 100 degrees, and most typically about 90 degrees. Also preferably nozzle region 704 is bent with respect to tube 700 so that essentially no portion of jet nozzle region 704 projects radially beyond a perimeter that is defined by an outer surface of tube 700 outside of necked region 702. In addition to providing a method for forming liquid jet nozzles that have a relatively large length to minimum diameter ratio and that are relatively easy and inexpensive to manufacture, the inventive method also provides a pressure lumen having a maximum cross-sectional profile that does not exceed the diameter of the tubing comprising the pressure lumen. In addition, the nozzles formed by the method outlined in FIG. 15 also advantageously provide improved efficiency for forming a liquid jet as a high pressure liquid streams through the nozzle. The efficiency of forming the liquid jet is improved over nozzle designs comprising, for example, a hole bored in the side of a lumen, due to the fact that necked region 702 provides a smooth tapering flow path for the liquid flowing into nozzle region 704, thus reducing turbulence, recirculating flow patterns, and friction at the jet nozzle inlet. This effect is known in the fluid mechanical arts as the "vena contracta" effect and can improve fluid flow efficiencies through nozzles by as much as 30%.

Figure 16A:
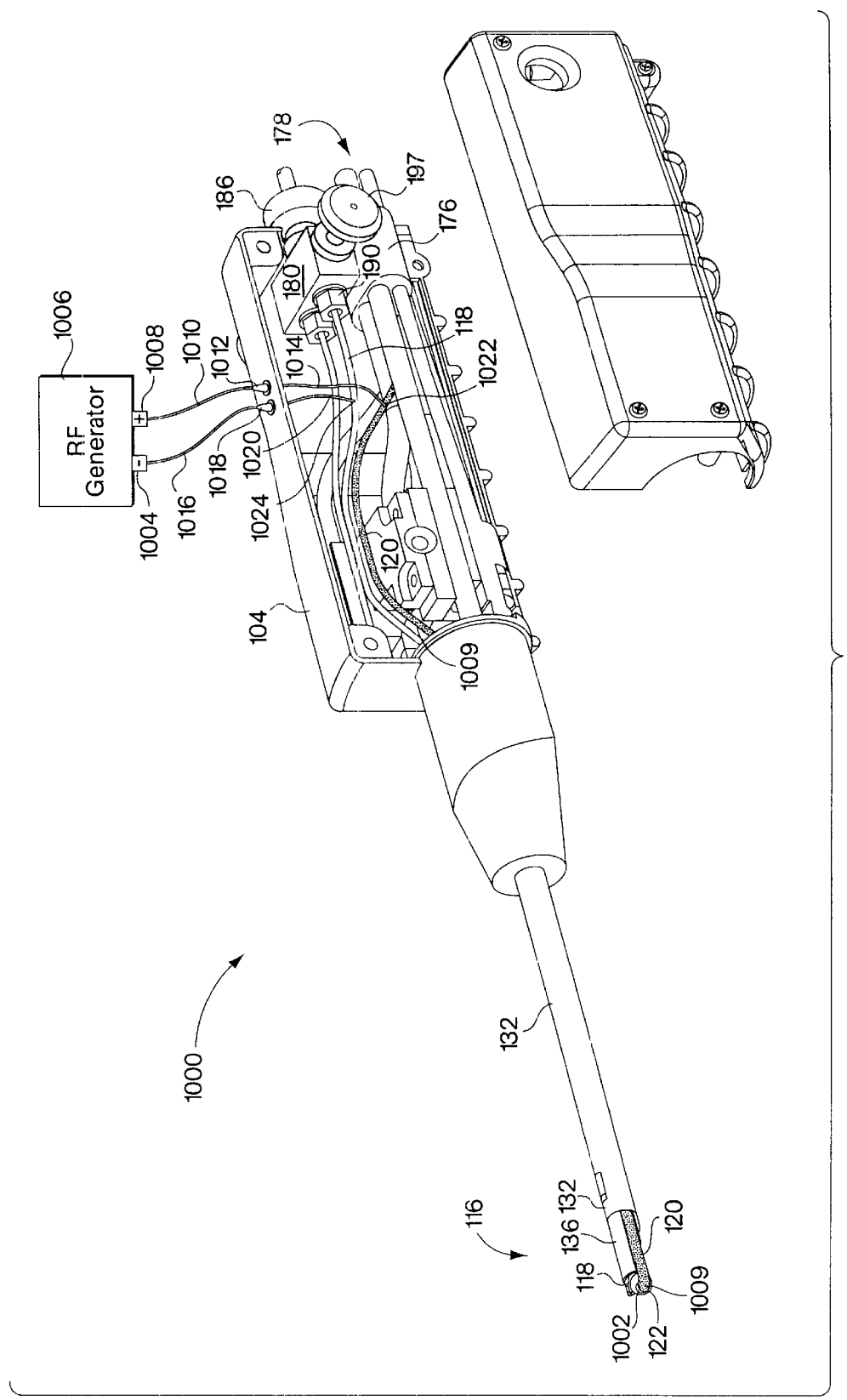
FIG. 16A is a schematic, perspective illustration of a surgical instrument as in FIG. 1, but including integrated electrocautery electrodes.
Figure 16B:
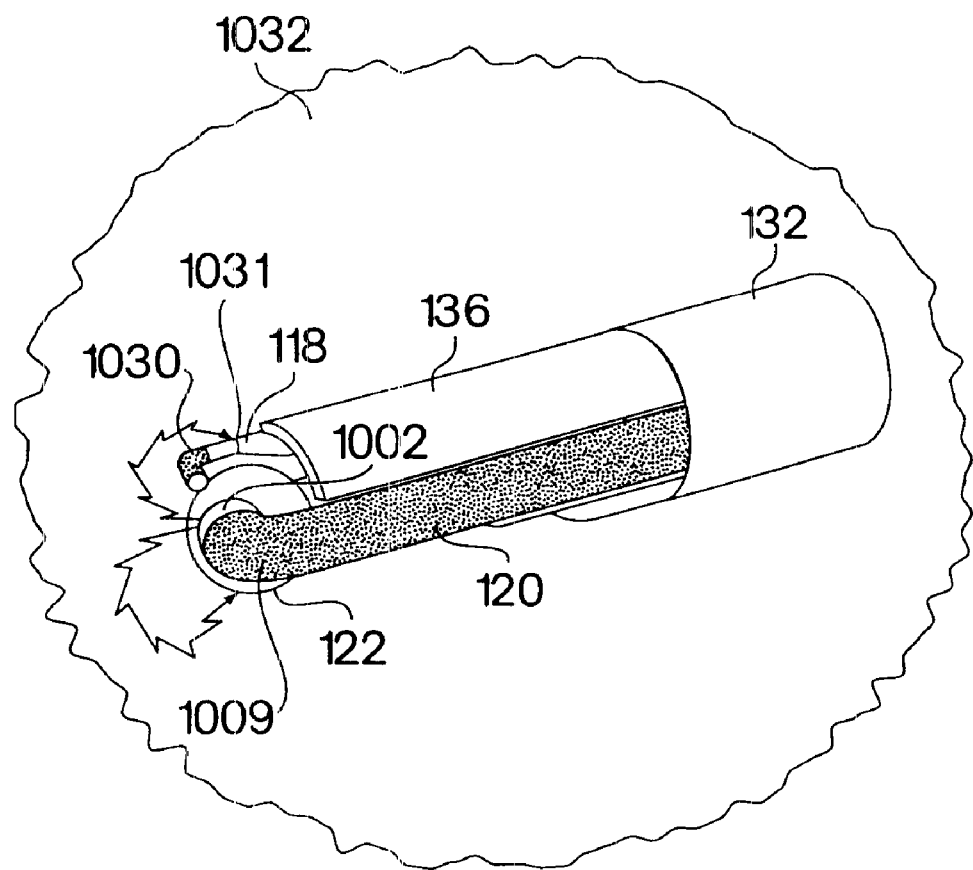
FIG. 16B is a schematic, perspective illustration of a portion of the surgical instrument as in FIG. 16A, showing the configuration of the distal end of the instrument.

FIGS. 16A and 16B illustrate a surgical instrument 1000 including integrated bipolar electrocautery that is similar in configuration with surgical instrument 100 previously shown in FIG. 1 above. The integrated electrocautery configuration for instrument 1000 is similar to that described above for instrument 600 of FIGS. 14A–14F, except that for instrument 1000, which includes a grinding burr 122 located at the distal end 116 and including a liquid jet-driven rotatable rotor and rotatable shaft for rotating the grinding burr, it is preferable to utilize the liquid cutting jet evacuation lumen 120 as the lumen providing positive electrode 1002 at the distal end of the surgical instrument. It is preferred to utilize evacuation lumen 120 as the positive electrode in surgical instrument 1000 because evacuation lumen 120 is connected within body 104 of the instrument to evacuation conduit connecting block 176 which, in turn, is connected to evacuation conduits 178, which extend from the proximal end of the surgical instrument. Evacuation conduit connecting block 176 and conduits 178 are constructed of electrically non-conductive polymeric materials that do not conduct electricity from evacuation lumen 120 to any surface of the instrument in contact with the user during operation. Conversely, cutting jet pressure lumen 118, which is connected within body 104 in electrical communication with ground terminal 1004 of external power supply 1006, is connected via high pressure connector 190 to liquid flow directing valve 180. The high pressure connector and liquid flow directing valve, as well as high pressure tubing coupler 186 and, in some embodiments, knobs 197, may be constructed of conducting materials and could come in contact with an operator of the device during operation. Thus, it is important that such surfaces be maintained at ground potential during operation of the electrocautery electrodes of the device.

External power supply 1006 preferably comprises a radio frequency generator as previously described in the context of FIG. 14A above. Positive terminal 1008 of power supply 1006 is in electrical communication with evacuation lumen 120 via electrical connector 1010, jack 1012, and electrical connector 1014 within body 104 of the instrument. Liquid cutting jet pressure lumen 118 is connected in electrical communication with ground terminal 1004 via electrical connector 1016, jack 1018, and electrical connector 1020 within body 104 of the instrument. Jacks 1012 and 1018 as well as connections 1022 and 1024 of the electrical conductors within body 104 to the lumen can be essentially identical to those described above in the context of surgical instrument 600 of FIGS. 14A–14F. In some preferred embodiments, jacks 1012 and 1018 are eliminated, and connectors 1016 and 1020 are connected directly to pressure lumen 118 and evacuation lumen 120, respectively, within body 104. Also, as described above, power supplied to the instrument from power supply 1006 for performing electrocautery may, in some embodiments, be user controllable via a switch or other means provided on power supply 1006, body 104, or via a remote switch, for example a foot operated switch, etc., as apparent to those of ordinary skill in the art.

Evacuation lumen 120, in electrical communication with positive terminal 1008 of external power supply 1006, is preferably insulated with an essentially continuous layer 1009 of electrical insulation (shaded region) along its entire length except at distal tip 1002 which forms a positive electrocautery electrode, as was previously described above in the context of pressure lumen 620 of instrument 600. In contrast to instrument 600 above, and as previously described, instead of the pressure lumen that forms a liquid cutting jet being configured to form the positive electrode, in system 1000, it is preferred that evacuation lumen 120 be so configured. The relative size of the integrated electrocautery electrodes in surgical instrument 1000 and the electrically insulating coating used for insulating the lumen of the instrument are, in preferred embodiments, essentially the same as that previously described for instrument 600 shown in FIGS. 14A–14F.

FIG. 16B shows the distal end 116 of instrument 1000 submersed in an electrically conductive fluid in a surgical field 1032. Evacuation lumen 120 is coated with electrically insulating layer 1009 except at its distal tip. The uncoated, uninsulated distal tip 1002 forms the positive integrated electrocautery electrode. Pressure lumen 118, in the illustrated embodiment, is uninsulated except at distal tip 1030. In the illustrated embodiment, distal tip 1030 of pressure lumen 118 is insulated (shaded region), as previously described above for evacuation lumen 618 of surgical instrument 600, in order to reduce any arcing, shorting, or burning of tissue that may be caused by providing a conductive path length that is too short. Upon operation of the electrocautery electrode 1002 current flows from electrode 1002 and through the target tissue and electrically conductive fluid in surgical field 1032 to a conducting surface at ground potential that is in electrical communication with the ground terminal of the power supply, for example the uninsulated surface 1031 of pressure lumen 118, as well as other conducting surfaces within surgical field 1032 that are in electrical communication with the pressure lumen, such as grinding burr 122, burr tip support 136, sheath 132, etc. Instrument 1000 could, in alternative embodiments, be connected to a power supply providing monopolar output for performing electrocautery, as was previously described for instrument 600. Also, in other embodiments, because the distal ends of evacuation lumen 120 and pressure lumen 118 are maintained at an essentially constant separation distance during operation of the device, unlike deployable device 600 shown previously in FIGS. 14A–14F, insulated tip 1030 of pressure lumen 118 can be eliminated (i.e., the entirety of the external surface of pressure lumen 118 may be electrically conductive) without unduly affecting performance of electrocautery with the instrument.

The inventive surgical instruments described herein enable the performance of a number of inventive surgical methods. For example, by utilizing the surgical instruments provided according to the invention, which provide both a liquid cutting jet and a rotatable component at the distal end of the instrument, surgical procedures may be performed involving both liquid jet cutting/ablating and other tasks that utilize or require rotation of a rotatable component in a surgical field, without the need for exchanging surgical instruments within the surgical field or providing multiple instruments to the surgical field. For example, the invention enables an operator of such an instrument to insert the surgical instrument into a surgical field of a patient, create a liquid cutting jet with the surgical instrument to cut or ablate a tissue or other material within the surgical field and also cause rotation of a rotatable component of the same surgical instrument within the surgical field to perform a desired surgical task, for example contacting the rotatable component with a tissue within the surgical field (e.g., bone tissue) and grinding, cutting, or ablating the tissue with a rotating surface of the rotatable component.

In some preferred embodiments, a surgical instrument provided according to the invention, for example surgical instrument 100 shown in FIG. 1, can be inserted into a surgical field endoscopically, for example via use of a trocar. In one particularly preferred embodiment, the surgical instruments are utilized within the joint capsule of a patient, for example in the knee or shoulder joint of a patient, for performing an arthroscopic surgical procedure. Utilizing surgical instrument 100, for example, further enables an operator of the instrument to perform surgical liquid jet cutting/ablating while evacuating debris and liquid created by the liquid cutting jet from the surgical field with the surgical instrument without the need for applying a source of external suction in fluid communication with the liquid cutting jet evacuation lumen of the instrument. Also, as discussed above, liquid flow directing valve 180 enables a user of surgical instrument 100 to selectively direct high pressure fluid to either perform liquid jet cutting with the instrument or to utilize the liquid jet-drive rotatable component of the instrument via manipulation of the valve. Alternatively, in some embodiments, the operator can also direct high pressure liquid to both create a liquid cutting jet and drive the liquid jet-drive rotatable component simultaneously in order to perform both liquid jet cutting and, for example grinding etc. with the rotatable component, at the same time.

Furthermore, surgical instruments provided according to the invention that include integrated electrocautery also permit an operator of the instrument, in addition to the surgical tasks described above, to apply an electrical signal to an electrode of the same surgical instrument used for liquid jet cutting in order to cauterize tissue within the surgical field. In some embodiments, electrocautery may be performed as a separate and distinct step from either liquid jet cutting or utilization of a rotatable component of the instrument, or, in other embodiments, electrocautery may be performed simultaneously with the operation of the liquid cutting jet and/or rotatable component capabilities of the instrument. For example, by performing electrocautery while simultaneously controllably evacuating a portion of the liquid from a surgical field with an evacuation lumen of the surgical instrument, for example by applying suction to a sheath surrounding the rotatable shaft of the instrument or by operating a liquid cutting jet to create an evacuation via eductor pump action, an operator with visual access to the surgical field can be able to visualize a trail of blood (i.e., a blood stream flowing along a stream line from the site of a bleed to the inlet of the source of evacuation provided by the surgical instrument) and can stop the bleeding with the instrument before visualization of the entire surgical field is compromised (i.e., before the entire surgical field is rendered opaque due to the presence of blood therein). Upon visualizing the trail of blood during the operation of the instrument, the user can move the surgical instrument within the surgical field along the trail of blood towards the bleeding vessel, while continuously providing evacuation to the instrument. Upon reaching the site of bleeding, the operator can place an electrocautery electrode provided on the surgical instrument in proximity to the bleeding vessel and apply an electrical signal to the electrode to electrocauterize the bleeding vessel to stop the bleeding therefrom. Such a method is particularly useful for endoscopic surgical procedures, for example arthroscopy procedures in the joint capsule of a patient, where the surgical field is visually monitored with an endoscopic camera.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed:

1. A method comprising:
   inserting a surgical instrument into a surgical field of a patient;
   creating a liquid cutting jet with the surgical instrument;
   cutting or ablating a first selected tissue of the patient with the liquid cutting jet;
   rotating a rotatable component of the same surgical instrument;
   contacting a rotating surface of the rotatable component with a second selected tissue of the patient; and
   grinding, cutting, or abrading the second selected tissue with the rotating surface.

2. The method as in claim 1, further comprising after the creating step, the step of:
   directing the liquid cutting jet towards a jet-receiving opening in an evacuation lumen of the surgical instrument.

3. The method as in claim 2, further comprising:
   removing liquid comprising the liquid cutting jet and the first selected tissue from the surgical field without applying a source of external suction in fluid communication with the evacuation lumen.

4. The method as in claim 1, wherein the rotatable component comprises a grinding burr.

5. The method as in claim 4, wherein the second selected tissue comprises bone.

6. The method as in claim 1, further comprising, after the grinding step, the step of:
   evacuating at least a portion of any debris and fragments of the second selected tissue generated during the grinding step from the surgical field.

7. The method as in claim 1, wherein the rotating step comprises:
   supplying a rotatable shaft in the instrument, the shaft having a distal end, which includes the rotatable component, and a proximal end;
   coupling the proximal end of the shaft in driving engagement with a rotatable rotor positioned within a body of the surgical instrument, such that when the instrument is in operation, rotation of the rotatable rotor causes a corresponding rotation of the rotatable shaft;
   providing a pressure lumen having a proximal end, and a distal end that is contained within the body of the instrument, the pressure lumen having sufficient burst strength to conduct a high pressure liquid, the distal end of the pressure lumen including a nozzle therein that is shaped to form a liquid jet as a liquid at high pressure flows therethrough; and
   directing at least a portion of the liquid jet emanating from the nozzle so that it impacts a surface of the rotatable rotor, thereby imparting rotational motion to the rotor.

* * * * *